(12) United States Patent
Labib et al.

(10) Patent No.: US 11,807,898 B2
(45) Date of Patent: Nov. 7, 2023

(54) METHOD FOR DETERMINATION OF CELLULAR MRNA

(71) Applicant: THE GOVERNING COUNCIL OF THE UNIVERSITY OF TORONTO, Toronto (CA)

(72) Inventors: Mahmoud Labib, Toronto (CA); Edward H. Sargent, Toronto (CA); Shana O. Kelley, Toronto (CA)

(73) Assignee: The Governing Council of The University of Toronto, Toronto (CA)

( * ) Notice: Subject to any disclaimer, the term of this patent is extended or adjusted under 35 U.S.C. 154(b) by 465 days.

(21) Appl. No.: 16/639,433

(22) PCT Filed: Aug. 13, 2018

(86) PCT No.: PCT/CA2018/050977
§ 371 (c)(1),
(2) Date: Feb. 14, 2020

(87) PCT Pub. No.: WO2019/033203
PCT Pub. Date: Feb. 21, 2019

(65) Prior Publication Data
US 2021/0017585 A1   Jan. 21, 2021

Related U.S. Application Data

(60) Provisional application No. 62/545,081, filed on Aug. 14, 2017.

(51) Int. Cl.
*C12Q 1/6816*  (2018.01)
*C12Q 1/6886*  (2018.01)

(52) U.S. Cl.
CPC ......... *C12Q 1/6816* (2013.01); *C12Q 1/6886* (2013.01); *C12Q 2563/143* (2013.01);
(Continued)

(58) Field of Classification Search
None
See application file for complete search history.

(56) References Cited

U.S. PATENT DOCUMENTS

| | | |
|---|---|---|
| 10,073,079 B2 | 9/2018 | Kelley et al. |
| 10,809,180 B2 | 10/2020 | Kelley et al. |
| 2009/0258076 A1* | 10/2009 | Cheon ............... A61K 49/1875 428/404 |

FOREIGN PATENT DOCUMENTS

| | | |
|---|---|---|
| WO | 2009091643 A1 | 7/2009 |
| WO | WO-2014166000 A1 | 10/2014 |

(Continued)

OTHER PUBLICATIONS

Labib et al. Nature Chemistry. May 2018. 10: 489-495 (Year: 2018).*

(Continued)

*Primary Examiner* — Carla J Myers
(74) *Attorney, Agent, or Firm* — Wilson Sonsini Goodrich & Rosati

(57) ABSTRACT

Methods and systems for mRNA analysis and quantification of mRNA expression in cells are provided. An example method includes introducing a first capture probe and a second capture probe into the cells, the first capture probe and the second capture probe each configured to be complementary to a respective section of target mRNA within the cells, wherein binding of the first and second capture probes to the respective sections of the target mRNA results in tagging of the cells and causes the first and second capture probes to form clusters with each other. The first capture probe and the second capture probe are each bound to magnetic nanoparticles (MNPs) that, when trapped within the tagged cells, cause the tagged cells to be susceptible to (Continued)

magnetic forces. The method and system further include introducing the cells into a device configured to magnetically capture tagged cells.

14 Claims, 45 Drawing Sheets

Specification includes a Sequence Listing.

(52) U.S. Cl.
CPC .. *C12Q 2563/155* (2013.01); *C12Q 2565/629* (2013.01); *C12Q 2600/158* (2013.01)

(56) References Cited

FOREIGN PATENT DOCUMENTS

| WO | WO-2017054075 A1 | 4/2017 |
|---|---|---|
| WO | 2017123697 A1 | 7/2017 |
| WO | WO-2019033203 A1 | 2/2019 |
| WO | WO-2022178643 A1 | 9/2022 |

OTHER PUBLICATIONS

Mousavi et al. Analyst. 2013. 128: 2740 (Year: 2013).*
Acronyms and Slang "What does TEG Stand for in Medical & Science?" available via URL: <acronymsandslang.com/meaning-of/medicine-and-science/TEG.html>, printed on Feb. 6, 2023, 1 page. (Year: 2023).*
Singer Laboratory. "RapidPrep Plasmid DNA Preparation Protocol," available via URL: <singerlab.ucdavis.edu/wp-content/uploads/2020/01/PlasmidMiniPrep-1.pdf>, printed on Feb. 6, 2023, 1 page. (Year: 2023).*
Jo, Younggeun, et al. "Magneyophoretic Sorting of Single Cell-Containing Microdroplets", Mar. 30, 2016.
Brouzes, Eric, et al., "Rapid and continuous magnetic separation in droplet microfluidic devices", Feb. 7, 2015.
Stoffels, Marion, et al., "rRNA probe-based cell fishing of bacteria", Feb. 8, 1999.
Pivetal, Jeremy, et al., "Selective isolation of bacterial cells within a microfluidic device using magnetic probe-based cell fishing", Jan. 27, 2014.
Elowitz, M.B., Levine, A.J., Siggia, E.D. & Swain, P.S. Stochastic gene expression in a single cell. Science 297, 1183-1186 2002.
Bendall, S.C. & Nolan, G.P. From single cells to deep phenotypes in cancer. Nat. Biotechnol. 30, 639-647 2012.
Yu, M. et al. Circulating breast tumor cells exhibit dynamic changes in epithelial and mesenchymal composition. Science 339, 580-584 2013.
Kalinich, M. et al. An RNA-based signature enables high specificity detection of circulating tumor cells in hepatocellular carcinoma. Proc. Natl. Acad. Sci. U.S.A 114, 1123-1128 2017.
Clark, I.C. & Abate, A.R. Finding a helix in a haystack: nucleic acid cytometry with droplet microfluidics. Lab Chip 17, 2032-2045 2017.
Briley, W.E., Bondy, M.H., Randeria, P.S., Dupper, T.J. & Mirkin, C.A. Quantification and real-time tracking of RNA in live cells using Sticky-flares. Proc. Natl. Acad. Sci. U.S.A 112, 9591-95955 2015.
Geiss, G.K. et al. Direct multiplexed measurement of gene expression with color-coded probe pairs. Nat. Biotechnol. 26, 317-325 2008.
Deng, Q., Ramskold, D., Reinius, B. & Sandberg, R. Single-cell RNA-seq reveals dynamic, random monoallelic gene expression in mammalian cells. Science 343, 193-196 2014.
Livak, K.J. et al. Methods for qPCR gene expression profiling applied to 1440 lymphoblastoid single cells. Methods 59, 71-79 2013.
Lyubimova, A. et al. Single-molecule mRNA detection and counting in mammalian tissue. Nat. Protoc. 8, 1743-1758 2018.
Itzkovitz, S. & van Oudenaarden, A. Validating transcripts with probes and imaging technology. Nat. Methods 8, S12-19 2011.
Halo, T.L. et al. NanoFlares for the detection, isolation, and culture of live tumor cells from human blood. Proc. Natl. Acad. Sci. U. S. A. 111, 17104-17109 2014.
Alix-Panabieres, C. & Pantel, K. Challenges in circulating tumour cell research. Nat. Rev. Cancer 14, 623-631 2014.
Carrasco, R.A. et al. Antisense inhibition of survivin expression as a cancer therapeutic. Mol. Cancer. Ther. 10, 221-232 2011.
Wang, S. et al. Potential clinical significance of a plasma-based KRAS mutation analysis in patients with advanced non-small cell lung cancer. Clin. Cancer Res. 16, 1324-1330 2010.
Altieri, D.C. Validating survivin as a cancer therapeutic target. Nat. Rev. Cancer 3, 46-54 2003.
Fulda, S. & Vucic, D. Targeting IAP proteins for therapeutic intervention in cancer. Nat. Rev. Drug Discov. 11, 109-124 2012.
Watson, P.A., Arora, V.K. & Sawyers, C.L. Emerging mechanisms of resistance to androgen receptor inhibitors in prostate cancer. Nat. Rev. Cancer 15, 701-711 2015.
Robinson, D. et al. Integrative clinical genomics of advanced prostate cancer. Cell 161, 1215-1228 2015.
Antonarakis, E.S. et al. AR-V7 and resistance to enzalutamide and abiraterone in prostate cancer. N. Engl. J. Med. 371, 1028-1038 2014.
Tomlins, S.A. et al. Recurrent fusion of TMPRSS2 and ETS transcription factor genes in prostate cancer. Science 310, 644-648 2005.
Tomlins, S.A. et al. Urine TMPRSS2:ERG fusion transcript stratifies prostate cancer risk in men with elevated serum PSA. Sci. Transl. Med. 3, 94ra72 2011.
Labib et al., Single-cell mRNA cytometry via sequence-specific nanoparticle clustering and trapping. Nat Chem.10(5):489-495 (2018).
PCT/CA2018/050977 International Search Report and Written Opinion dated Oct. 29, 2018.

* cited by examiner

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: Probe

<400> SEQUENCE: 1
```
gataaggctt cctgccgcgc                                              20

<210> SEQ ID NO 2
<211> LENGTH: 20
<212> TYPE: DNA
<213> ORGANISM: Artificial sequence
<220> FEATURE:
<223> OTHER INFORMATION: Probe

<400> SEQUENCE: 2
caacgactgg tcctcactca                                              20

<210> SEQ ID NO 3
<211> LENGTH: 45
<212> TYPE: DNA
<213> ORGANISM: Artificial sequence
<220> FEATURE:
<223> OTHER INFORMATION: probe

<400> SEQUENCE: 3
gcgcggcagg aagccttatc agttgtgagt gaggaccagt cgttg                  45

<210> SEQ ID NO 4
<211> LENGTH: 45
<212> TYPE: DNA
<213> ORGANISM: Artificial sequence
<220> FEATURE:
<223> OTHER INFORMATION: Ctrl-TMPRSS2/ERG oligonucleotide

<400> SEQUENCE: 4
gttgctgacc aggagtgagt gttgactatt ccgaaggacg gcgcg                  45

<210> SEQ ID NO 5
<211> LENGTH: 20
<212> TYPE: DNA
<213> ORGANISM: Artificial sequence
<220> FEATURE:
<223> OTHER INFORMATION: Probe

<400> SEQUENCE: 5
gataaggctt cctgccgcgc                                              20

<210> SEQ ID NO 6
<211> LENGTH: 20
<212> TYPE: DNA
<213> ORGANISM: Artificial sequence
<220> FEATURE:
<223> OTHER INFORMATION: Probe

<400> SEQUENCE: 6
caacgactgg tcctcactca                                              20

<210> SEQ ID NO 7
<211> LENGTH: 20
<212> TYPE: DNA
<213> ORGANISM: Artificial sequence
<220> FEATURE:
<223> OTHER INFORMATION: Probe

<400> SEQUENCE: 7
cagttcttga atgtagagat                                              20

<210> SEQ ID NO 8
<211> LENGTH: 20
<212> TYPE: DNA

```
<213> ORGANISM: Artificial sequence
<220> FEATURE:
<223> OTHER INFORMATION: Probe

<400> SEQUENCE: 8
gcaggcgcag ccctccaaga                                                    20

<210> SEQ ID NO 9
<211> LENGTH: 20
<212> TYPE: DNA
<213> ORGANISM: Artificial sequence
<220> FEATURE:
<223> OTHER INFORMATION: Probe

<400> SEQUENCE: 9
tgctttcatg cacaggaatt                                                    20

<210> SEQ ID NO 10
<211> LENGTH: 20
<212> TYPE: DNA
<213> ORGANISM: Artificial sequence
<220> FEATURE:
<223> OTHER INFORMATION: Probe

<400> SEQUENCE: 10
ctggaataat gctgaagagt                                                    20

<210> SEQ ID NO 11
<211> LENGTH: 20
<212> TYPE: DNA
<213> ORGANISM: Artificial sequence
<220> FEATURE:
<223> OTHER INFORMATION: Probe

<400> SEQUENCE: 11
ctgatgaaga gaagcatgtg                                                    20

<210> SEQ ID NO 12
<211> LENGTH: 20
<212> TYPE: DNA
<213> ORGANISM: Artificial
<220> FEATURE:
<223> OTHER INFORMATION: Probe

<400> SEQUENCE: 12
tgggagaaga atgagaggct                                                    20

<210> SEQ ID NO 13
<211> LENGTH: 18
<212> TYPE: DNA
<213> ORGANISM: Artificial sequence
<220> FEATURE:
<223> OTHER INFORMATION: LY2181308 antisense oligonucleotide

<400> SEQUENCE: 13
tgtgctattc tgtgaatt                                                      18

<210> SEQ ID NO 14
<211> LENGTH: 17
<212> TYPE: DNA
<213> ORGANISM: Artificial sequence
<220> FEATURE:
<223> OTHER INFORMATION: Primer

<400> SEQUENCE: 14
caggaggcgg aggcgga                                                       17
```

<210> SEQ ID NO 15
<211> LENGTH: 21
<212> TYPE: DNA
<213> ORGANISM: Artificial sequence
<220> FEATURE:
<223> OTHER INFORMATION: Primer

<400> SEQUENCE: 15
ggcgttgtag ctgggggtga g                                            21

<210> SEQ ID NO 16
<211> LENGTH: 23
<212> TYPE: DNA
<213> ORGANISM: Artificial sequence
<220> FEATURE:
<223> OTHER INFORMATION: Primer

<400> SEQUENCE: 16
ctttctcaag gaccaccgca tct                                          23

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
gcactttctc cgcagtttcc tc                                           22

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
ggaattcctg tgcatgaaag c                                            21

<210> SEQ ID NO 19
<211> LENGTH: 24
<212> TYPE: DNA
<213> ORGANISM: Artificial sequence
<220> FEATURE:
<223> OTHER INFORMATION: Primer

<400> SEQUENCE: 19
cgatcgagtt ccttgatgta gttc                                         24

<210> SEQ ID NO 20
<211> LENGTH: 24
<212> TYPE: DNA
<213> ORGANISM: Artificial sequence
<220> FEATURE:
<223> OTHER INFORMATION: Primer

<400> SEQUENCE: 20
cttgtcgtct tcggaaatgt tatg                                         24

<210> SEQ ID NO 21
<211> LENGTH: 22
<212> TYPE: DNA
<213> ORGANISM: Artificial sequence
<220> FEATURE:

<223> OTHER INFORMATION: Primer

<400> SEQUENCE: 21
ctttcttcag ggtctggtca tt                                    22

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
cggctgttta acttcgcttc                                       20

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
cacacgccaa gaaacagtga                                       20

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
gagtcaacgg atttggtcgt                                       20

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
gacaagcttc ccgttctcag                                       20

<210> SEQ ID NO 26
<211> LENGTH: 20
<212> TYPE: DNA
<213> ORGANISM: Artificial sequence
<220> FEATURE:
<223> OTHER INFORMATION: Probe

<400> SEQUENCE: 26
tgttcagagg tgactggatc                                       20

<210> SEQ ID NO 27
<211> LENGTH: 20
<212> TYPE: DNA
<213> ORGANISM: Artificial sequence
<220> FEATURE:
<223> OTHER INFORMATION: Probe

<400> SEQUENCE: 27
gccctcagcc tgacatgtca                                       20

```
<210> SEQ ID NO 28
<211> LENGTH: 20
<212> TYPE: DNA
<213> ORGANISM: Artificial sequence
<220> FEATURE:
<223> OTHER INFORMATION: Probe

<400> SEQUENCE: 28
ctcagggaca cagggcacgg                                               20

<210> SEQ ID NO 29
<211> LENGTH: 20
<212> TYPE: DNA
<213> ORGANISM: Artificial sequence
<220> FEATURE:
<223> OTHER INFORMATION: Probe

<400> SEQUENCE: 29
agacaatggt ggcatactcc                                               20

<210> SEQ ID NO 30
<211> LENGTH: 20
<212> TYPE: DNA
<213> ORGANISM: Artificial sequence
<220> FEATURE:
<223> OTHER INFORMATION: Probe

<400> SEQUENCE: 30
tctgtagcaa ggaggctgaa                                               20

<210> SEQ ID NO 31
<211> LENGTH: 20
<212> TYPE: DNA
<213> ORGANISM: Artificial sequence
<220> FEATURE:
<223> OTHER INFORMATION: Probe

<400> SEQUENCE: 31
ctgcttcttc agggcttctt                                               20
```

METHOD FOR DETERMINATION OF CELLULAR MRNA

CROSS-REFERENCE TO RELATED APPLICATIONS

The present disclosure claims priority from U.S. provisional patent application No. 62/545,081, filed Aug. 14, 2017, the entirety of which is hereby incorporated by reference.

FIELD

The present disclosure relates generally to a cancer diagnostic tool and method. In particular, the disclosure relates to an amplification-free molecular system and method for mRNA analysis in cells.

BACKGROUND

Gene expression is a stochastic process, and as a result, mRNA levels exhibit heterogeneity even within a population of isogenic cells[1]. Studies of gene expression are typically carried out via bulk transcriptome measurement approaches, where cells are pooled together and their average gene expression is determined. This strategy generates a transcriptional signature for the bulk population of cells. The desire to instead study cellular heterogeneity has motivated the development of assays that are capable of characterizing gene expression at the single-cell level[2].

Most single-cell transcriptional analysis methods are based on RNA sequencing[3], quantitative reverse transcription PCR (RT-qPCR) combined with microfluidics[4,5], or techniques based on fluorescence hybridization[6,7]. Unfortunately, RNA sequencing requires mRNA isolation and pre-amplification using PCR, and this may result in amplification bias as well as a significant loss of transcripts[8]. RT-qPCR combined with microfluidics may provide a closer look at RNA expression within single cells; however, a large percentage of mRNA species can be lost during the purification and processing steps. In addition, the reverse transcription step may introduce artifacts due to template-switching, primer-independent cDNA synthesis, and DNA-dependent DNA polymerase activity[9].

Fluorescence in situ hybridization[10,11] and other techniques based on nanoparticle probes[12] do not require pre-amplification, and several of these methods are semi-quantitative for individual cells analyzed in situ. However, often the target mRNA must be labeled with several fluorescent probes to achieve sufficient signal strength, and this precludes accurate quantitation. Moreover, for the analysis of rare cells such as circulating tumour cells (CTCs), cells must first be captured from whole blood, identified, and then subjected to expression analysis: this introduces uncertainty about how the analysis workflow affects the results obtained.

Measurements at the single cell level are particularly important for the study of cancer cells and tumors. Tumors are inherently heterogeneous: different regions of a tumor may experience different levels of exposure to oxygen, chemotherapeutics and other biochemical factors. CTCs are rare tumour cells shed from primary and metastatic tumor sites into the circulation as viable and apoptotic cells, and may exhibit even greater heterogeneity because of dynamic changes correlated to their presence in the bloodstream[13].

SUMMARY

In various examples disclosed herein, the present disclosure describes techniques that may be used for characterizing gene expression patterns in individual cells. In various examples, an amplification-free molecular approach for mRNA analysis is disclosed, which may be useful for analysis of mRNA in cancer cells. In this approach, a pair of DNA probes (dual probe) specific to the target mRNA is modified with magnetic nanoparticles (MNPs). Dual probe—mRNA hybridization triggers the formation of microscale MNP clusters. The clusters remain strongly localized within cells, thus allowing for on-chip sorting of cells according to their mRNA content, using a device (e.g., a microfluidic device) that is configured for capture of magnetically labelled cells. This approach provides a useful tool for analyzing CTC mRNAs, with minimal cell manipulation and no interference from residual blood cells background.

In some examples, the present disclosure provides a method for mRNA analysis in cells. The method includes: introducing two capture probes into the cells, the first capture probe and the second capture probe each configured to be complementary to a respective section of target mRNA within the cells, wherein binding of the first and second capture probes to the respective sections of the target mRNA results in tagging of the cells and causes the first and second capture probes to form clusters with each other; wherein the first capture probe and the second capture probe are each bound to magnetic nanoparticles (MNPs) that, when trapped within the tagged cells, cause the tagged cells to be susceptible to magnetic forces; and introducing the cells into a device configured to magnetically capture tagged cells.

In some examples, the present disclosure provides a system for analyzing mRNA in cells. The system includes: a first capture probe and a second capture probe, the first capture probe and the second capture probe each configured to be complementary to a respective section of target mRNA within the cells, wherein binding of the first and second capture probes to the respective sections of the target mRNA results in tagging of the cells and causes the first and second capture probes to form clusters with each other; wherein the first capture probe and the second capture probe are each bound to magnetic nanoparticles (MNPs) that, when trapped within the tagged cells, cause the tagged cells to be susceptible to magnetic forces; and a device configured to magnetically capture tagged cells.

In some examples, the present disclosure provides a method for quantifying expression of target mRNA in cells of a sample. The method includes determining an mRNA capture fraction of cells expressing the target mRNA in the sample and calculating an expression index (EI) for expression of the target mRNA in the sample. The EI is calculated by dividing the mRNA capture fraction by an average zone parameter. The average zone parameter represents a zone in which cells having an average expression of the target mRNA is captured by a multi-zoned capture device. Determining the mRNA capture fraction includes magnetically capturing cells that have been tagged with a targeted capture probe bound to a magnetic nanoparticle (MNP). The capture probe is configured to be complementary to a section of the target mRNA.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Cell-to-cell variation in gene expression creates a need for techniques that characterize expression at the level of individual cells. This is particularly true for rare circulating tumor cells (CTCs), in which subtyping and drug resistance are of particular interest. In blood, these heterogeneous cells are outnumbered one-billion-fold by normal cells. As a step towards this end, the present disclosure provides examples of an amplification-free molecular approach for mRNA analysis in cancer cells.

Figure 1:
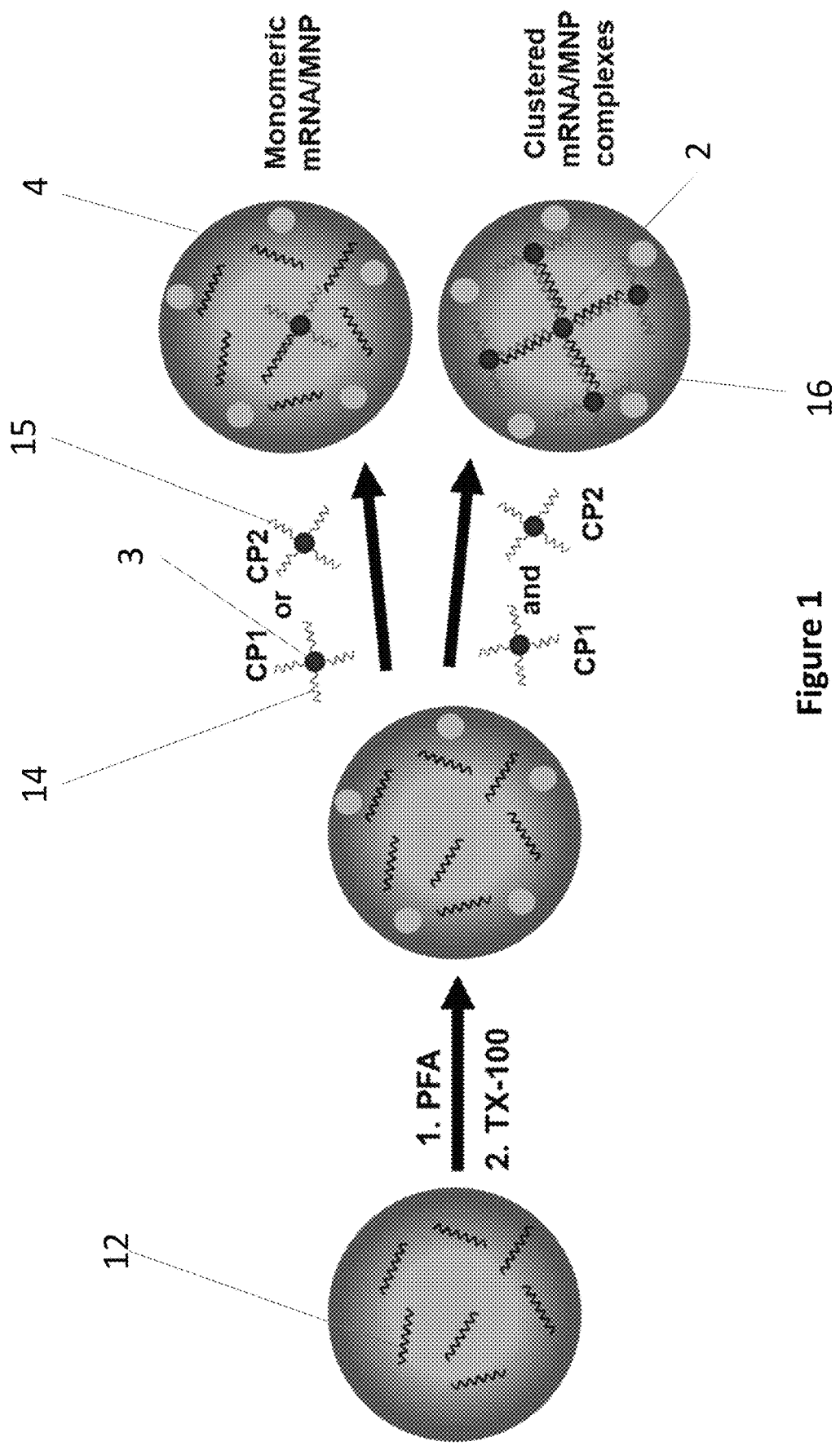
FIG. 1 is a schematic representation of the cellular mRNA determination approach.

Reference is first made to FIG. 1. An embodiment of the disclosed approach relies on targeting a cellular mRNA 12 within a cell 4 with a dual probe 14, 15 (described further below), subsequent to cell fixation and permeabilization. Each probe 14, 15 includes respective DNA strands complementary to respective sections of the target mRNA 12 and the DNA strands of the probes 14, 15 are tagged with magnetic nanoparticles (MNPs) 3 at one end.

Cells 4 are permeabilized to deliver probes with attached magnetic nanoparticles 3. In the presence of the target mRNA, the probes 14, 15 form clusters 2 which are too large to exit the cell 4. The probes 14, 15 are thus trapped within the cells 4 when clustering 2 occurs in the presence of the target mRNA. This traps the MNPs 3 of the probes 14, 15 within the cells 4, which increases the magnetic susceptibility of the cells 4. A microfluidic device 6 (discussed further below) may then be used to magnetically capture the tagged cells 4. Although a microfluidic device 6 is described as an example for magnetically capturing the tagged cells 4, it should be understood that any suitable device (e.g., using a microfluidic approach or non-microfluidic approach) may be used for magnetic capture of the tagged cells 4. For example, simply applying an appropriate magnetic force to attract the tagged cells 4 (e.g., by placing a simple magnet against the side of a container containing the tagged cells 4) and then washing away non-attracted particles may be sufficient.

In an embodiment, clustering 2 occurs when target mRNA is present. Dual Probe-mRNA hybridization 16 triggers the aggregation of MNPs to form clusters 2 that become trapped within the cells 4, as shown schematically in FIG. 1. That is, binding of the respective DNA strands of the probes 14, 15 to respective sections of the target mRNA 12 results in the probes 14, 15 being joined to each other via the target mRNA 12. The formed clusters 2 enhance the magnetic susceptibility of the cells 4 and prevent the leakage of the probes 14, 15.

In one example, in the absence of the target mRNA, no clusters 2 are formed and the probes can exit the cells 4. In this example, even when some unclustered probes 14, 15 remain in the cell 4, they cause only a small increase in the magnetic susceptibility (compared to magnetic clusters 2). Thus, non-target cells 4 do not exhibit enhanced magnetic susceptibility and are not magnetically captured when introduced to the microfluidic device 6.

In the example illustrated, cells 4 are fixed with 4% paraformaldehyde (PFA) and permeabilized with 0.3% Triton X-100 (TX-100). The cells 4 are incubated with two magnetic nanoparticles (MNPs)-tagged DNA probes 14 and 15 complementary to different sections of the target mRNA. Other methods for introducing the probes 14 and 15 into the cells 4 may also be suitable.

Figure 2:
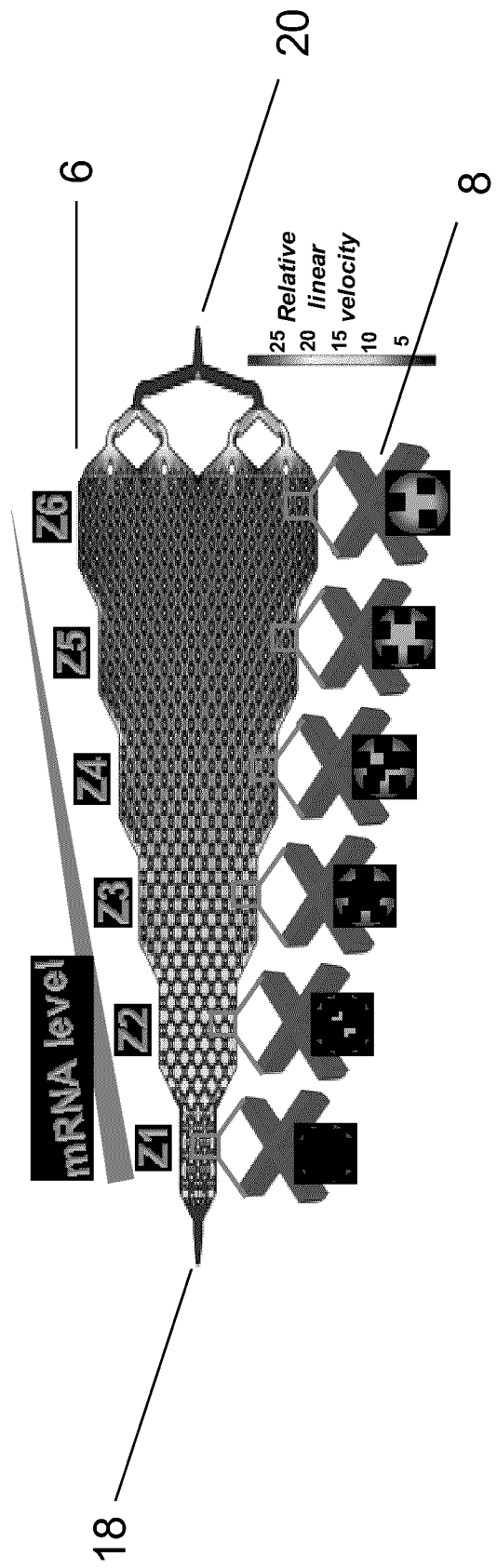
FIG. 2 is a diagram of an embodiment of a microfluidic device used for the purpose disclosed in connection with FIG. 1.

The tagged cells 4 are loaded into a microfluidic device 6 with a flow inlet 18 for receiving a sample, as shown in FIG. 2, where cells flow from inlet 18 towards flow outlet 20. In this example, the tagged cells 4 are captured within a six-zone fluidic device 6 that features zones or sorting portions (discussed further below), each zone containing X-shaped microfabricated structures 8 to create localized subzones of low flow velocity and favorable capture dynamics (FIG. 2). A six-zone device was used in examples described herein, as results from a 6-zone device were found to be suitable for the various experiments discussed further below. However, a device with more than six zones or fewer than six zones may be used.

An example of the microfluidic device 6 is further described in United States patent application publication no. 2016/0061811, which is hereby incorporated by reference.

Generally, cell capture occurs when the magnetic force acting on the cell counterbalances the drag force caused by the flow. The magnetic force acting on cells tagged with magnetic nano-beads can be calculated according to the following formula:

$$\vec{F}_m = N_b V_m \frac{\Delta \chi_{bead}}{\mu_0} (\vec{B} \cdot \nabla) \vec{B}$$

Where $N_b$ is the number of beads per cell, $V_m$ is the bead volume, $\Delta X_{bead}$ [unitless] represents the difference between the magnetic susceptibility of the bead and the medium, po [H/m] is the permeability of free space ($4\pi \times 10^{-7}$ H/m), and B [T] is the applied magnetic field. In some examples described below, magnetic beads with diameter of 100 nm were used.

Stokes' law can be used to determine the transverse drag force acting on a cell, neglecting wall effects at low Reynolds numbers, according to the following formula:

$$\vec{F}_d = -6\pi \eta r \vec{v}$$

Where r [m] is the cell radius (10 μm), η[Pa×s] is the dynamic viscosity of the medium (0.001 Pa×s), and v [m/s] is the velocity of the cell.

FIG. 2 further shows the design of six sequential zones that feature different average linear velocities (for example, 1×, 0.47×, 0.31×, 0.23×, 0.18×, 0.15×) to facilitate capturing cells with different magnetic content. Zone 1 is closest to inlet 18, as shown in FIG. 2.

In one example, the first zone Z1 (that is, the zone Z1 closest to the inlet) may be designed to have a relatively high linear velocity that would only retain particles (e.g., cells) with relatively high susceptibility to attractive forces (in this case, a high magnetic content, meaning, a high number of trapped probes within the cell). The following zones Z2-Z6 may be designed to have velocities that decreased stepwise, for example, by the factors described above. That is, the first zone Z1 closest to inlet 18 has a relatively high average linear velocity of about 500 μm/s (indicated as 1×), the second zone Z2 has an average linear velocity that is 0.47× of that in the first zone Z1, the third zone Z3 has an average linear velocity that is 0.31× of that in the first zone Z1, the fourth zone Z4 has an average linear velocity that is 0.23× of that in the first zone Z1, the fifth zone Z5 has an average linear velocity that is 0.18× of that in the first zone Z1, and the sixth zone Z6 has an average linear velocity that is 0.15× of that in the first zone Z1.

The average linear velocity of about 500 μm/s in the first zone Z1 is provided as an example, and higher or lower linear velocities may be selected based on the sample being analyzed, for example. The stepwise decrease of linear velocity is provided as an example, and other changes to linear velocity across the zones including increase or decrease by other factors, may be suitable. Generally, the microfluidic device 6 may be designed such that the average linear velocities decrease from the inlet 18 to the outlet 20.

With further reference to FIG. 2, cells with high magnetic content (and a high number of probes) are captured in the first zone, which has a high linear velocity and thus retains cells with high magnetic content since the retaining magnetic force overcomes the drag force created by the locally high flow velocity. The first zone captures only the cells with magnetic content that is sufficiently high to overcome the drag force. The following five zones exhibit gradually reduced linear velocities. Cells with medium to low magnetic content are captured in later zones. The higher number of probes trapped in the cell means greater magnetic content, and further higher number of trapped probes means greater number of target mRNA in the cell.

Figure 7:
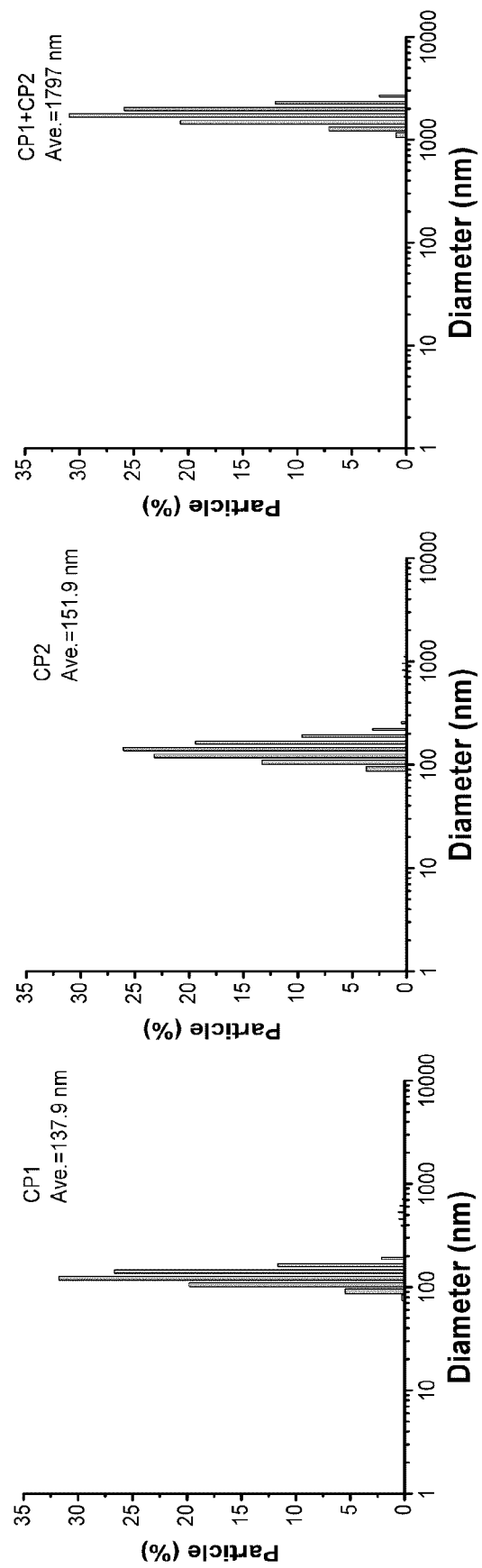
FIG. 7 shows graphs of an example dynamic light scattering (DLS) for capture probe 1 and 2 incubated with a model target sequence. A synthetic TMPRSS2/ERG was incubated with CP1, CP2, and CP1+CP2.
Figure 36:
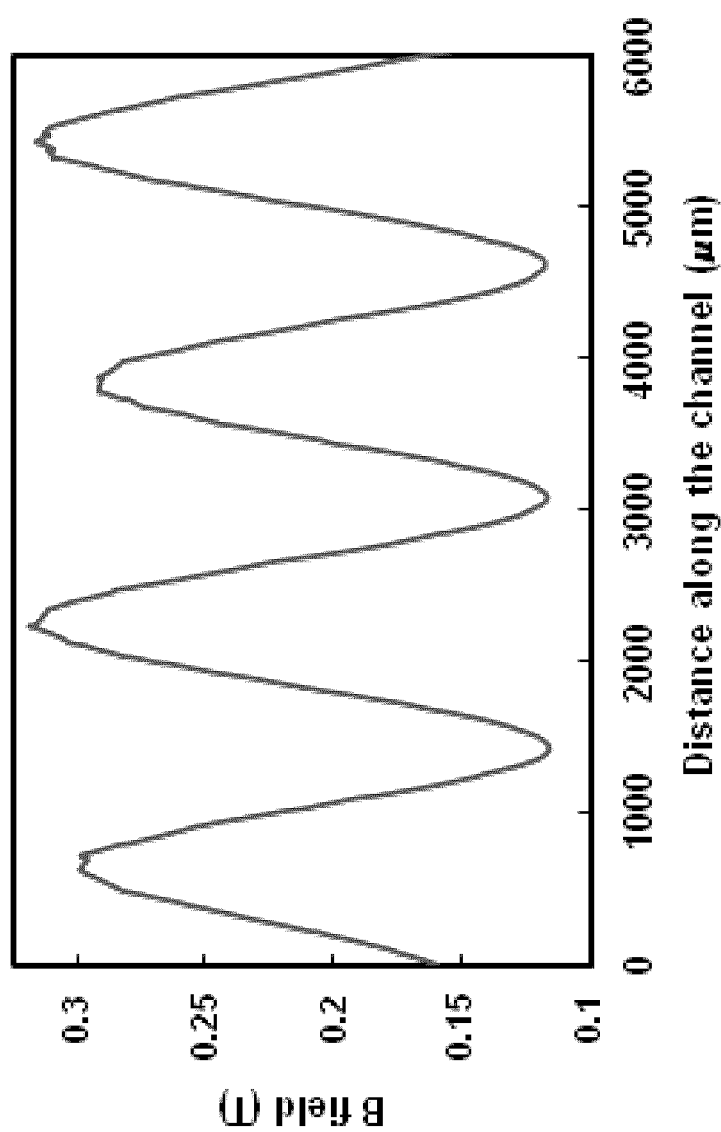
FIG. 36 is a chart illustrating an example magnetic field inside a channel of an example microfluidic device, as a function of distance and at a height of 10 µm.
Figure 37:
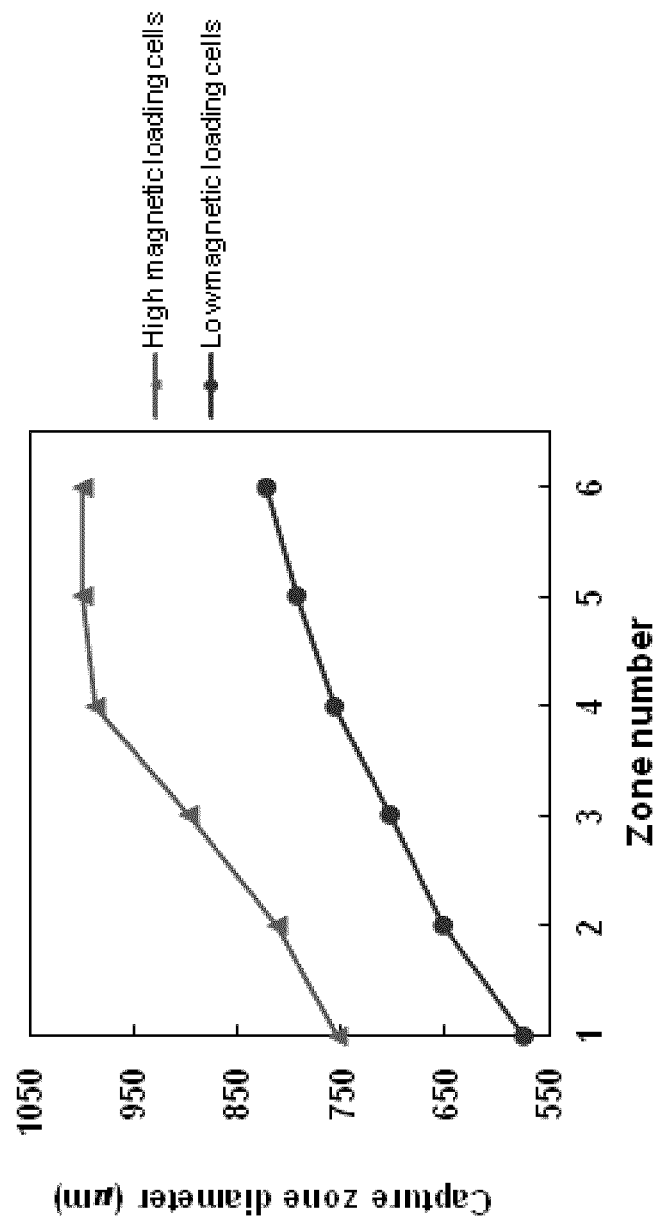
FIG. 37 is a chart illustrating an example of capture zone diameter versus zone number at a height of 10 µm, in an example microfluidic device.

Magnetic and flow field simulations may be used to determine the positions in which cells with variable levels of magnetic content are expected to be captured. The simulations were carried out using COMSOL Multiphysics software (Comsol Inc., US) in order to compare the magnitude of the magnetic force at each zone within the device with the drag force opposing cell capture. FIG. 36 shows example simulation results of a magnetic field, as a function of distance along the channel and at a height of 10 μm, inside a channel of the microfluidic device 6. FIG. 7 shows example simulation results of the diameter of a capture zone versus zone number, at a height of 10 μm, in the microfluidic device 6. It may be noted that the diameter of the capture region increases with decreasing average flow velocity along the device 6. The capture zone diameters for cells with high and low magnetic content are shown in FIG. 37 at a flow rate of 600 uL h$^{-1}$. Any region is considered a "capture zone" when the magnitude of magnetic force acting on the cell is comparable to the drag force.

Figure 38:
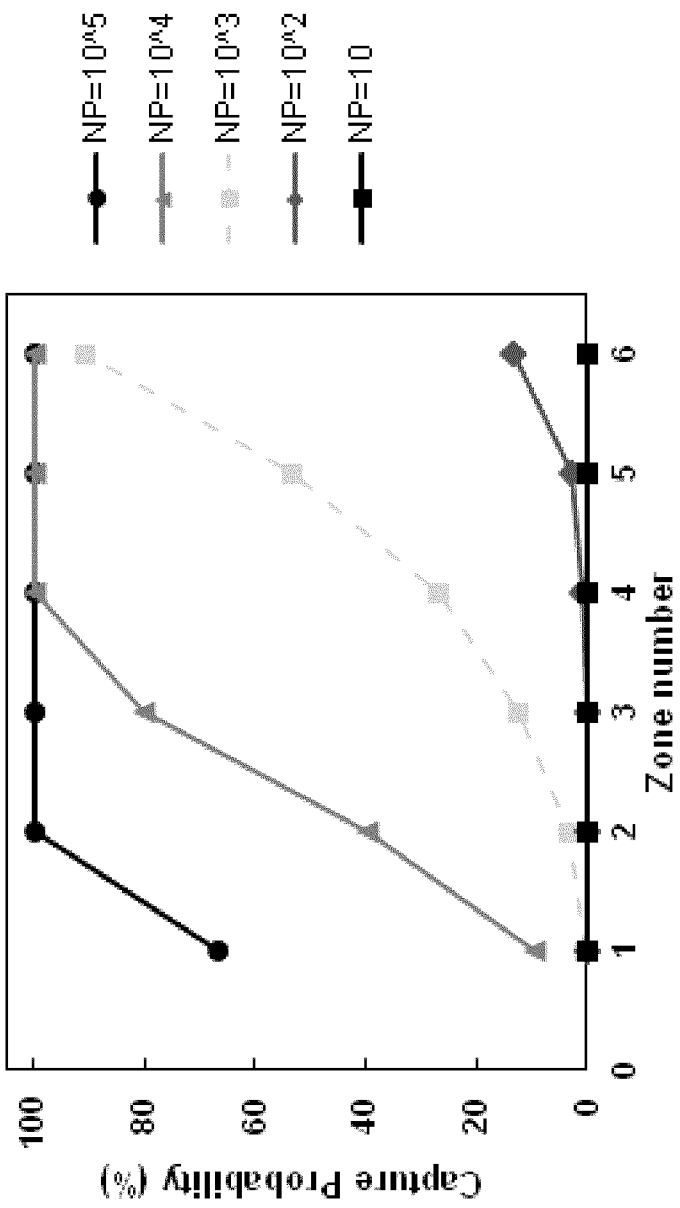
FIG. 38 is a chart illustrating example capture probability of cells having different levels of magnetic content, using an example microfluidic device, at a flow rate of 600 µL h$^{-1}$.

In order to quantify the capture probability of cells, it may be assumed that cells would be captured when they flow within the capture radius along the device 6, whereas cells flowing away from the capture radius will continue their journey along the device. The percentage of the cells that traversed the device within a given radial distance from the centre of an X-structure may then be determined. Additional flow simulations were carried out using a series of concentric control surfaces for various radial positions from the centre of the X-structures. The positive volume flux crossing the capture zone was determined by integrating the dot product of the velocity vector at the surface with the surface unit normal vector over the capture zone area. The amount of fluid changeover at a given radial position from the center of an X-structure was calculated. The positive volume flux crossing the capture zone of cells having different levels of magnetic content (numbers of magnetic nanoparticles=$10^5$, $10^4$, $10^3$, $10^2$, and 10) at different zones were calculated to determine the capture probability of cells within the device. FIG. 38 shows the example calculated capture probability of cells having different levels of magnetic content. All simulations were carried out at the flow rate of 600 μL h$^{-1}$.

Figure 39:
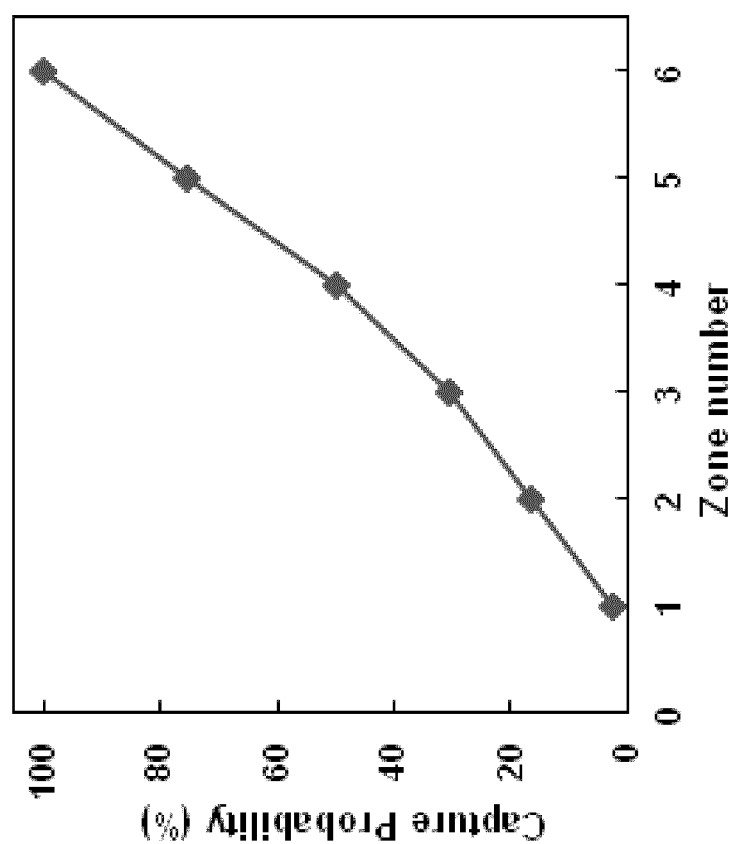
FIG. 39 is a chart illustrating example capture probability of cells having low levels of magnetic loading, using an example microfluidic device, at a reduced flow rate of 50 µL h$^{-1}$.

It is evident from FIG. 38 that cells with different levels of magnetic loading, and thus different levels of mRNA expression, are captured within different zones of the device. In order to show the capability of the device for capturing cells with low magnetic loading, cell capture inside the device was simulated for cells having 100 magnetic nanoparticles at a low flow rate (50 μL h$^{-1}$). As shown in FIG. 39, the microfluidic device was able to retain low magnetic loading cells with a probability of 100% when the flow rate was reduced to 50 μL h$^{-1}$.

Figure 3:
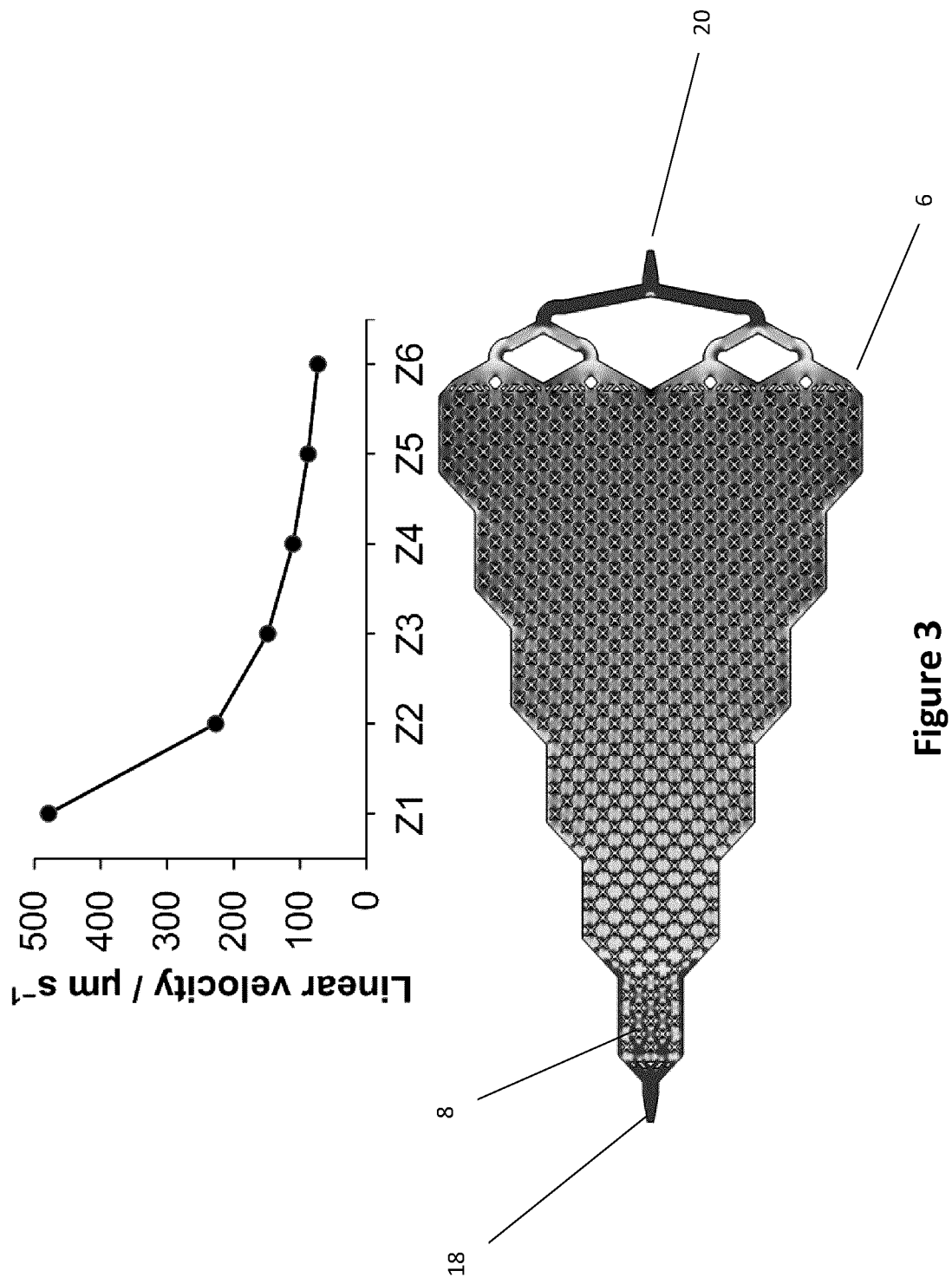
FIG. 3 is a graph and graphical representation of the spatial distribution of linear velocities within the device of FIG. 2.

FIG. 3 shows an example of the spatial distribution of linear velocities within an example of the 6-zone microfluidic device 6 at an example flow rate of 600 μL h$^{-1}$ (1×) at the inlet 18. The top of FIG. 3 is an example graph of the spatial distribution of linear velocities, and the bottom of FIG. 3 is a diagram of the example device 6 corresponding to the flow of cells from zone Z1 to zone Z6. Cells are received at the inlet 18 and flow from the inlet 18 toward the outlet 20.

Figure 4:
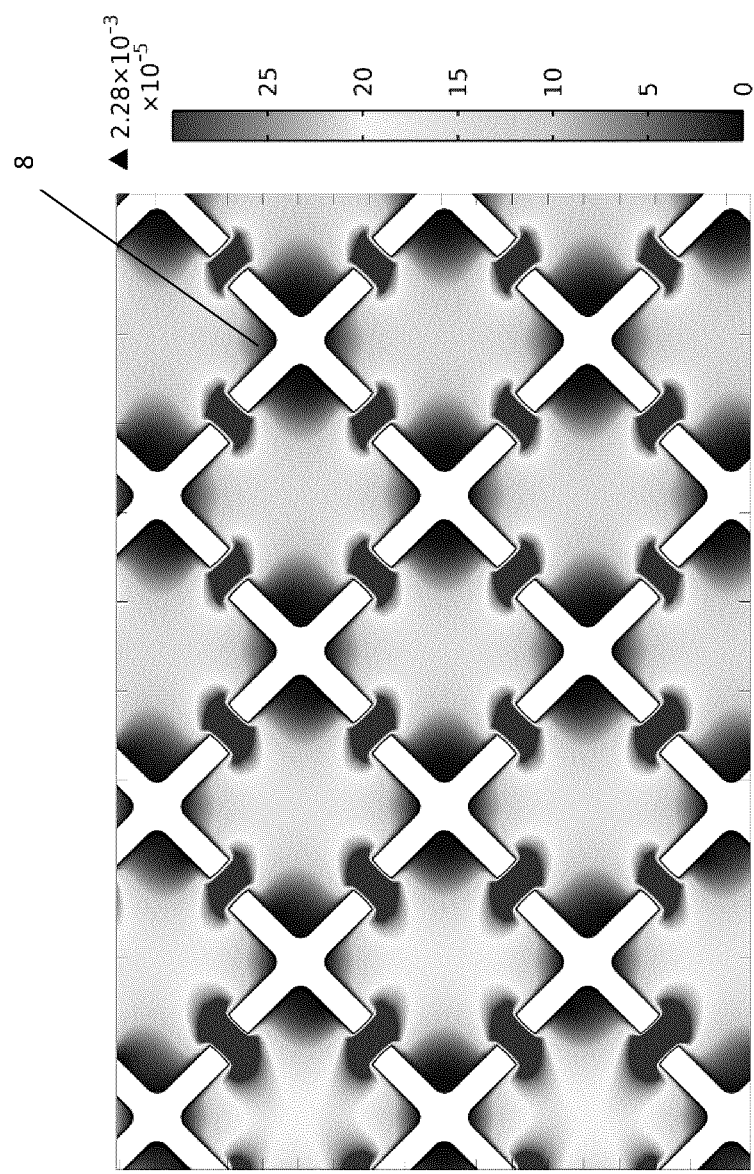
FIG. 4 is a diagram of the spatial distribution of linear velocities within the first zone of the device of FIG. 2.

The linear velocity distribution within the first zone, in an example of the 6-zone microfluidic device 6, is shown in FIG. 4. FIG. 4 shows the spatial distribution of linear velocities within the first zone at a flow rate of 600 μL h$^{-1}$. This design allows cells with high magnetic content (i.e., high expression of the particular target mRNA) to be captured in the first zone, whereas cells with lower mRNA expression continue their journey and become captured in later zones based on their mRNA level.

Figure 5:
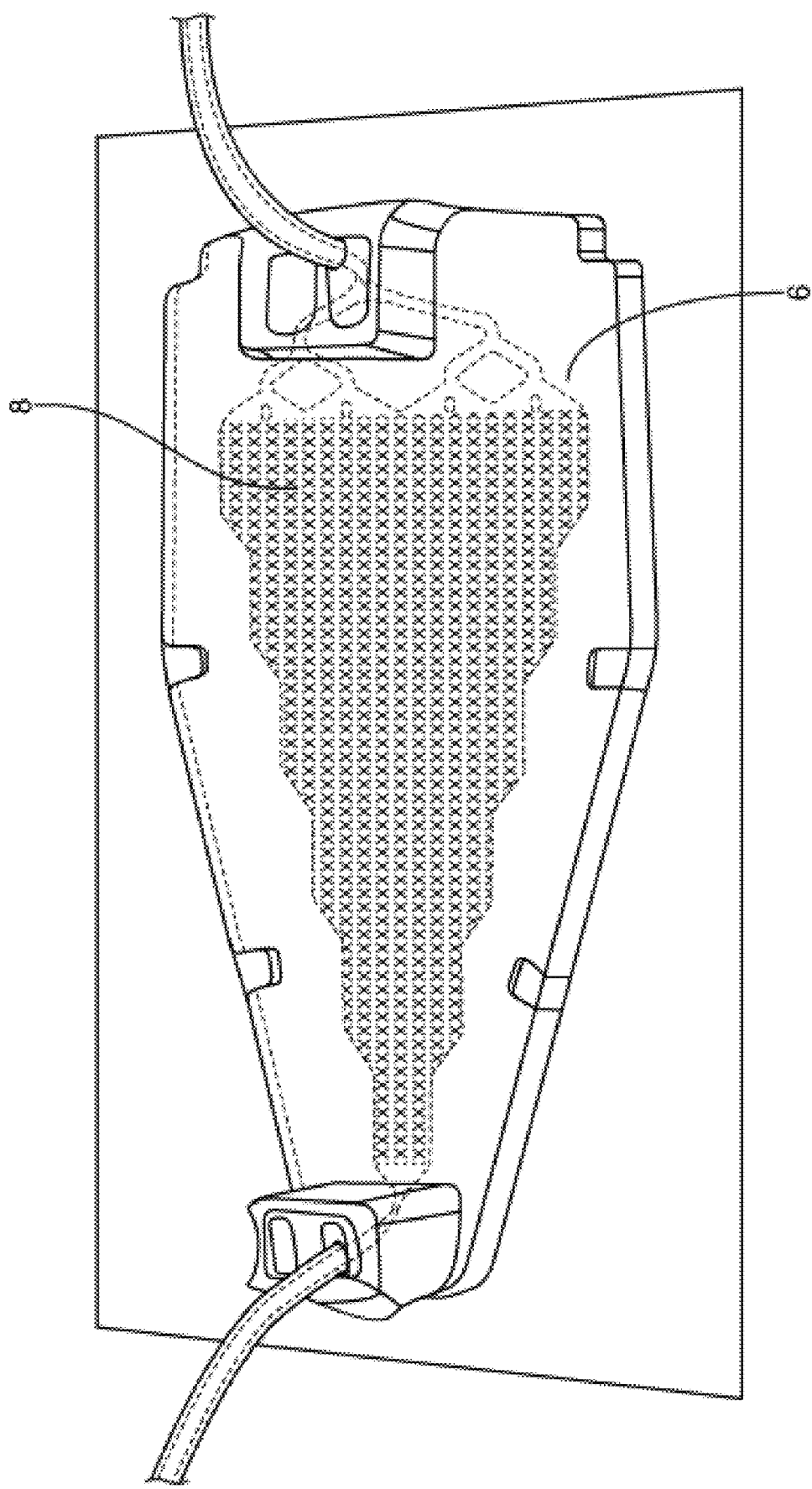
FIG. 5 is a top view of the workstation setup using the device of FIG. 2.

FIG. 5 is a top view of the example workstation setup for cellular mRNA determination, using an example of the 6-zone microfluidic device 6. Two arrays of magnets are positioned on the upper and lower sides respectively of the device to capture cells containing trapped clusters of magnetic nanoparticles.

An example method for fabrication of a microfluidic device is now discussed. The example microfluidic device 6 was fabricated using Poly(dimethoxysilane) (PDMS, Dow Chemical, US) soft-lithography. Masters were fabricated on silicon substrates and patterned in SU-8 3050 (Microchem, US). PDMS replicas were poured on masters and baked at 67° C. for 45 min. After peeling the replicas, holes were pierced to connect the tubing. PDMS replicas were attached to no. 1 glass cover slips using a 30 second plasma treatment and left to bond overnight. This step allows for enhancing the bonding and making it irreversible by oxidizing both the replica and the cover in plasma discharge. Afterward, the silicon tubing was attached to the inlet 18 and outlet 20 of the device. Prior to use, devices were conditioned with 1% Pluronic F68 (Sigma-Aldrich, US) in phosphate-buffered saline (PBS) for 1 h, to reduce the nonspecific adsorption. Each device was sandwiched between two arrays of N52 Nd FeB magnets (K&J Magnetics, US, 1.5 mm by 8 mm) with alternating polarity. A syringe pump (Chemyx, US) was used for the duration of the cell capture process. Other methods for fabricating the microfluidic device may be suitable, for example as discussed in United States patent application publication no. 2016/0061811.

An example method for cell culture is now discussed. VCaP cells (ATCC CRL-2876) were cultured in Dulbecco's Modified Eagle's Medium (DMEM, ATCC 30-2002). PC3 cells were cultured in F-12K Medium (ATCC 30-2004). LNCaP cells were cultured in RPMI-1640 medium (ATCC 30-2001). All media were supplemented with 10% FBS and 1% penicillin-streptomycin and cells were cultured at 37° C. and 5% $CO_2$ in T75 flasks. Cells were harvested when they reached more than 70-80% confluence. Cell detachment from the culture dishes was performed using 1 mL of 0.25% (w/v) Trypsin-0.53 mM EDTA solution for 3 min at 37° C. The cells were then filtered using a 40 μm BD falcon cell strainer (Becton, Dickinson and Company, US).

An example method for preparation of the magnetic nanoparticles-labeled capture probes is now discussed. Briefly, 100 μL of 20 μM of the antisense oligonucleotide solution in Dulbecco's phosphate-buffered saline (DPBS, Sigma-Aldrich, US) were heated for 5 min at 60° C. for deaggregation. Afterward, the solution was transferred to a microtitre plate and incubated with 1.5 μL of 10 mg mL$^{-1}$ streptavidin-coated magnetic nanoparticles (100 nm, Chemicell, US) for 30 min at room temperature. Subsequently, the magnetic nanoparticles-labeled capture probes (MNPs-CPs) were pelleted using a magnetic-ring stand (Thermofisher Scientific, US) and washed three times with DPBS solution.

An example method for cellular mRNA analysis is now discussed. Prostate cancer cell lines (200 cells in 100 μL DPBS) were fixed with 100 μL of 8% paraformaldehyde (PFA, Sigma-Aldrich, US) solution in DPBS containing 1 mM dithiothreitol (DTT, Sigma-Aldrich, US) for 15 min at 37° C. After centrifugation and discarding the supernatant, 100 μL of 0.3% Triton X-100 (TX-100, Sigma-Aldrich, US) in DPBS/DTT were added and the suspension was incubated for 10 min at room temperature. Then, 100 µL of MNPs-labeled CP1 14 and MNPs-labeled CP2 15 in DPBS/DTT (prepared in the previous step) were added and the suspension was gently shaken for 3 h at room temperature.

To account for the cells captured as a result of non-specifically internalized MNPs, cells from a second sample of the same size were captured within another fluidic device using two MNPs-tagged nonspecific DNA probes. A control experiment was carried out in which the cells were gently shaken with the MNPs-labeled nonspecific dual probe (NSP) for 3 h at room temp, subsequent to cell fixation and permeabilization.

To account for the total number of cells analyzed, cells from a third sample of similar size were captured within another device by targeting a specific extracellular marker. The epithelial cell adhesion molecule (EpCAM) was selected as a surface marker commonly expressed in CTCs and subsequently captured using MNPs-tagged anti-EpCAM. Another control experiment was carried out in which the cells were gently shaken with MNPs-anti-EpCAM for 3 h at room temperature. Finally, the cells were loaded into the microfluidic device 6 at a flow rate of 600 µL h$^{-1}$.

The captured cancer cell subpopulations were then immunostained with antibodies specific to EpCAM and cytokeratin (CK) to identify epithelial cells in blood, and to CD45 to differentiate between WBCs and cancer cells. The cells were also stained with 4',6-diamidino-2-phenylindole (DAPI) to identify nucleated cells. Only EpCAM$^+$/CK$^+$/DAPI$^+$/CD45$^-$ are counted as cancer cells.

The mRNA capture fraction is calculated from the following formula:

$$\text{mRNA capture fraction} = (N_{CP} - N_{NSP})/N_{Ab}$$

$N_{CP}$ denotes the number of cancer cells captured using the capture probe, $N_{NSP}$ represents the number of cells captured by the nonspecific probe, and $N_{Ab}$ is the total number of cells in the sample captured by anti-EpCAM. The percentage of cells captured in each zone is multiplied by the mRNA capture fraction to demonstrate the distribution of cell populations bearing different mRNA expression levels and generate a normal distribution fit from which the average capture zone (Zone$_{Ave}$) is determined.

A unique mRNA expression index ($EI_{mRNA}$) can then be calculated from the following formula:

$$EI_{mRNA} = (\text{mRNA capture fraction})/\text{Zone}_{Ave} * 10$$

If the $EI_{mRNA}$ metric is low then there is a corresponding low quantity of the target mRNA present in the cell. Conversely if the metric is high then there is a corresponding large quantity of the target mRNA present in the cell.

An example method for cell staining and imaging is now discussed. Captured cells were counted using fluorescence microscopy. Prior to staining, captured cells were fixed inside the fluidic device using 100 µL of 4% PFA in DPBS/DTT followed by 100 µL of 0.2% TX-100 in DPBS/DTT for permeabilization. Captured cells were immunostained with a mixture of 3% allophycocyanin-labeled anti-cytokeratin antibody (APC-CK, GTX80205, Genetex, US), 3% APC-labeled anti-EpCAM antibody (APC-EpCAM, Miltenyi Biotec Inc., US), and 3% alexafluor 488-labeled anti-CD45 antibody (AF488-CD45, MHCD4520, Invitrogen, US) in 100 µL PBS containing 1% bovine serum albumin (BSA, Sigma-Aldrich, US) and 0.1% Tween-20 (Sigma-Aldrich, US). Immunostaining was carried out for 60 min at a flow rate of 100 µL h$^{-1}$. After washing with 0.1% Tween-20 in PBS, the cells were stained with 1 drop of 4',6-diamidino-2-phenylindole (DAPI Prolong Gold nuclear stain, Invitrogen, US) in 100 µL PBS for 10 min at a flow rate of 600 µL h$^{-1}$. After staining, the cells were washed with 0.1% Tween-20 in PBS, and stored at 4° C. Finally, chips were scanned using a Nikon Ti-E Eclipse microscope with an automated stage controller and a CMOS Camera (Andor Neo). The blue channel was used for DAPI staining, with a typical exposure time of 10-20 ms. The green channel was used for the AF488-CD45 staining, with a typical exposure time of 40-60 ms. The red channel was used for the APC-CK and APC-EpCAM staining, with a typical exposure time of 200-300 ms. The exposure time was set individually for each chip and kept constant in the course of scanning. The imaging was qualitative in nature and hence the variation of exposure time between chips did not affect the results. Cells were counted by overlaying the bright field, red, blue, and green fluorescent images.

An example method for performing transmission electron microscopy (TEM) is now discussed. PC3 cells (10 000 cells in 100 µL) were fixed with 100 µL of 8% PFA in DPBS/DTT for 15 min at 37° C. After centrifugation, 200 µL of 0.3% TX-100 in DPBS/DTT were added and the suspension was incubated for 10 min at room temperature. The cells were gently shaken with either MNPs-labeled CP1-survivin or MNPs-labeled survivin-CP2 or a combination of MNPs-labeled CP1-survivin and MNPs-labeled survivin-CP2 in DPBS/DTT for 3 h at room temperature. The cells were centrifuged for 5 min at 8000 r.p.m. and the supernatant was discarded. The cells were fixed with a solution of 4% PFA and 1% glutaraldehyde in 0.1 M phosphate buffer (pH 7.2) for 1 h at room temperature. After washing three times with the same buffer, the cells were post-stained with 1% osmium tetroxide in 0.1 M phosphate buffer (pH 7.2) for 1 h at room temperature. After washing two times with the same buffer, the cells were dehydrated with 25% ethanol (2 changes in 15 min), 50% ethanol (2 changes in 20 min), 70% ethanol (2 changes in 30 min), 90% ethanol (2 changes in 45 min), and 100% ethanol (3 changes in 60 min). The cells were gently shaken with a mixture of EPON resin and 100% ethanol (1:2) for 2 h, then (2:1) for 3 h, and finally with 100% EPON resin overnight at room temperature. The next day, the resin was removed and the cells were gently shaken with fresh EPON resin for 2 h at room temp then the resin was allowed to polymerize in plastic dishes for 48 h at 40° C. The samples were sliced into 70-90 µm sections with an ultracut microtome then loaded onto carbon-coated copper grids and left to dry at room temperature. TEM (Hitachi H-7000) equipped with XR60 CCD camera was used to examine the morphology of the cells and internalized MNPs.

An example method for performing transfection of PC3 cells is now discussed. Before transfection, PC3 cells (3×10$^4$/well) were grown at a 65% to 75% density overnight in a 6-well plate. After 24 h, the cells were washed with DPBS twice and transfected with 50 µM LY2181308[14] in 2 mL serum-free F-12K medium containing 40 µL lipofectin reagent (Thermofisher Scientific, US) for 6 h at 37° C. A control experiment was carried out in which the cells were incubated with 2 mL serum-free F-12K medium containing 40 µL lipofectin reagent. The medium was removed after 6 h and the cells were incubated with F-12K medium containing 10% FBS for 48 h at 37° C.

An example method for performing reverse transcription-quantitative polymerase chain reaction (RT-qPCR) is now discussed. Total RNA was isolated from cultured cells by Triazol reagent (Invitrogen, US) and used for RT-qPCR as described previously1[5]. The isolated RNA was used for cDNA synthesis using the first strand DNA synthesis kit (Invitrogen, US), which contained random hexamer primers and Superscript III reverse transcriptase, according to the manufacturer's protocol. A comparative Ct experiment was performed on ViiA™ 7 real-time PCR (Life Technologies, US). The following TaqMan probes were used: TMP/ERG (TMP-ERG_CDU62RE), BIRC5 or survivin (Hs04194392_s1), AR-FL (AR-FL_CDRWEKJ), AR-V7 (Hs04260217_m1), and TBP (Hs99999910_m1) as a housekeeping gene control. The assay was carried out in triplicates using 10 ng cDNA for each sample in a 96-well plate. The 10 µL reaction mix included 5 µL 2× TaqMan gene expression master mix (Life Technologies, US), 0.5 µL of 20× assay, 3.5 µL water and 1 µL of 10 ng µL$^{-1}$ cDNA. Cycling conditions for the qPCR were 95° C. for 10 min, followed by 40 cycles of 95° C. for 15 s and 60° C. for 1 min.

An example method for cellular determination of survivin mRNA in blood spiked with prostate cancer cells is now discussed. Fifteen and fifty PC3 cells were spiked into 1 mL of blood, each-at-a-time. The mononuclear cells were isolated using Ficoll method and were subsequently suspended in 250 µL of 2% FBS solution in PBS. Anti-CD15 antibody was modified with MNPs by incubating 100 µL of 40 µg µL$^{-1}$ biotin-tagged anti-CD15 antibody (Abcam, US) in PBS with 6 µL of 10 mg mL$^{-1}$ streptavidin-coated MNPs for 30 min at room temp. The modified MNPs were pelleted using a magnetic-ring stand and washed three times with PBS. The beads were gently shaken with the cell suspension for 30 min at room temp. The captured leukocytes were pelleted using a magnetic separation rack (Thermofisher Scientific, US) and the supernatant was collected for further analysis. The supernatant was incubated with 250 µL of 8% PFA in DPBS/DTT for 15 min at 37° C. After centrifugation, the cells were incubated with 100 µL of 0.3% TX-100 in DPBS/DTT for 10 min at room temp. The cells were gently shaken with 100 µL of DPBS/DTT containing MNPs-labeled CP1-survivin and MNPs-labeled survivin-CP2 in DPBS/DTT for 3 h at room temp. A control experiment was carried out in which the cells were gently shaken with the MNPs-labeled nonspecific dual probe (NSP) for 3 h at room temp, subsequent to cell fixation and permeabilization. Another control experiment was carried out in which the cells were gently shaken with MNPs-anti-EpCAM for 3 h at room temp. The cells were loaded into the 6-zone microfluidic device at a flow rate of 600 µL h$^{-1}$ and subsequently stained with APC-labeled anti-EpCAM, APC-labeled anti-CK antibodies, AF488-labeled anti-CD45 antibody, and DAPI.

An example method for cellular TMPRSS2/ERG mRNA determination in CRPC patient's blood is now discussed. Metastatic castration-resistant prostate cancer (CRPC) patients were recruited from the Princess Margaret Hospital according to the University of Toronto Research Ethics Board approval protocol. All patients were enrolled subsequent to informed consent. Sixteen milliliters of peripheral blood samples were collected from CRPC patients in CellSearch tubes containing EDTA. All the samples were analyzed within 24 h after collection. A set of patient samples (n=4) were analyzed to determine whether the approach would be suitable for the analysis of CTCs mRNA. Sixteen milliliters of blood were split into four tubes to be further utilized for the determination of $N_{CP}$, $N_{NSP}$, and $N_{Ab}$ using the microfluidic approach and for RT-qPCR analysis. The mononuclear cells were isolated using Ficoll method and were subsequently suspended in 250 µL of 2% FBS solution in PBS. Anti-CD15 MNPs were gently shaken with the cell suspension for 30 min at room temp. The captured leukocytes were pelleted using a magnetic separation rack and the supernatant was collected for further analysis. In the first tube, the supernatant was incubated with 250 µL of 8% PFA in DPBS/DTT for 15 min at 37° C. After centrifugation, 100 µL of 0.3% TX-100 in DPBS/DTT were added and the suspension was incubated for 10 min at room temp. The cells were gently shaken with 100 µL of DPBS/DTT containing MNPs-labeled CP1-TMP/ERG and MNPs-labeled TMP/ERG-CP2 in DPBS/DTT for 3 h at room temp. In the second tube, a control experiment was carried out in which the cells were gently shaken with the MNPs-labeled nonspecific dual probe (NSP) for 3 h at room temp, subsequent to cell fixation and permeabilization. In the third tube, another control experiment was carried out in which the cells were gently shaken with MNPs-anti-EpCAM (without prior fixation or permeabilization) for 3 h at room temp. The cells were loaded into the 6-zone microfluidic device at a flow rate of 600 µL h$^{-1}$ and subsequently stained with APC-labeled anti-EpCAM, APC-labeled anti-CK antibodies, AF488-labeled anti-CD45 antibody, and DAPI. In the fourth tube, the cells were gently shaken with MNPs-anti-EpCAM (without fixation or permeabilization) for 1 h at room temp. The cells were loaded into a cell-extraction microfluidic device[44] at a flow rate of 8 mL h$^{-1}$. After washing, the Tygon tubing connecting the zones were cut and the cells were gently pipetted out the device and stored at −80° C. before RT-qPCR analysis.

An example method for cellular AR-V7 mRNA determination in CRPC patient's blood is now discussed. Metastatic castration-resistant prostate cancer (CRPC) patients were recruited from the Princess Margaret Hospital according to the University of Toronto Research Ethics Board approval protocol. All patients were enrolled subsequent to informed consent. Sixteen milliliters of peripheral blood samples were collected from CRPC patients in CellSearch tubes containing EDTA. All the samples were analyzed within 24 h after collection. A set of patient samples (n=7) were analyzed to determine whether the approach would be suitable for the analysis of CTCs mRNA. Sixteen milliliters of blood were split into four tubes to be further utilized for the determination of $N_{CP}$, $N_{NSP}$, and $N_{Ab}$ using the microfluidic approach and for RT-qPCR analysis. The mononuclear cells were isolated using Ficoll method and were subsequently suspended in 250 µL of 2% FBS solution in PBS. Anti-CD15 MNPs were gently shaken with the cell suspension for 30 min at room temp. The captured leukocytes were pelleted using a magnetic separation rack and the supernatant was collected for further analysis. In the first tube, the supernatant was incubated with 250 µL of 8% PFA in DPBS/DTT for 15 min at 37° C. After centrifugation, 100 µL of 0.3% TX-100 in DPBS/DTT were added and the suspension was incubated for 10 min at room temp. The cells were gently shaken with 100 µL of DPBS/DTT containing MNPs-labeled CP1-AR-V7 and MNPs-labeled AR-V7-CP2 in DPBS/DTT for 3 h at room temp. In the second tube, a control experiment was carried out in which the cells were gently shaken with the MNPs-labeled nonspecific dual probe (NSP) for 3 h at room temp, subsequent to cell fixation and permeabilization. In the third tube, another control experiment was carried out in which the cells were gently shaken with MNPs-anti-EpCAM (without prior fixation or permeabilization) for 3 h at room temp. The cells were loaded into the 6-zone microfluidic device at a flow rate of 600 µL h$^{-1}$ and subsequently stained with APC-labeled anti-EpCAM, APC-labeled anti-CK antibodies, AF488-labeled anti-CD45 antibody, and DAPI. In the fourth tube, the cells were gently shaken with MNPs-anti-EpCAM (without fixation or permeabilization) for 1 h at room temp. The cells were loaded into a cell-extraction microfluidic device at a flow rate of 8 mL h⁻¹. After washing, the Tygon tubing connecting the zones were cut and the cells were gently pipetted out the device and stored at −80° C. before RT-qPCR analysis.

An example method for flow cytometric analysis of survivin protein expression in PC3 cells is now discussed. Flow cytometry was used to analyze the level of survivin protein in PC3 cells before and after silencing the survivin gene with LY21813080 siRNA[14]. Briefly, PC3 cells (200, 000 cells) were incubated with the blocking buffer (1% BSA in PBS) for 30 min at room temp. Afterward, the cells were fixed 4% PFA and permeabilized with 0.2% TX-100. The cells were incubated with 10 μL of 100 μg mL⁻¹ of DL555-labeled anti-survivin antibody (Novus biologicals, US) for 1 h at room temp. Mouse IgG (Abcam, US) was used as a negative control at the assay conditions. Subsequently, samples were injected into FACSCanto flow cytometer (BD Biosciences, US) and measurements were plotted as histograms. Absorbance values were normalized to unstained control. A total of 10,000 cells were analyzed per cell line.

An example method for dynamic light scattering (DLS) measurement of the formed clusters of magnetic nanoparticles is now discussed. DLS experiments were carried out using Zeta sizer Nano series (Malvern Instruments, UK), to prove the formation of MNP clusters upon hybridization between MNPs-labeled dual probe and target mRNA. Prior to analysis, MNPs-labeled CP1-TMPRSS2/ERG (15 μg) and MNPs-labeled TMPRSS2/ERG-CP2 (15 μg) were incubated with 1 μM synthetic TMPRSS2/ERG in DPBS/DTT for 3 h at room temp. A control experiment was carried in which the target was incubated with individual capture probes (CP1 or CP2).

EXAMPLE EXPERIMENTS

Reference will now be made to a series of example experiments conducted to investigate possible variations to the disclosed method. These experiments are described for the purpose of illustration only, and are not intended to be limiting or promissory.

In the following example experiments, a 6-zone microfluidic device 6 was used. However, other variations are possible. For example, a device with fewer than 6 zones or more than 6 zones may be used.

Further, in the following example experiments the linear velocity profile was 1×, 0.47×, 0.31×, 0.23×, 0.18×, 0.15× corresponding to zones 1-6 respectively. However, a different linear velocity profile may be used. The decline in flow rate is provided as an example, and other changes to flow rate across the zones including increase or decrease by other factors, may be suitable.

Dual probes, comprising two capture probes (CP1 and CP2), 14 and 15 were designed for the following example experiments to target BIRC5 (survivin), TMPRSS2/ERG, AR, or AR-V7 mRNA in PC3, LNCaP, or VCaP cells. Sequences of the probes 14 and 15 used in this study are detailed in Table 1.

TABLE 1

Sequence of the nucleic acids utilized in the example experimental setup

| Nucleic acid | Sequence |
| --- | --- |
| CP1-TMPRSS2/ERG | 5' GAT AAG GCT TCC TGC CGC GC 3'-Biotin-(TEG) (SEQ ID NO: 1) |
| TMPRSS2/ERG-CP2 | Biotin-(TEG)-5' CAA CGA CTG GTC CTC ACT CA 3' (SEQ ID NO: 2) |
| TMPRSS2/ERG (synthetic) | 5' GCG CGG CAG GAA GCC TTA TCA GTT GTG AGT GAG GAC CAG TCG TTG 3' (SEQ ID NO: 3) |
| Ctrl-TMPRSS2/ERG | 5' GTT GCT GAC CAG GAG TGA GTG TTG ACT ATT CCG AAG GAC GGC GCG 3' (SEQ ID NO: 4) |
| AF488-TMPRSS2/ERG-CP1 | AF488-5' GAT AAG GCT TCC TGC CGC GC 3'-Biotin-(TEG) (SEQ ID NO: 5) |
| CP2-TMPRSS2/ERG-AF594 | Biotin-(TEG)-5' CAA CGA CTG GTC CTC ACT CA 3'-AF594 (SEQ ID NO: 6) |
| CP1-survivin | 5' CAG TTC TTG AAT GTA GAG AT 3'-Biotin-(TEG) (SEQ ID NO: 7) |
| Survivin-CP2 | Biotin-(TEG)-5' GCA GGC GCA GCC CTC CAA GA 3' (SEQ ID NO: 8) |
| CP1-AR-FL | 5' TGC TTT CAT GCA CAG GAA TT 3'-Biotin-(TEG) (SEQ ID NO: 9) |
| AR-FL-CP2 | Biotin-(TEG)-5' CTG GAA TAA TGC TGA AGA GT 3' (SEQ ID NO: 10) |
| CP1-AR-V7 | 5' CTG ATG AAG AGA AGC ATG TG 3'-Biotin-(TEG) (SEQ ID NO: 11) |
| AR-V7-CP2 | Biotin-(TEG)-5' TGG GAG AAG AAT GAG AGG CT 3' (SEQ ID NO: 12) |
| LY2181308 | 5' TGT GCT ATT CTG TGA ATT 3' (SEQ ID NO: 13) |

TABLE 1-continued

Sequence of the nucleic acids utilized in the example experimental setup

| Nucleic acid | Sequence |
|---|---|
| TMPRSS2/ERG Forward primer | FAM-5' CAG GAG GCG GAG GCG GA 3'-MGB NFQ (SEQ ID NO: 14) |
| TMPRSS2/ERG Reverse primer | FAM-5' GGC GTT GTA GCT GGG GGT GAG 3'-MGB NFQ (SEQ ID NO: 15) |
| Survivin Forward primer | FAM-5' CTT TCT CAA GGA CCA CCG CAT CT 3'-MGB NFQ (SEQ ID NO: 16) |
| Survivin Reverse primer | FAM-5' GCA CTT TCT CCG CAG TTT CCT C 3'-MGB NFQ (SEQ ID NO: 17) |
| AR-FL Forward primer | FAM-5' GGA ATT CCT GTG CAT GAA AGC 3'-MGB NFQ (SEQ ID NO: 18) |
| AR-FL Reverse primer | FAM-5' CGA TCG AGT TCC TTG ATG TAG TTC 3'-MGB NFQ (SEQ ID NO: 19) |
| AR-V7 Forward primer | FAM-5' CTT GTC GTC TTC GGA AAT GTT ATG 3'-MGB NFQ (SEQ ID NO: 20) |
| AR-V7 Reverse primer | FAM-5' CTT TCT TCA GGG TCT GGT CAT T 3'-MGB NFQ (SEQ ID NO: 21) |
| TBP Forward primer | FAM-5' CGG CTG TTT AAC TTC GCT TC 3'-MGB NFQ (SEQ ID NO: 22) |
| TBP Reverse primer | FAM-5' CAC ACG CCA AGA AAC AGT GA 3'-MGB NFQ (SEQ ID NO: 23) |
| GAPDH Forward primer | FAM-5' GAG TCA ACG GAT TTG GTC GT 3'-MGB NFQ (SEQ ID NO: 24) |
| GAPDH Reverse primer | FAM-5' GAC AAG CTT CCC GTT CTC AG 3'-MGB NFQ (SEQ ID NO: 25) |
| CP1-PDL1 | 5' TGT TCA GAG GTG ACT GGA TC 3'-Biotin-(TEG) (SEQ ID NO: 26) |
| PDL1-CP2 | Biotin-(TEG)-5' GCC CTC AGC CTG ACA TGT CA 3' (SEQ ID NO: 27) |
| CP1-PD1 | 5' CTC AGG GAC ACA GGG CAC GG 3'-Biotin-(TEG) (SEQ ID NO: 28) |
| PD1-CP2 | Biotin-(TEG)-5' AGA CAA TGG TGG CAT ACT CC 3' (SEQ ID NO: 29) |
| CP1-PARP | 5' TCT GTA GCA AGG AGG CTG AA 3'-Biotin-(TEG) (SEQ ID NO: 30) |
| PARP-CP2 | Biotin-(TEG)-5' CTG CTT CTT CAG GGC TTC TT 3' (SEQ ID NO: 31) |

In the first set of experiments, the use of single nanoparticle-tethered capture probes was not sufficient for high levels of magnetic capture. In proof-of-concept studies monitoring the capture efficiency of a model cell line (PC3 cells), low capture efficiencies were observed when a single capture probe was used. However, when a combination of two capture probes were used, the capture efficiency increased significantly, as shown in FIG. 6.

Figure 6:
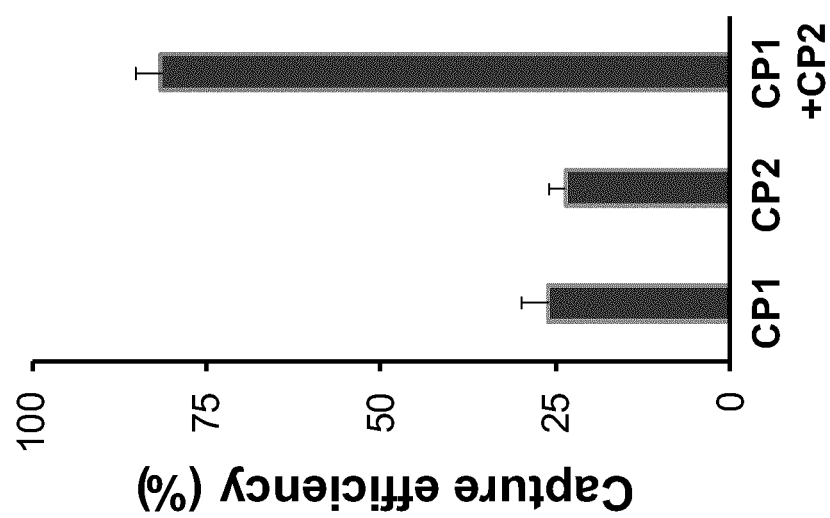
FIG. 6 shows a graph of example enhancement of capture efficiency of PC3 cells by using a dual probe in the microfluidic device of FIGS. 2 and 5.

FIG. 6 shows an exemplary graph of the enhancement of capture efficiency of PC3 cells within the microfluidic device 6 by using a dual probe. One hundred cells were used in these trials. When PC3 cells were subjected to magnetic capture based on targeting the survivin mRNA, only low levels of cell capture were observed if single capture probes were used, while when two capture probes were coincubated with the cells, capture efficiency was increased significantly.

DLS measurements revealed that combining the two capture probes produced large aggregates in the presence of the complementary target strand (FIG. 7), indicating that the dual probe strategy triggered the self-assembly of large magnetic clusters. These clusters are likely retained within the permeabilized cells, while the single nanoparticles could diffuse out of the cells even after binding a target sequence.

The results from these exemplary experiments demonstrate that mRNA-triggered aggregation of MNPs-labeled dual probe could enhance the magnetic susceptibility of the cells and facilitate their capture within the device 6.

Notably, survivin has a gene sequence that has been explored as a potential cancer biomarker. Survivin promotes cell division and suppresses apoptosis in many human cancers. The antiapoptotic effect is related to its ability to inhibit caspases either directly or indirectly[16]. The transcription of the survivin gene is higher in tumors compared to normal tissues and is often correlated with metastasis and poor prognosis in cancer patients[17]. It was found that using the dual probe (CP1+Cp2) has allowed for the highest recoveries of PC3 cells either in the buffer solution (82±4%) or blood (71±5%) subsequent to RBCs removal using Ficoll method and WBCs depletion with MNPs-tagged anti-CD15. On the other hand, using a non-specific dual probe (NSP) or CP1 or CP2 individually (at double concentration) has permitted recoveries of 9±2%, 26±4%, and 24±3%, respectively (FIG. 8).

Figure 8:
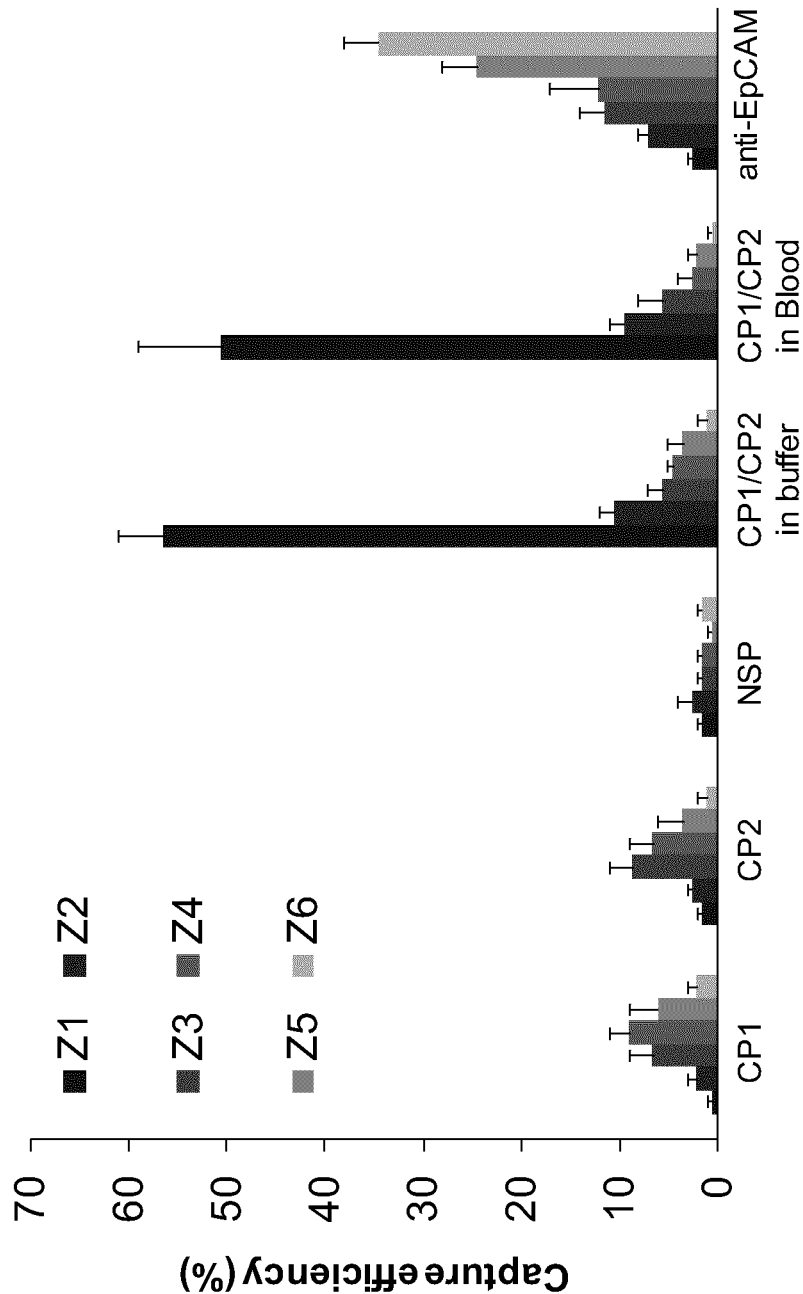
FIG. 8 is a chart of example cell capture and profiling mediated by mRNA-triggered aggregation of an example of the disclosed MNPs-labeled dual probe enhancing the capture efficiency of cells.

FIG. 8 shows that mRNA-triggered aggregation of the MNPs-labeled dual probe can enhance the capture efficiency of cells. One hundred cells were used in these trials. We found that using the dual probe (CP1+CP2) has allowed for the highest recoveries of PC3 cells either in the buffer solution (82±4%) or blood (71±5%) subsequent to RBCs removal using Ficoll method and WBCs depletion with MNPs-tagged anti-CD15. On the other hand, using CP1 or CP2 individually (at double concentration) or a non-specific dual probe (NSP) resulted in recoveries of 26±4%, 24±3%, and 9±2%, respectively.

As a proof-of-concept, this approach was used to analyze survivin mRNA in PC3, LNCaP, and VCaP cells. The cells were spiked into blood to ensure that heterogeneous samples were compatible with the approach. The number of cells captured using anti-EpCAM was compared to the number captured using the mRNA-directed approach to determine the overall mRNA capture fraction. For each of the cell lines tested, the EpCAM-mediated capture-efficiencies were high (VCaP 92±4%, LNCaP 95±3%, PC3 92±6%), but for the mRNA-targeted trials, the capture levels varied (VCaP 38±11%, LNCaP 66±9%, PC3 79±8%), reflecting the varied expression of survivin in these cell lines, as shown in FIGS. 9 and 10.

Figure 9:
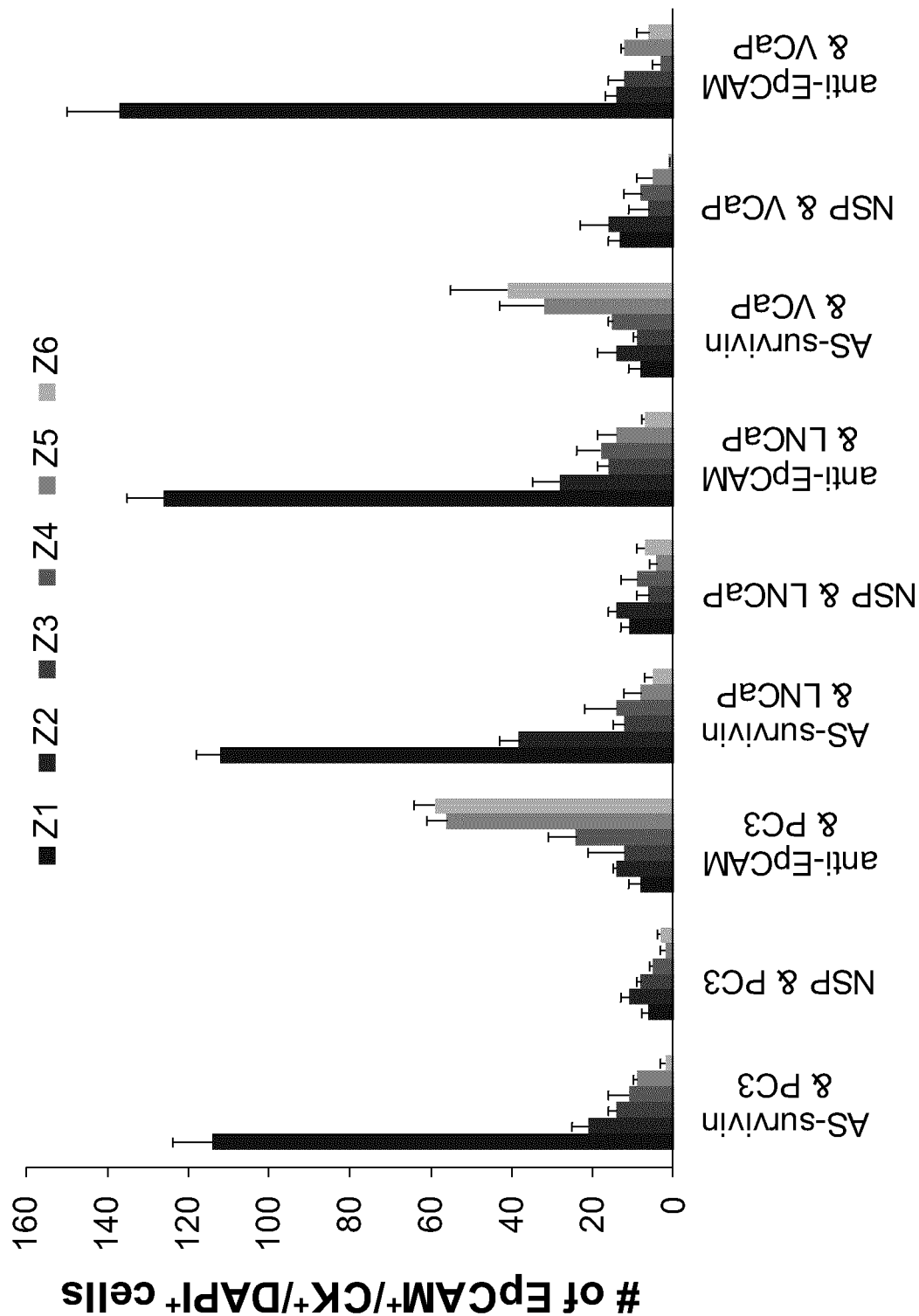
FIG. 9 is a chart illustrating example capture of three prostate cancer cell lines (PC3, LNCaP, VCaP) based on the expression levels of survivin mRNA in these cells.

FIG. 9 is an example chart of capture of three prostate cancer cell lines (PC3, LNCaP, VCaP) based on the expression levels of survivin mRNA in these cells. Three prostate cancer cell lines (200 cells) were spiked in blood to ensure that heterogeneous samples were compatible with this approach. Subsequent to RBCs lysis and WBCs depletion, the cells were fixed with 4% PFA and permeabilized with 0.3% TX-100. The cells were incubated with two MNPs-tagged DNA probes complementary to the target survivin mRNA (AS-survivin). A control experiment was carried out in which the cells were incubated with MNPs-tagged non-specific dual probe (NSP), subsequent to cell fixation and permeabilization. Another control experiment was carried out in which the cells were incubated with MNPs-tagged anti-EpCAM. The cells were loaded into the microfluidic device 6 at a flow rate of 600 µL h$^{-1}$, stained with APC-labeled anti-CK, APC-labeled anti-EpCAM, and DAPI. Only CK$^+$/EpCAM$^+$/DAPI$^+$ cells were counted.

Figure 10:
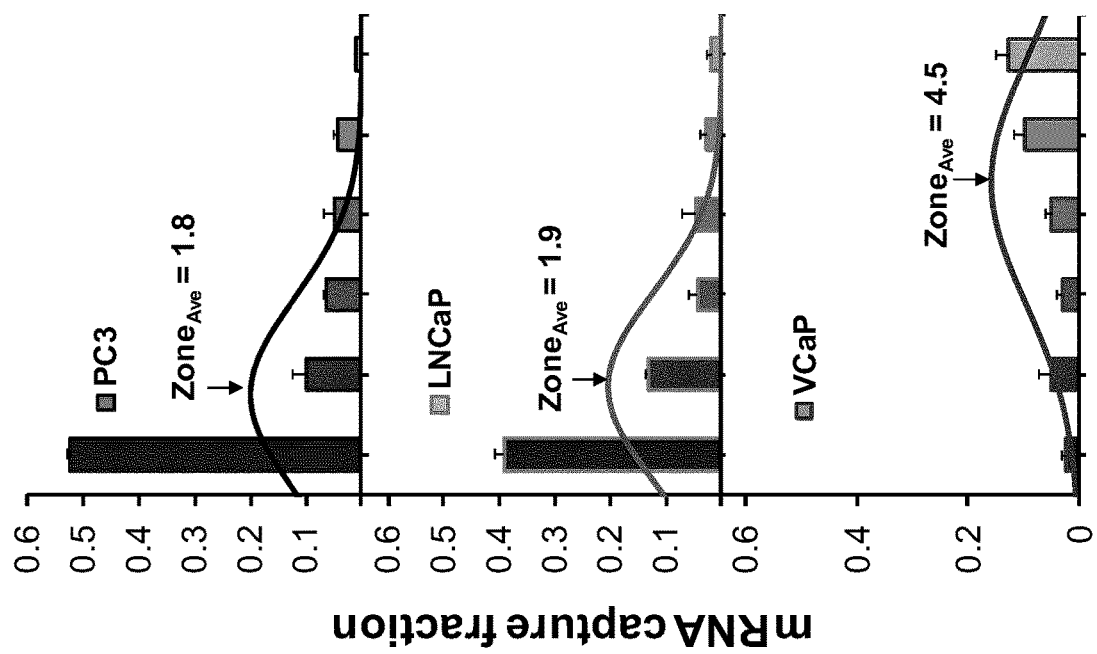
FIG. 10 shows charts of example cellular determination of survivin mRNA in PC3, LNCaP, and VCaP cell lines using the microfluidic approach.

FIG. 10 is an example chart of a cellular analysis of survivin mRNA in PC3, LNCaP, and VCaP cell lines using the microfluidic approach. Two hundred cells were used in these trials. The curves represent the normal distribution fit to the capture data. The mRNA capture fraction reflects the capture using mRNA-targeted nanoparticles relative to those labelled with anti-EpCAM.

Figure 11:
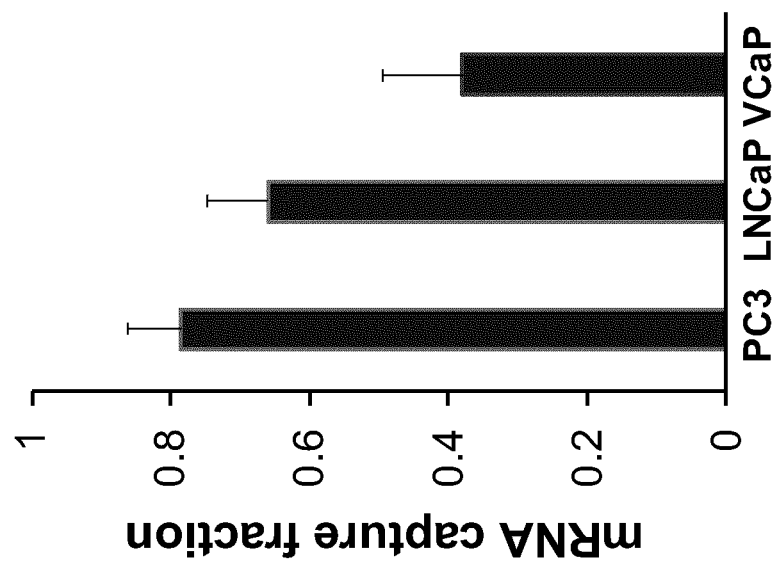
FIG. 11 is a chart illustrating example overall survivin mRNA capture fraction for PC3, LNCaP, and VCaP cells using the microfluidic approach.

The overall mRNA capture fraction for PC3, LNCaP, and VCaP cells, which compares the number of cells captured with mRNA-targeted nanoparticles versus anti-EpCAM targeted nanoparticles, was determined. The overall capture fraction was found in the order of PC3>LNCaP>VCaP (FIG. 11). These studies were conducted with 200 cells spiked into one milliliter of blood.

Figure 12:
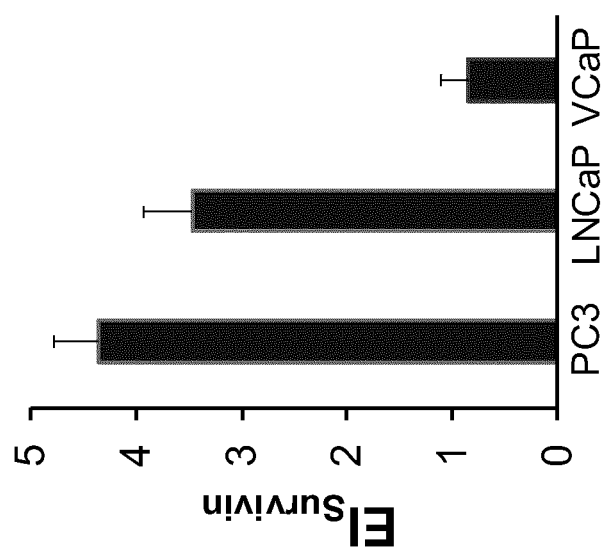
FIG. 12 is a chart illustrating example survivin mRNA expression index ($EI_{survivin}$), which reflects the mRNA capture fraction divided by the average capture zone.

For each cell line, the median zone of capture was determined to provide a parameter that could be used to refine the calculation of relative RNA expression for the cell lines. The PC3 and LNCaP cells were primarily captured in the early zones of the device and had average zone values of 1.8 and 1.9, respectively. The VCaP cells, in addition to having a much lower overall capture efficiency, had a much larger average zone value of 4.5. An expression index (EI) for the survivin mRNA was then calculated for each cell line; values are shown in FIG. 12. The EI value was calculated by dividing the capture fraction by the average zone parameter.

Figure 13:
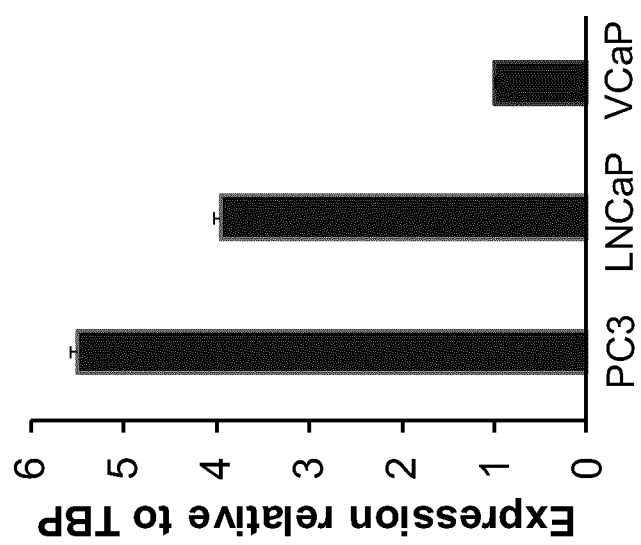
FIG. 13 shows chart illustrating example cellular analysis of survivin mRNA in PC3, LNCaP, and VCaP cell lines using RT-qPCR.
Figure 14A:
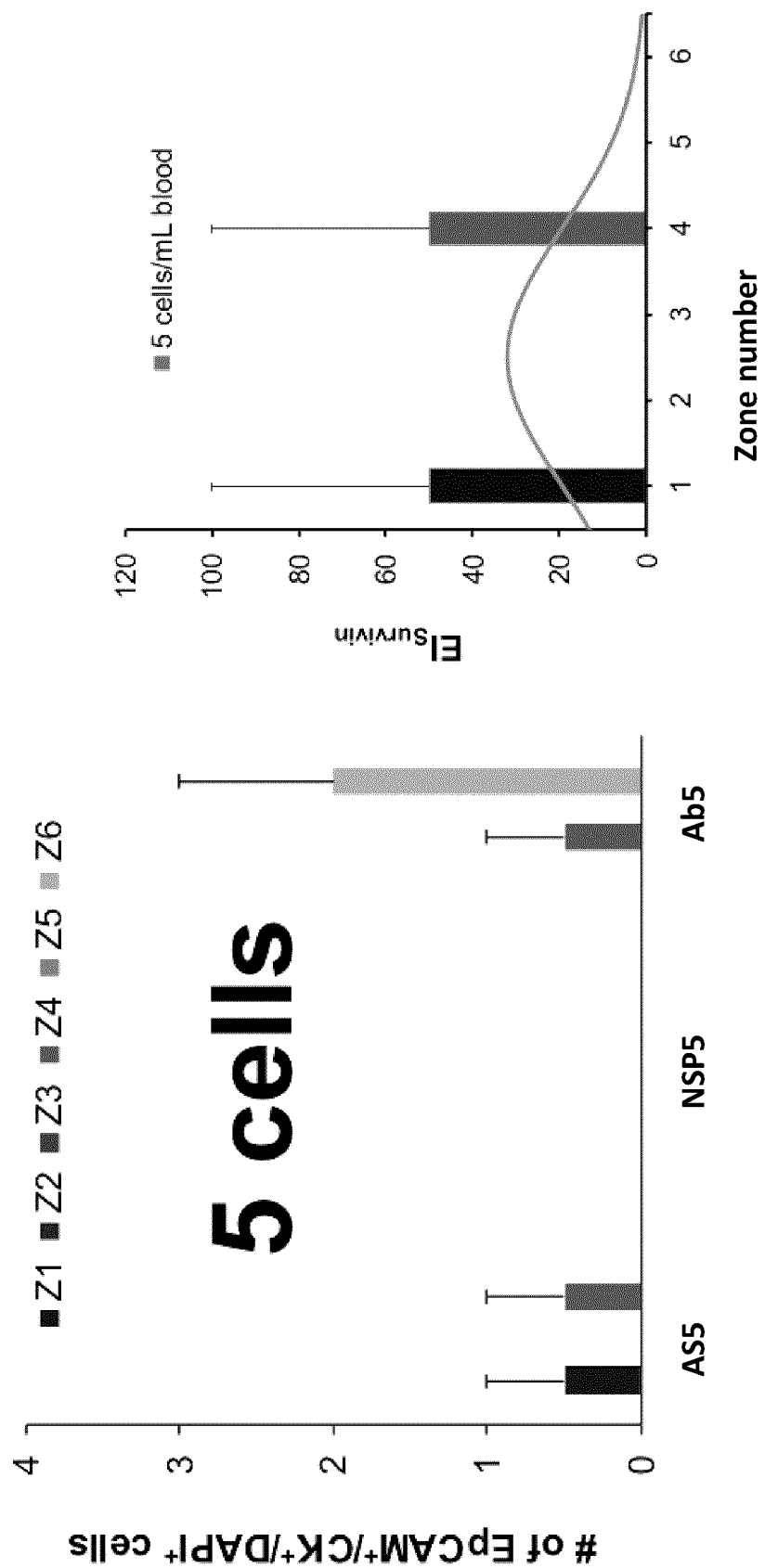
FIGS. 14A-14G are charts illustrating example sensitivity of the mRNA analysis approach assessed by cellular determination of survivin mRNA in 1 mL of blood spiked with different numbers (5, 10, 25, 50, 100, 500, 1000, respectively) of PC3 cells.
Figure 14B:
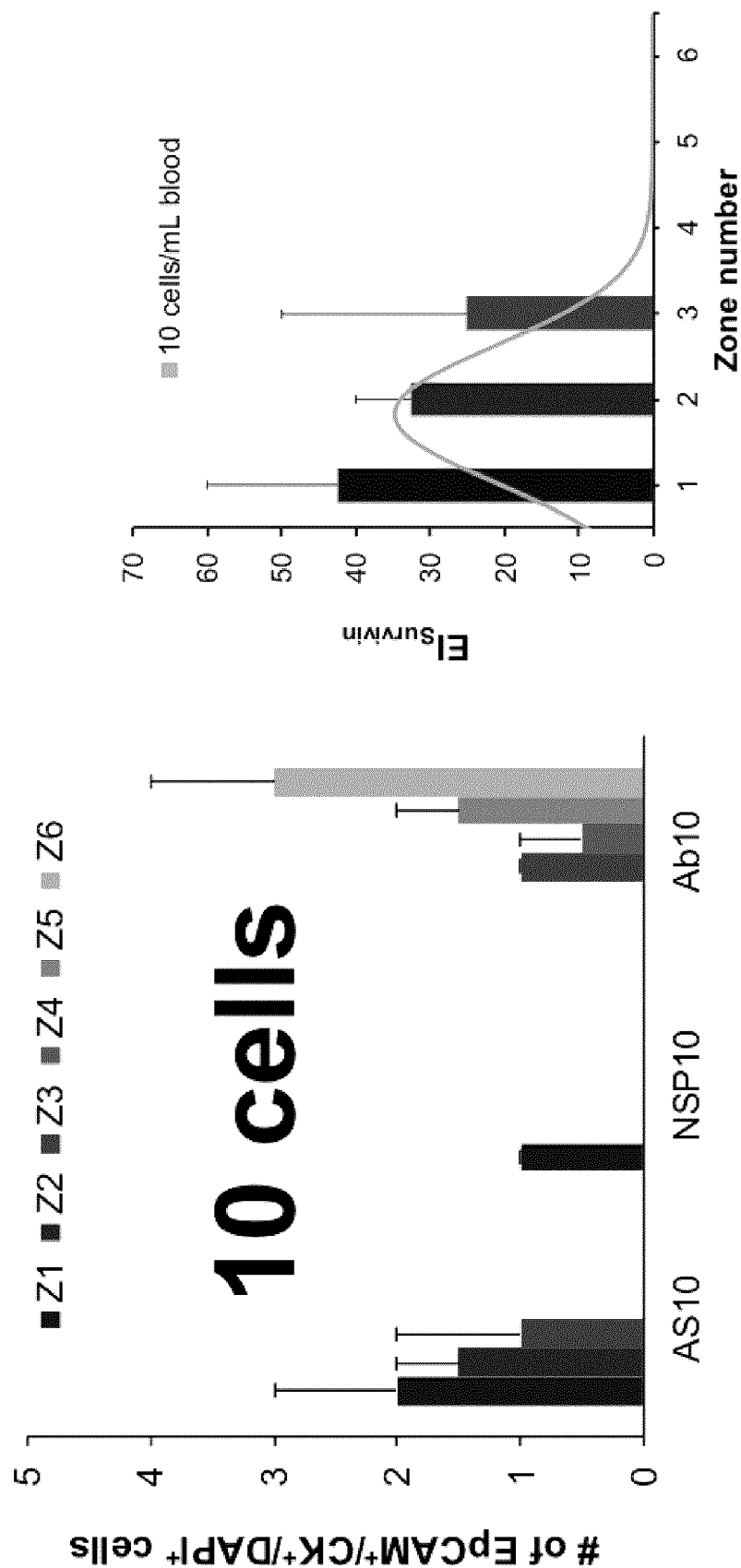
Figure 14C:
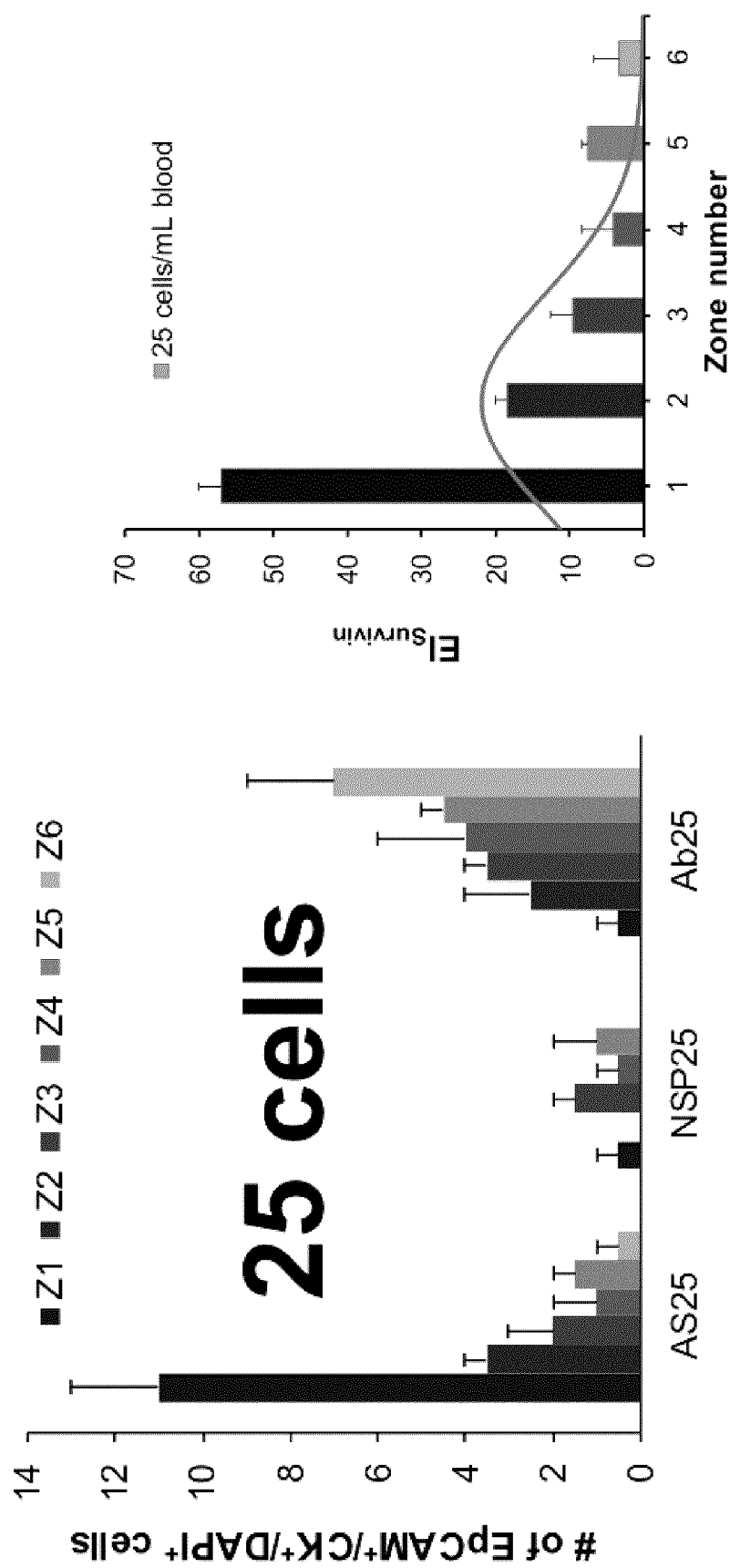
Figure 14D:
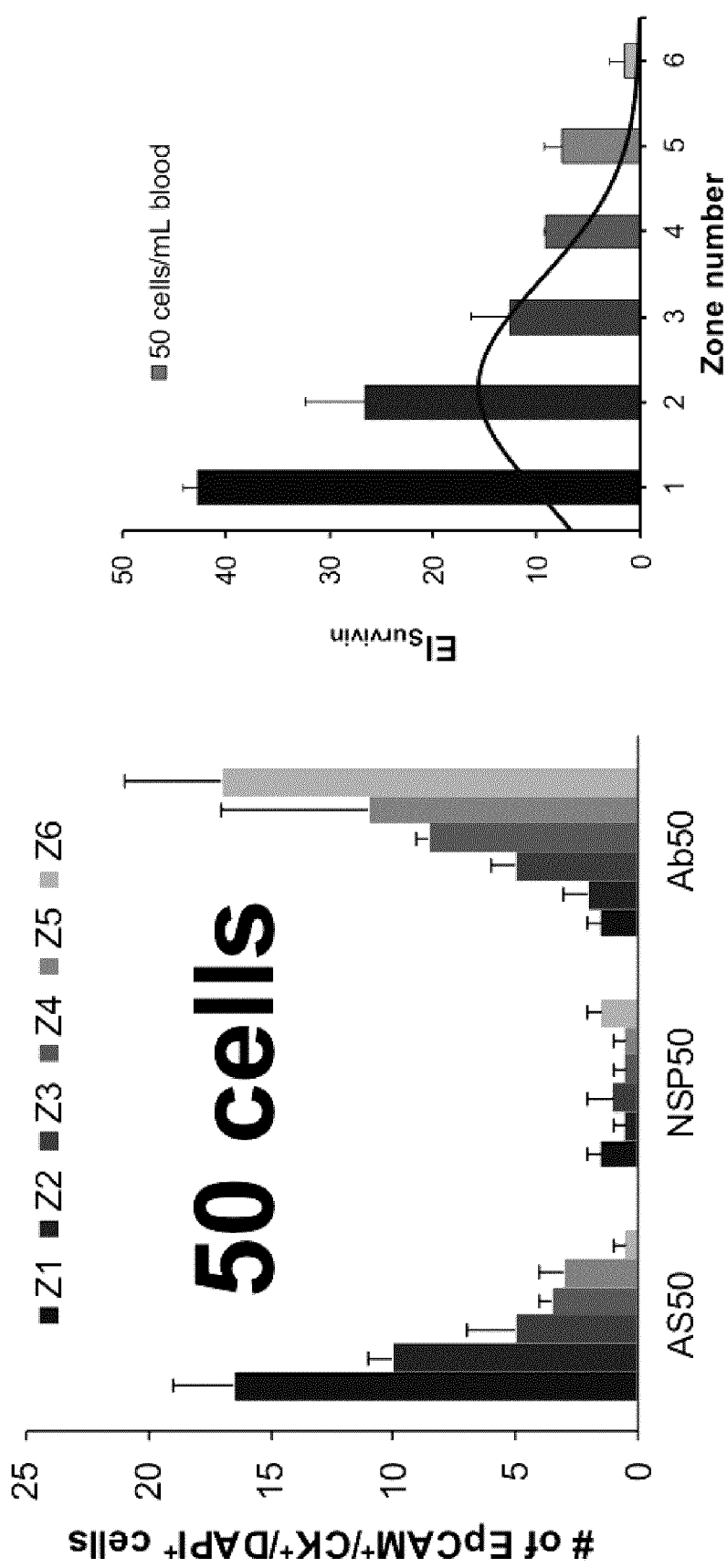
Figure 14E:
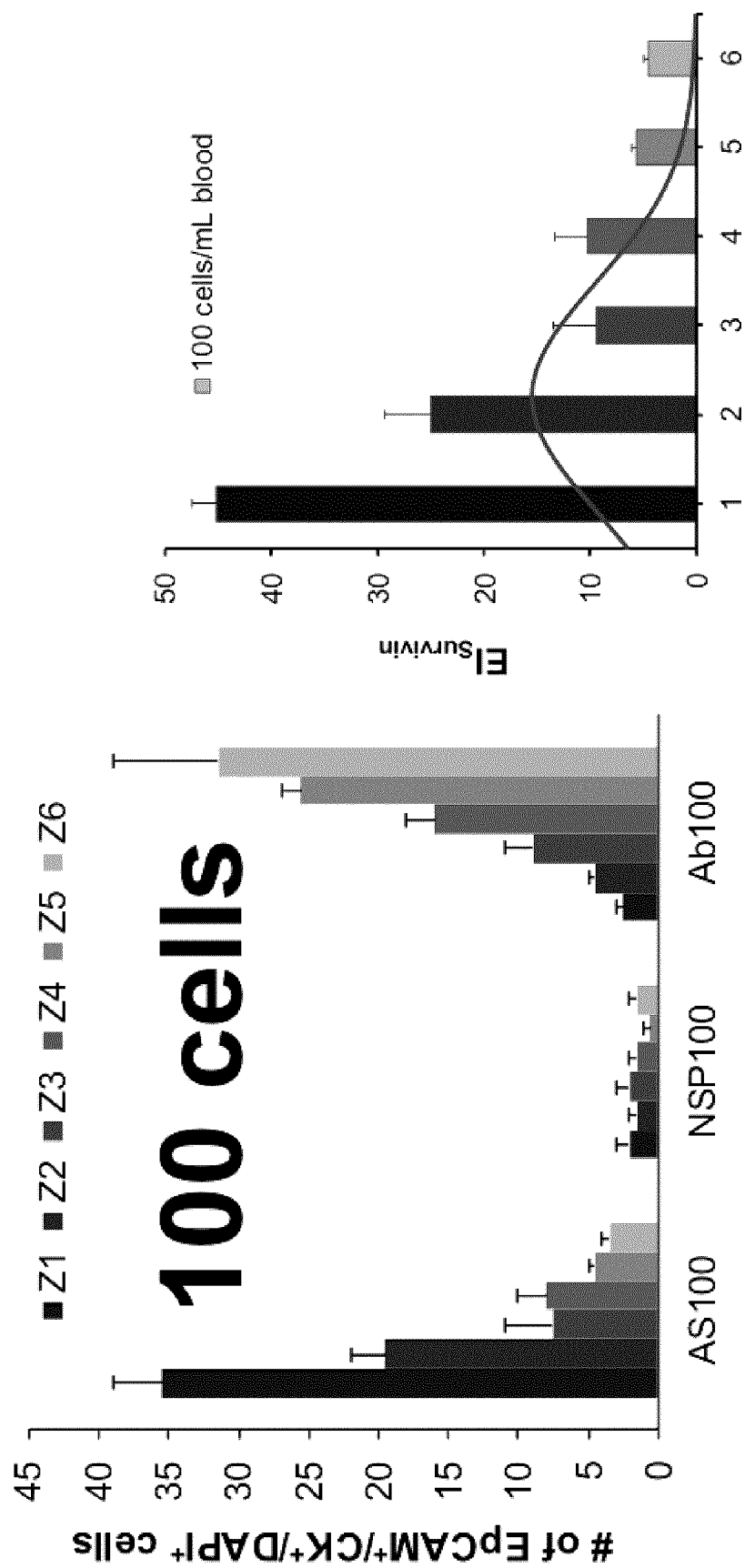
Figure 14F:
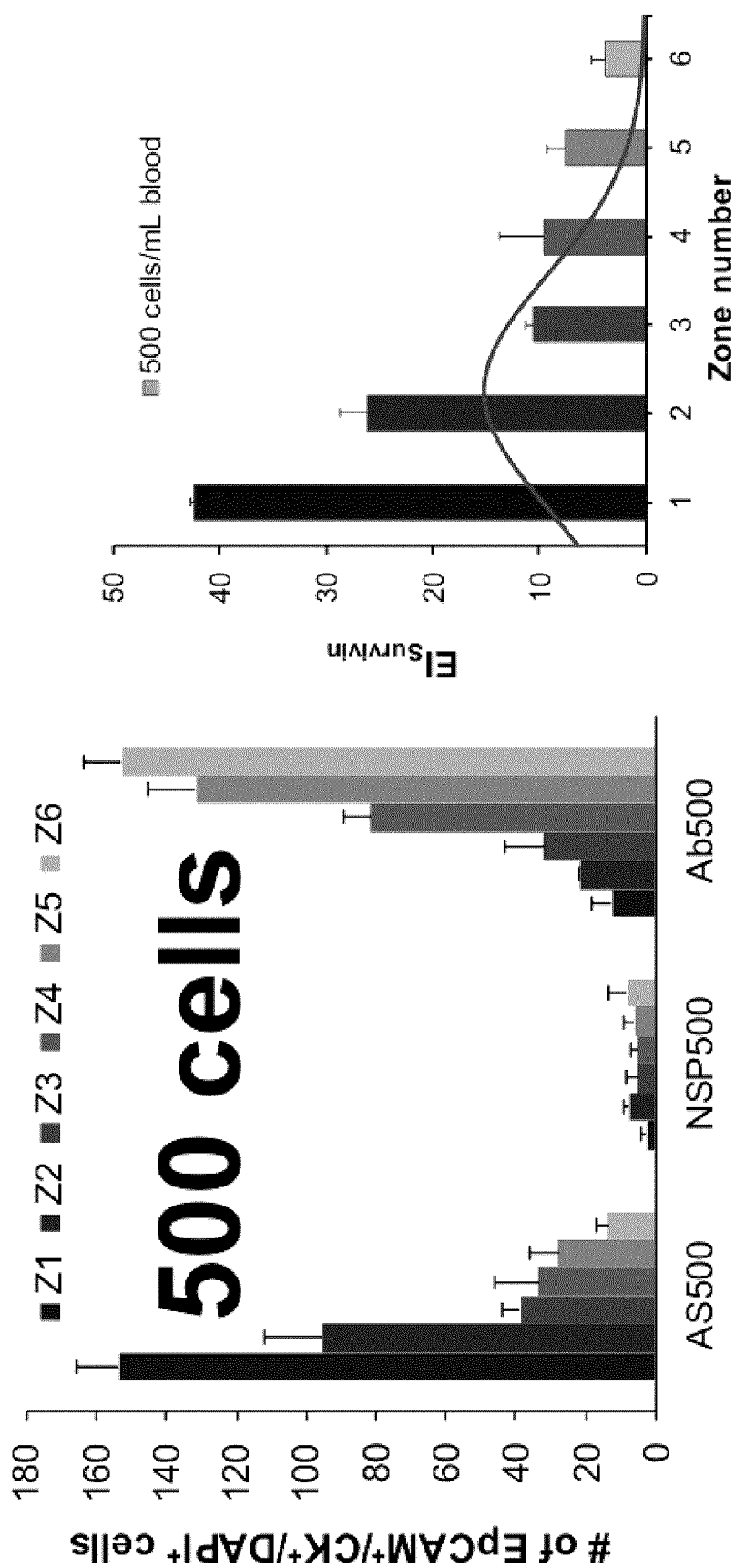
Figure 14G:
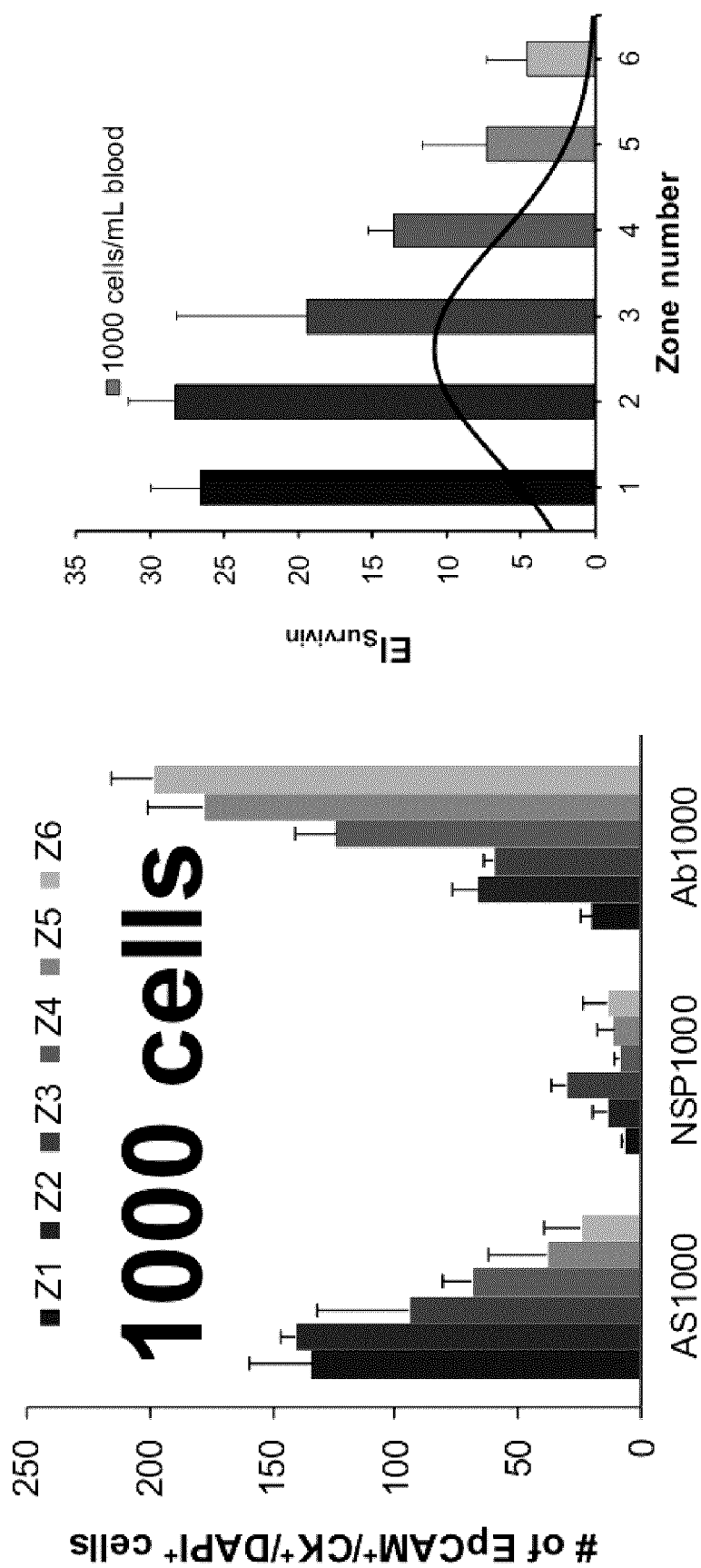

Reverse transcription and quantitative PCR were performed using the same cell lines to evaluate the relative expression of survivin mRNA. The TATA-box binding protein, TBP, was used as a standard, and the expression levels of survivin mRNA were compared to TBP for each cell line (FIG. 13). The levels of expression measured using our approach (FIG. 12) and PCR (FIG. 13) were strikingly similar, indicating that our method is also a quantitative approach to monitoring gene expression.

FIG. 13 shows example graph of reverse transcription-quantitative polymerase chain reaction (RT-qPCR) analysis of survivin mRNA in the three cell lines (PC3, LNCaP, and VCaP cell lines).

FIGS. 14A-14G show examples of the cellular determination of survivin mRNA in 1 mL of blood spiked with different numbers (5, 10, 25, 50, 100, 500, 1000, respectively) of PC3 cells. The spiked blood samples were depleted of RBCs and WBCs prior to analysis using the Ficoll method and MNPs labeled anti-CD15, respectively. The cells were fixed with 4% PFA and permeabilized with 0.3% TX-100. The cells were incubated with two MNPs-tagged DNA probes complementary to the target survivin mRNA (AS-survivin). A control experiment was carried out in which the cells were incubated with MNPs-tagged non-specific dual probe (NSP), subsequent to cell fixation and permeabilization. Another control experiment was carried out in which the cells were incubated with MNPs-tagged anti-EpCAM. The cells were loaded into the microfluidic device 6 at a flow rate of 600 µL h$^{-1}$, stained with APC-labeled anti-CK, APC-labeled anti-EpCAM, and DAPI. Only CK$^+$/EpCAM$^+$/DAPI$^+$ cells were counted.

Figure 15:
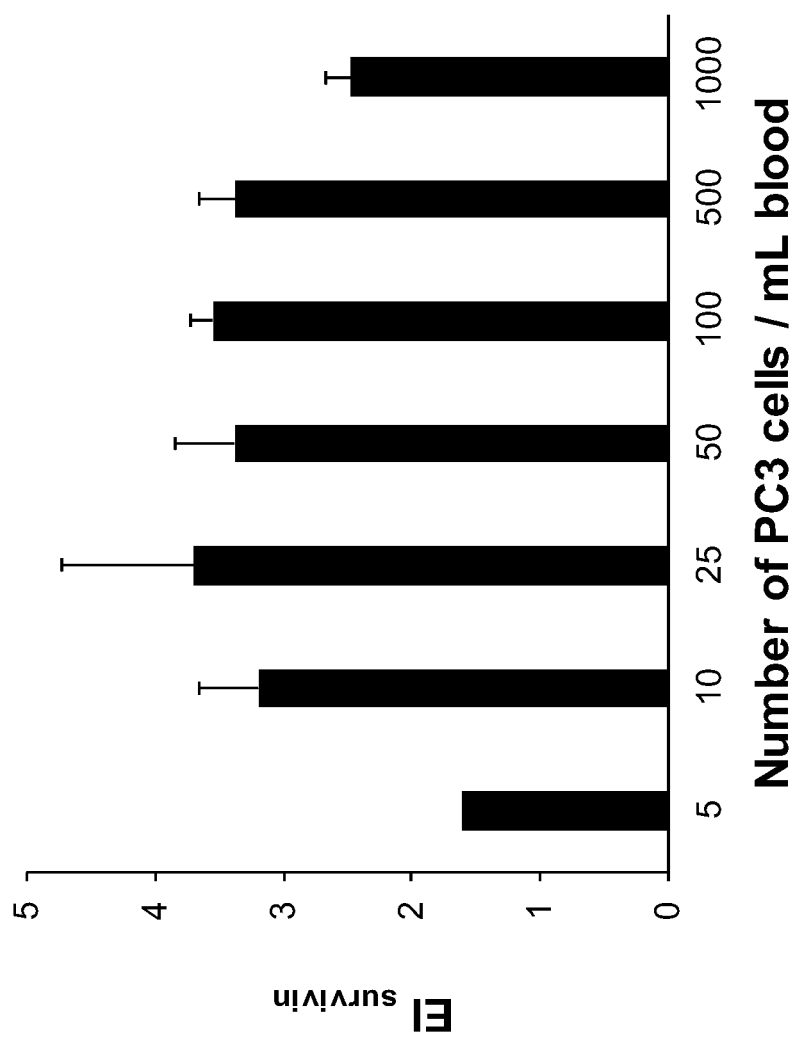
FIG. 15 is a chart illustrating example expression index values of survivin mRNA determined using 1 mL of blood spiked with different numbers of PC3 cells, including 5, 10, 25, 50, 100, 500, and 1000 cells.

FIG. 15 shows example expression index values of survivin mRNA determined in 1 mL of blood spiked with different numbers of PC3 cells, including 5, 10, 25, 50, 100, 500, and 100 cells. The spiked blood samples were depleted of RBCs and WBCs prior to analysis using the Ficoll method and MNPs labeled anti-CD15, respectively. Cellular determination of survivin mRNA was carried out and EI$_{survivin}$ was determined for each sample.

Figure 16:
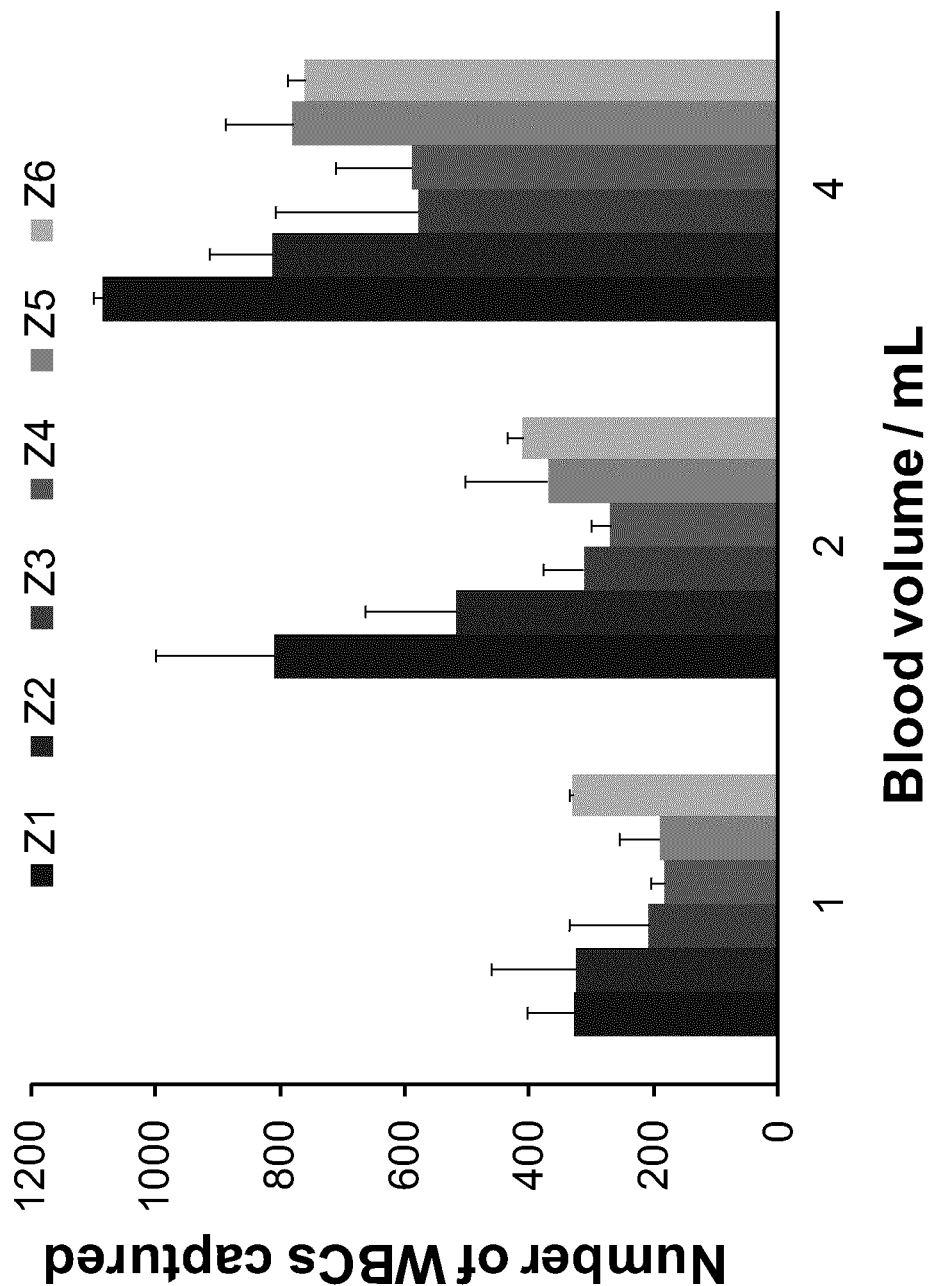
FIG. 16 is a chart illustrating example purity of the cancer cells captured within an example of the microfluidic device.

FIG. 16 is an example chart of the purity of cancer cells captured within the microfluidic device 6. PC3 cells were spiked into 1, 2, and 4 mL of blood. RBCs were removed using the Ficoll method and WBCs are depleted using MNPs-tagged anti-CD15 antibody. After fixation with 4% PFA and permeabilization with 0.3% TX-100, the cells were incubated with two MNPs-tagged DNA probes complementary to the target survivin mRNA (AS-survivin). The cells were loaded into the microfluidic device 6 at a flow rate of 600 µL h$^{-1}$, stained with APC-labeled anti-CK, APC-labeled anti-EpCAM, DL555-labeled anti-survivin, and DAPI. Only DAPI$^+$/CD45$^+$ cells were counted to determine the number of WBCs non-specifically bound to each zone in the device.

It was noticed that the mRNA expression pattern and index obtained using 10 PC3 cells were comparable to those determined using 500 cells, suggesting that the detection limit of our method is 10 cells in 1 mL of blood. In addition, the purity of the captured cells from blood was also assessed and up to ~99.99% of the WBCs (~7,000,000 per mL of blood) were depleted from 1, 2, and 4 mL blood, as shown in FIG. 16.

Next, the selectivity of the disclosed approach was demonstrated by analyzing survivin mRNA in PC3 cells before and after silencing the survivin gene with a small interfering RNA (siRNA). PC3 cells were transfected with LY2181308, a previously characterized siRNA directed against survivin[14]. It was found that the transfected PC3 cells have exhibited lower $EI_{survivin}$ compared to control cells (FIGS. 17 and 18).

Figure 17:
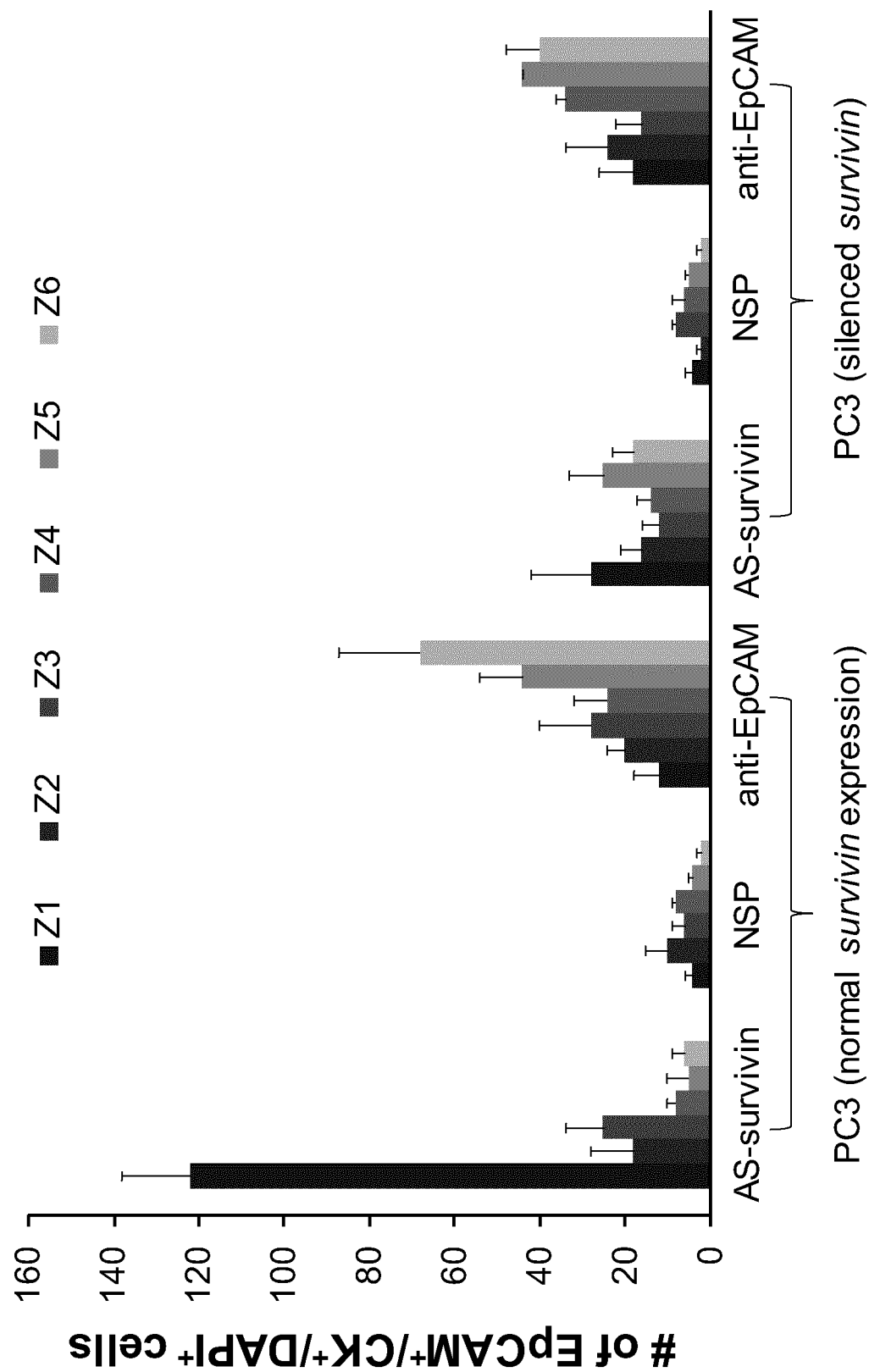
FIG. 17 is a chart illustrating example cellular determination of survivin mRNA in PC3 cells before and after silencing the survivin gene with LY2181308 siRNA.

FIG. 17 is an example chart of the cellular determination of survivin mRNA in PC3 cells before and after silencing the survivin gene with LY2181308 siRNA. PC3 cells (200 cells), either with normal survivin expression or after survivin silencing, were fixed with 4% PFA and permeabilized with 0.3% TX-100. The cells were subsequently incubated with two MNPs-tagged DNA probes complementary to the target survivin mRNA (AS-survivin). A control experiment was carried in which the cells were incubated with a MNPs-tagged non-specific dual probe (NSP) subsequent to cell fixation and permeabilization. Another control experiment was carried out in which the cells were incubated with MNPs-tagged anti-EpCAM. Two hundred cells were used in these trials. The cells were loaded into the microfluidic device 6 at a flow rate of 600 μL h$^{-1}$, immunostained with APC-labeled anti-CK, APC-labeled anti-EpCAM, DL555-labeled anti-survivin, antibodies specific to two apoptosis markers including AF488-labeled anti-PARP and AF488-labeled anti-caspase 3, and DAPI. Only CK$^+$/EpCAM$^+$/DAPI$^+$ cells were counted.

Figure 18:
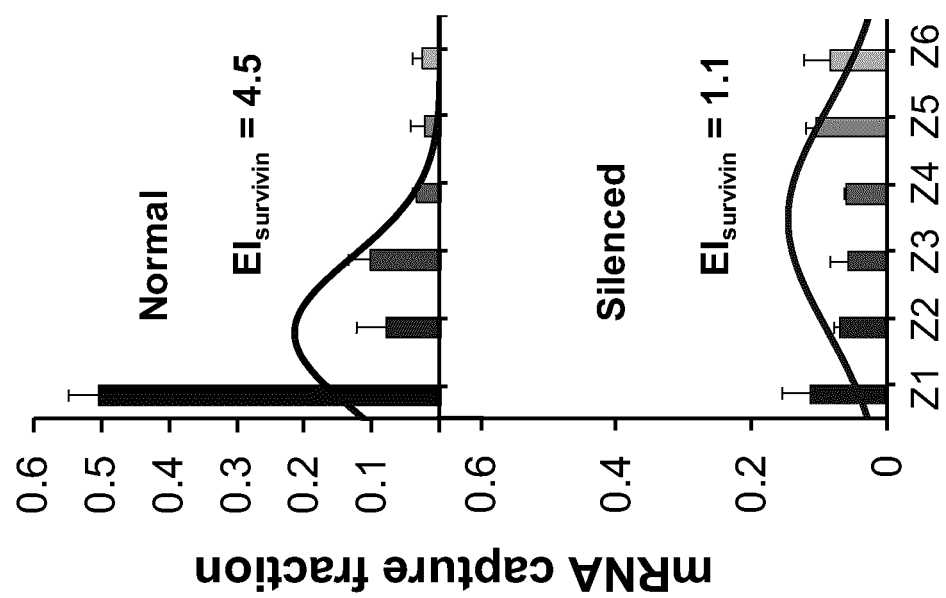
FIG. 18 shows charts illustrating example selectivity of the mRNA determination approach.

FIG. 18 is an example chart that shows the selectivity of the mRNA determination approach. The selectivity of the disclosed approach was assessed by measuring $EI_{survivin}$ in PC3 cells before and after silencing the survivin gene with LY2181308 siRNA[14]. Two hundred cells were used in these trials. The curves represent the normal distribution fit to the $EI_{survivin}$ data.

Figure 19:
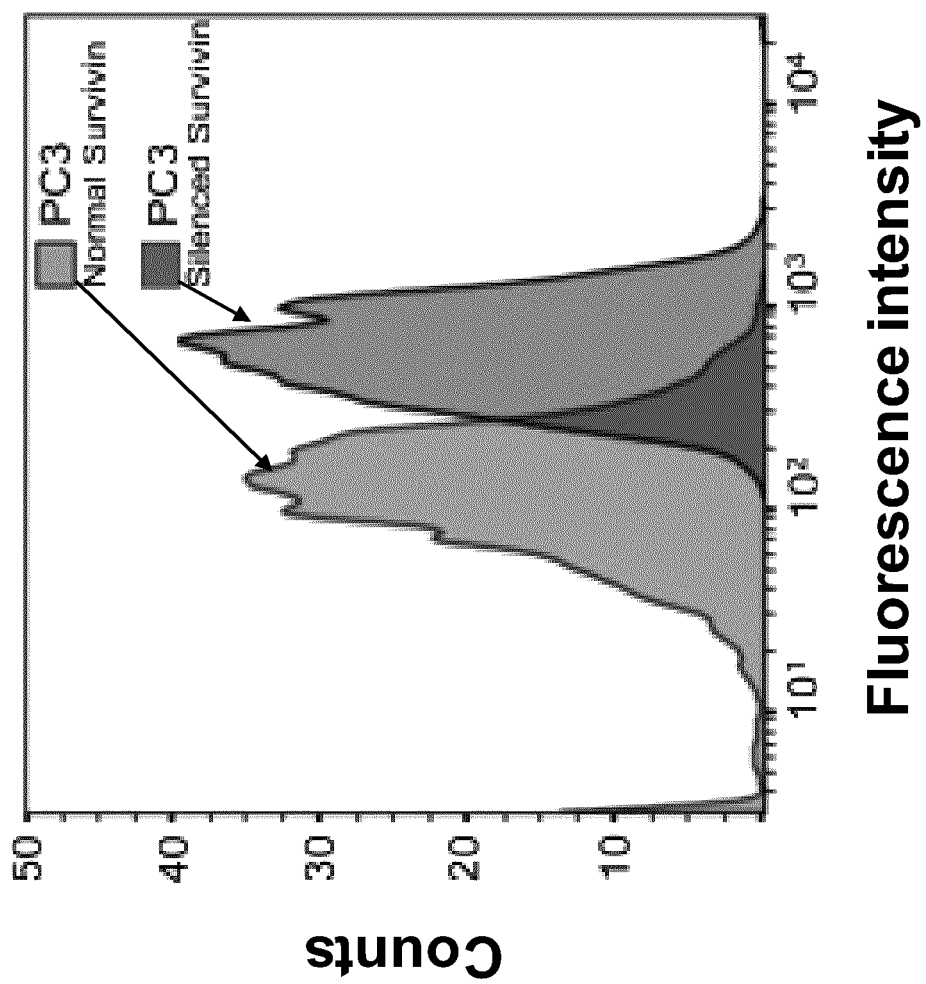
FIG. 19 is a graph of example flow cytometric analysis of survivin protein in PC3 cells before and after silencing the survivin gene.

Flow cytometric analysis of the survivin protein revealed that the survivin protein level within the cells was in the order of PC3>transfected PC3 cells (FIG. 19). FIG. 19 is an example graph of flow cytometric analysis of survivin protein in PC3 cells before and after silencing the survivin gene.

The results corroborated the mRNA expression data obtained using the disclosed approach. In addition, the results were further confirmed with immunostaining in which transfected cells were immunostained with an antibody specific to the survivin protein. Transfected cells have exhibited lower expression of the survivin protein (yellow channel), as shown in example FIG. 20.

Figure 20:
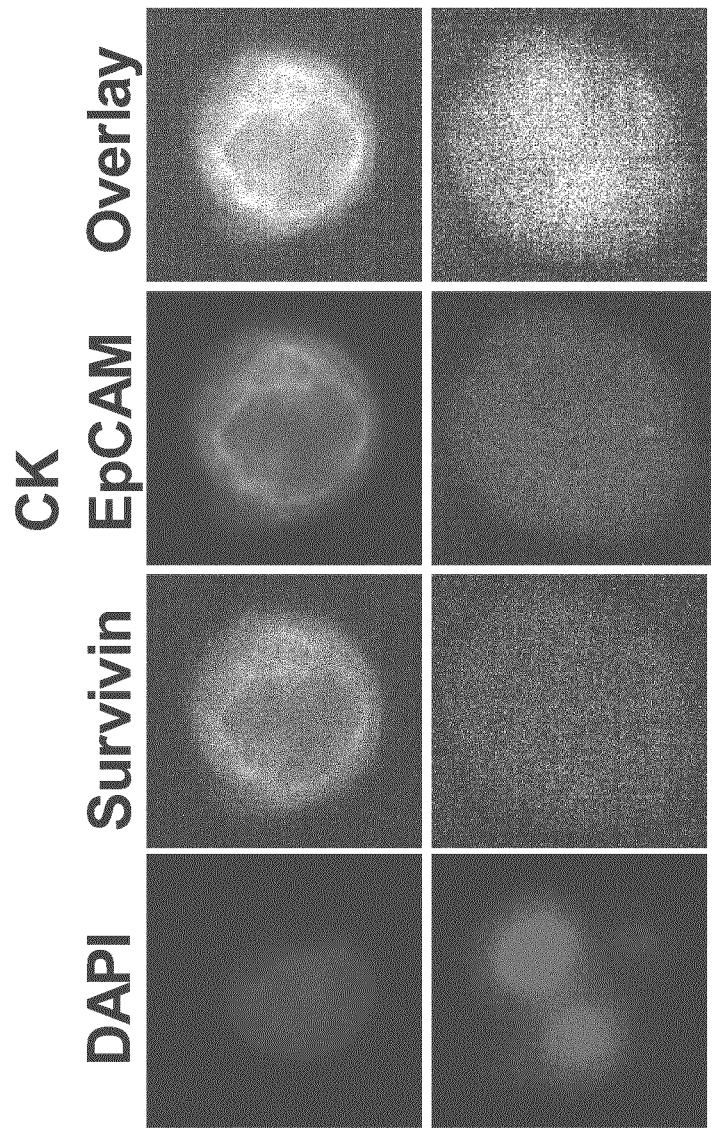
FIG. 20 shows example fluorescence microscopy images of PC3 cells before (top) and after survivin silencing (bottom).

FIG. 20 shows example fluorescence microscopy images of PC3 cells before (top) and after survivin silencing (bottom). The cells were immunostained with APC-labeled anti-CK, APC-labeled anti-EpCAM, DL555-labeled anti-survivin, and DAPI. Only CK$^+$/EpCAM$^+$/DAPI$^+$ cells were counted.

The disclosed approach was further used to analyze three prostate cancer specific mRNAs, including full-length androgen receptor (AR-FL), AR splice variant 7 (AR-V7), and TMPRSS2/ERG in VCaP, LnCAP, and PC3 cells. Notably, AR mRNA is considered the key oncogenic driver at various stages of prostate cancer development and progression[18]. AR-V7 mRNA is the most abundantly expressed variant that drives prostate cancer during androgen deprivation therapy[19]. It was recently identified as a predictive biomarker for the resistance to abiraterone and enzalutamide in metastatic castrate-resistant prostate cancer patients[20]. TMPRSS2 (Exon 1)/ERG (Exon 4) is the most frequent gene fusion in prostate cancer, appearing in about 50% of prostate cancer patients and 90% of all prostate cancer gene fusions[21]. In addition, TMPRSS2/ERG is absent in healthy cells and was found to correlate with cancer aggression and metastatic potential, the fact that made it more attractive as a diagnostic and prognostic marker than serum PSA[22].

The expression pattern of AR-FL mRNA (FIGS. 21 and 22), AR-V7 mRNA (FIGS. 23 and 24), and TMPRSS2/ERG mRNA (FIGS. 25 and 26) were determined using the disclosed approach in the three prostate cancer cell lines. In addition, the expression was calculated for each mRNA (FIG. 27).

Figure 21:
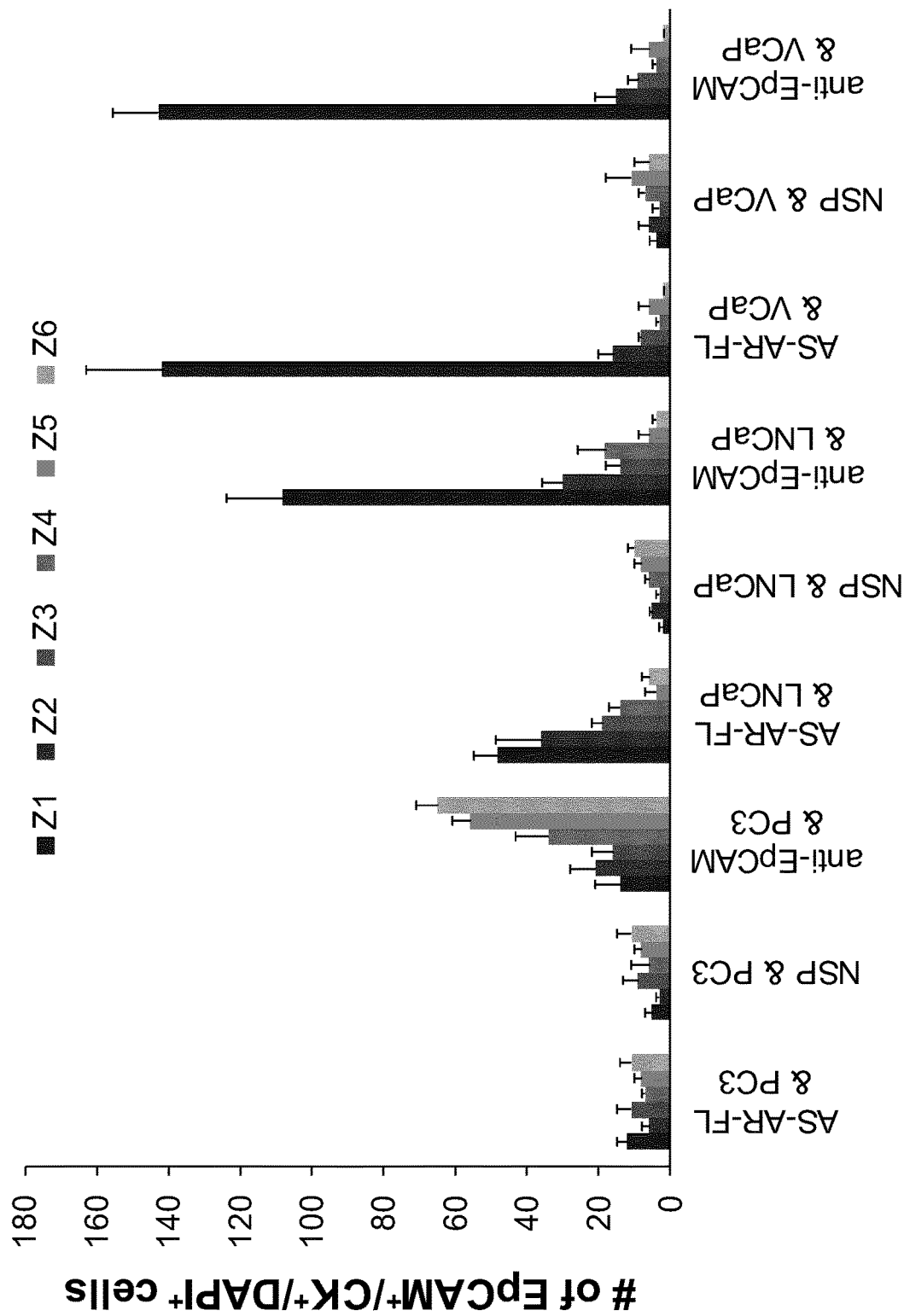
FIG. 21 is a chart illustrating example capture of three prostate cancer cell lines (PC3, LNCaP, VCaP) based on the expression levels of AR-FL mRNA in these cells.

FIG. 21 is an example chart showing capture of cancer cells by targeting their cellular AR-FL mRNA. Three prostate cancer cell lines, including PC3, LNCaP, and VCaP, were fixed with 4% PFA and permeabilized with 0.3% TX-100. The cells were incubated with two MNPs-tagged DNA probes complementary to the target AR-FL mRNA (AS-AR-FL). A control experiment was carried out in which the cells were incubated with MNPs-tagged nonspecific dual probe (NSP), subsequent to cell fixation and permeabilization. Another control experiment was carried out in which the cells were incubated with MNPs-tagged anti-EpCAM. Two hundred cells were used in these trials. The cells were loaded into the microfluidic device 6 at a flow rate of 600 μL h$^{-1}$, stained with APC-labeled anti-CK, APC-labeled anti-EpCAM, and DAPI. Only CK$^+$/EpCAM$^+$/DAPI$^+$ cells were counted.

Figure 22:
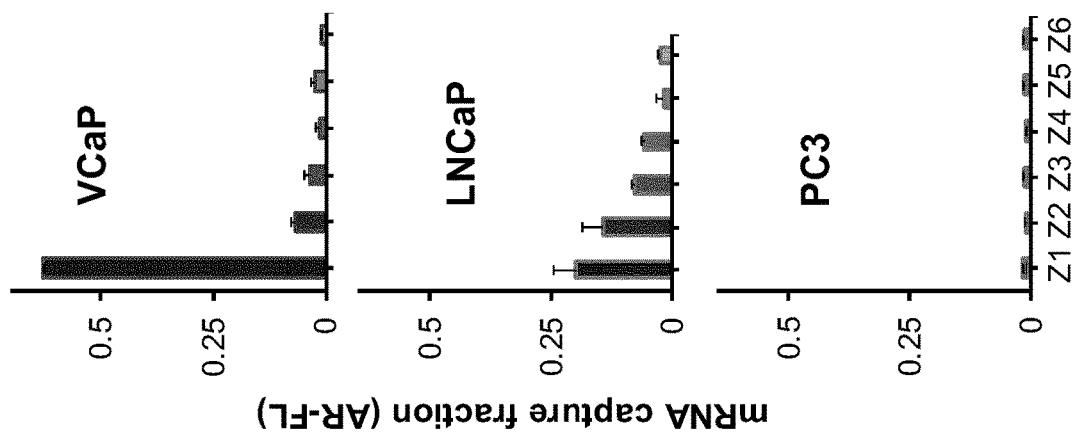
FIG. 22 shows graphs of example determination of the AR-FL mRNA capture fraction in PC3, LNCaP, and VCaP cells using the disclosed microfluidic approach.

FIG. 22 shows graphs of an example analysis of AR-FL mRNA in PC3, LNCaP, and VCaP cells using the microfluidic approach. Two hundred cells were used in these trials. The curves represent the normal distribution fit to the $EI_{mRNA}$ data.

Figure 23:
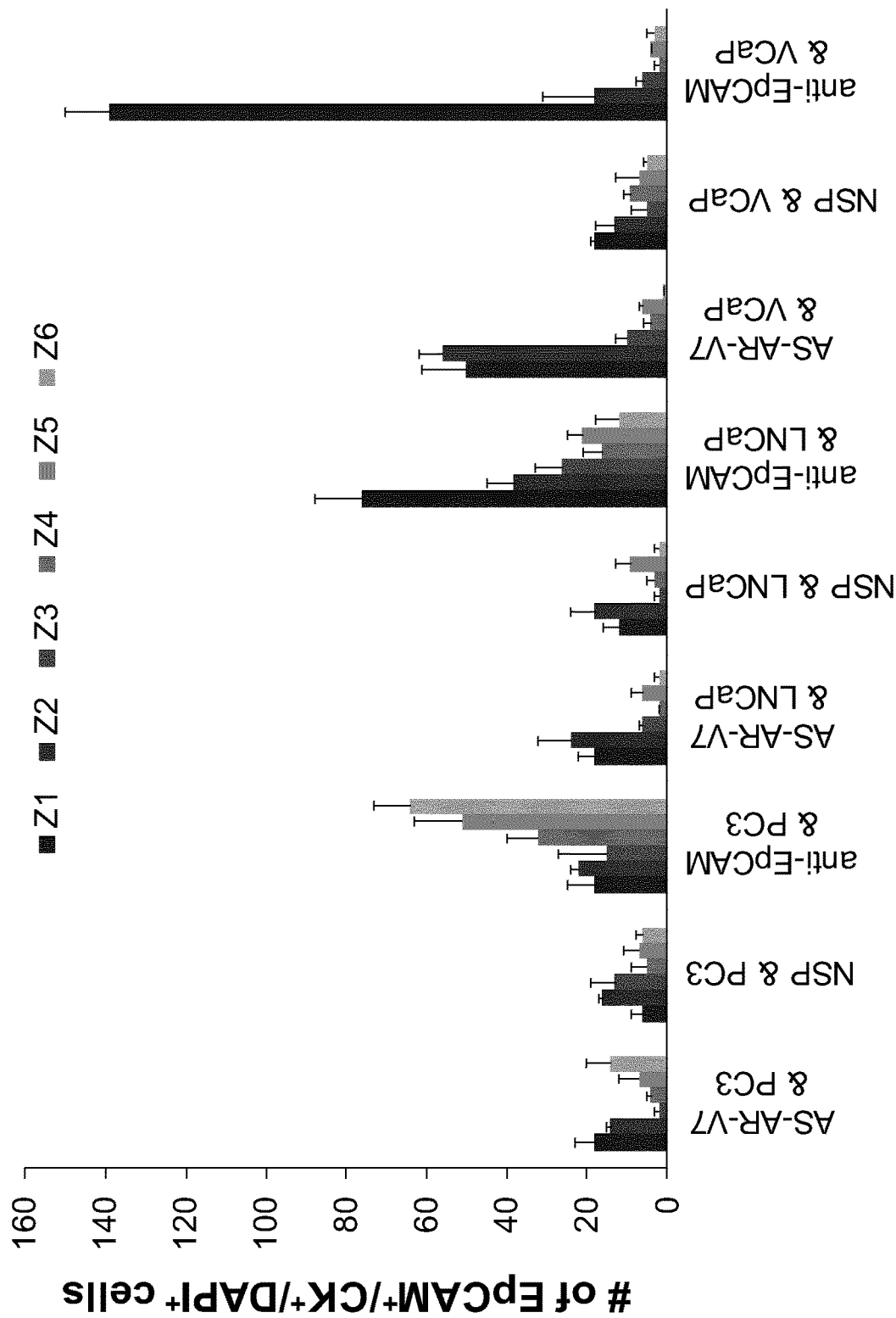
FIG. 23 is a chart illustrating example capture of three prostate cancer cell lines (PC3, LNCaP, VCaP) based on the expression levels of AR-V7 mRNA in these cells.

FIG. 23 is an example graph showing capture of cancer cells by targeting their cellular AR-V7 mRNA. Three prostate cancer cell lines (PC3, LNCaP, and VCaP) were fixed with 4% PFA and permeabilized with 0.3% TX-100. The cells were incubated with two MNPs-tagged DNA probes complementary to the target AR-V7 mRNA (AS-AR-V7). A control experiment was carried out in which the cells were incubated with MNPs-tagged nonspecific dual probe (NSP), subsequent to cell fixation and permeabilization. Another control experiment was carried out in which the cells were incubated with MNPs-tagged anti-EpCAM. Two hundred cells were used in these trials. The cells were loaded into the microfluidic device 6 at a flow rate of 600 μL h$^{-1}$, stained with APC-labeled anti-CK, APC-labeled anti-EpCAM, and DAPI. Only CK$^+$/EpCAM$^+$/DAPI$^+$ cells were counted.

Figure 24:
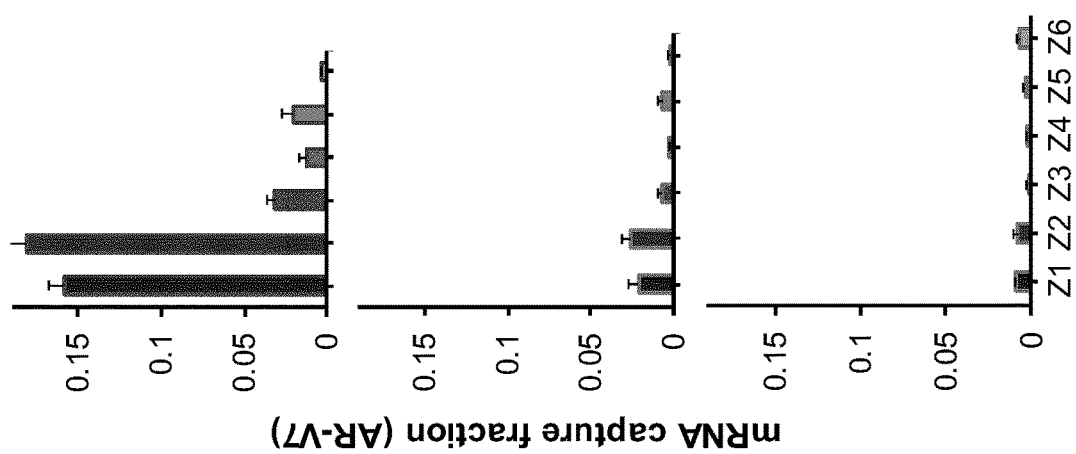
FIG. 24 shows graphs of example determination of the AR-V7 mRNA capture fraction in PC3, LNCaP, and VCaP cells using the disclosed microfluidic approach.

FIG. 24 shows graphs of the example analysis of AR-V7 mRNA in PC3, LNCaP, and VCaP cells using the microfluidic approach. Two hundred cells were used in these trials. The curves represent the normal distribution fit to the $EI_{mRNA}$ data.

Figure 25:
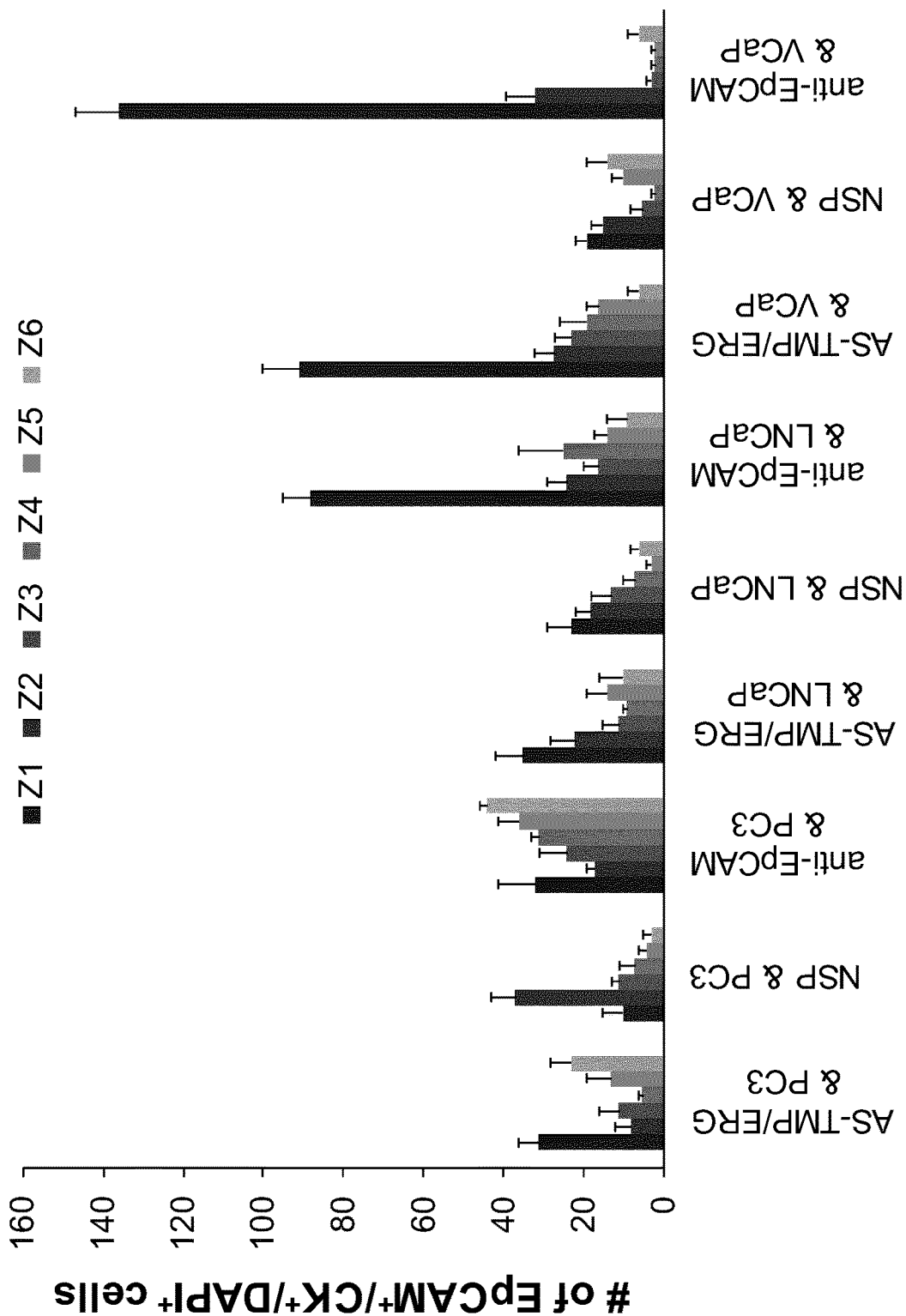
FIG. 25 is a chart illustrating example capture of three prostate cancer cell lines (PC3, LNCaP, VCaP) based on the expression levels of TMPRSS2/ERG mRNA in these cells.

FIG. 25 is an example graph showing capture of cancer cells by targeting their cellular TMPRSS2/ERG mRNA in prostate cancer cell lines. Three prostate cancer cell lines (PC3, LNCaP, and VCaP) were fixed with 4% PFA and permeabilized with 0.3% TX-100. The cells were incubated with two MNPs-tagged DNA probes complementary to the target mRNA (AS-TMP/ERG). A control experiment was carried out in which the cells were incubated with MNPs-tagged nonspecific dual probe (NSP), subsequent to cell fixation and permeabilization. Another control experiment was carried out in which the cells were incubated with MNPs-tagged anti-EpCAM. Two hundred cells were used in these trials. The cells were loaded into the microfluidic device 6 at a flow rate of 600 μL h$^{-1}$, stained with APC-labeled anti-CK, APC-labeled anti-EpCAM, and DAPI. Only CK$^+$/EpCAM$^+$/DAPI$^+$ cells were counted.

Figure 26:
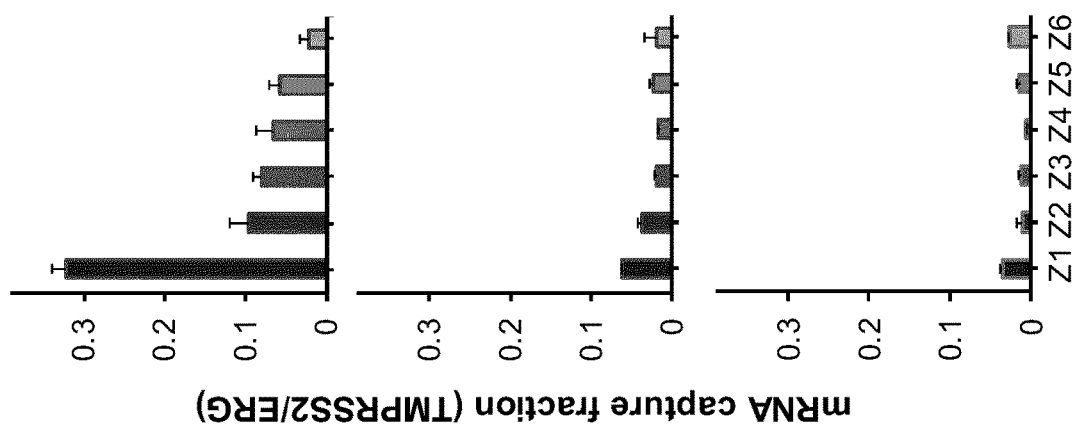
FIG. 26 shows graphs of example determination of the TMPRSS2/ERG mRNA capture fraction in PC3, LNCaP, and VCaP cells using the disclosed microfluidic approach.
Figure 27:
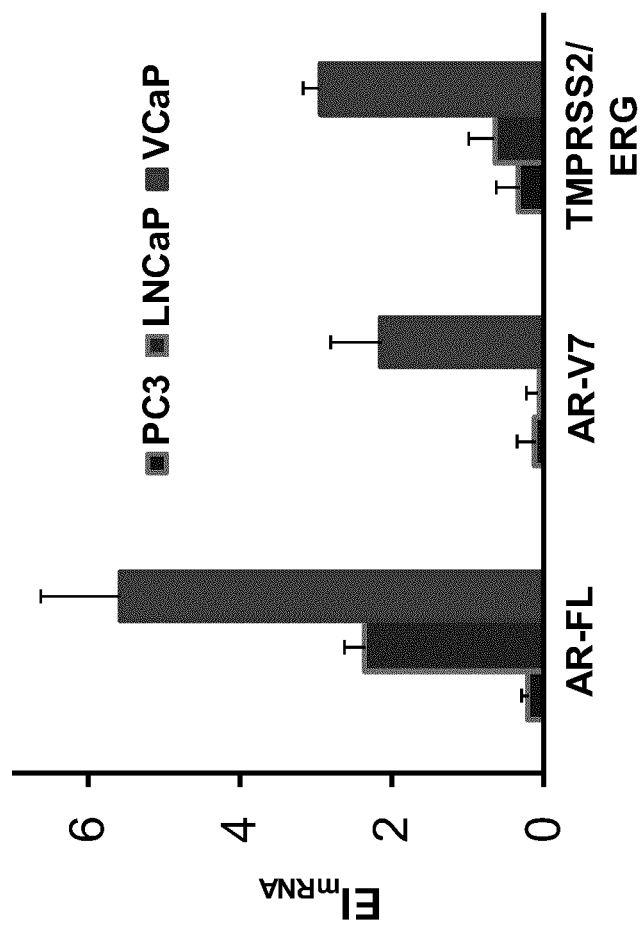
FIG. 27 is a chart of example expression indices of AR-FL, AR-V7, and TMPRSS2/ERG mRNA determined using the disclosed microfluidic approach.

FIG. 26 shows example graphs of the analysis of TMPRSS2/ERG mRNA in PC3, LNCaP, and VCaP cells using the microfluidic approach. Two hundred cells were used in these trials. The curves represent the normal distribution fit to the EI$_{mRNA}$ data.

FIG. 27 is an example chart of the expression indices of AR-FL, AR-V7, and TMPRSS2/ERG mRNAs determined using the microfluidic approach.

Figure 28:
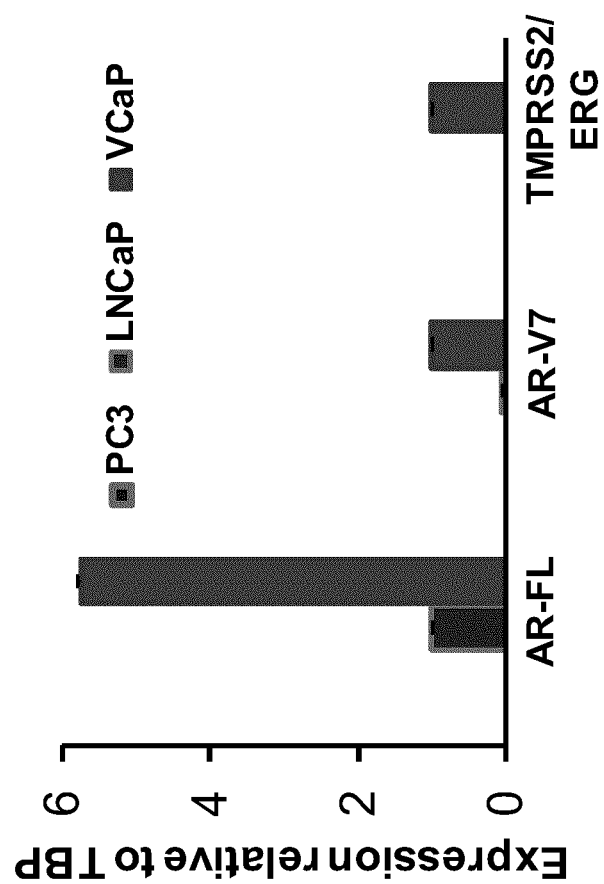
FIG. 28 is a chart of example RT-qPCR analysis of AR-FL, AR-V7, and TMPRSS2/ERG mRNAs relative to TBP in PC3, LNCaP, and VCaP cells.

To assess the results, RT-qPCR was used to analyze the aforementioned mRNAs in the three cell lines and the results are provided in FIG. 28. FIG. 28 shows the example total expression of AR-FL, AR-V7, and TMPRSS2/ERG mRNAs determined using RT-qPCR.

Head-to-head comparison of the results revealed a good agreement between both methods and indicated that the disclosed example approach can be used to quantify gene expression levels and generate mRNA expression patterns comparable to those determined by RT-qPCR.

Figure 29:
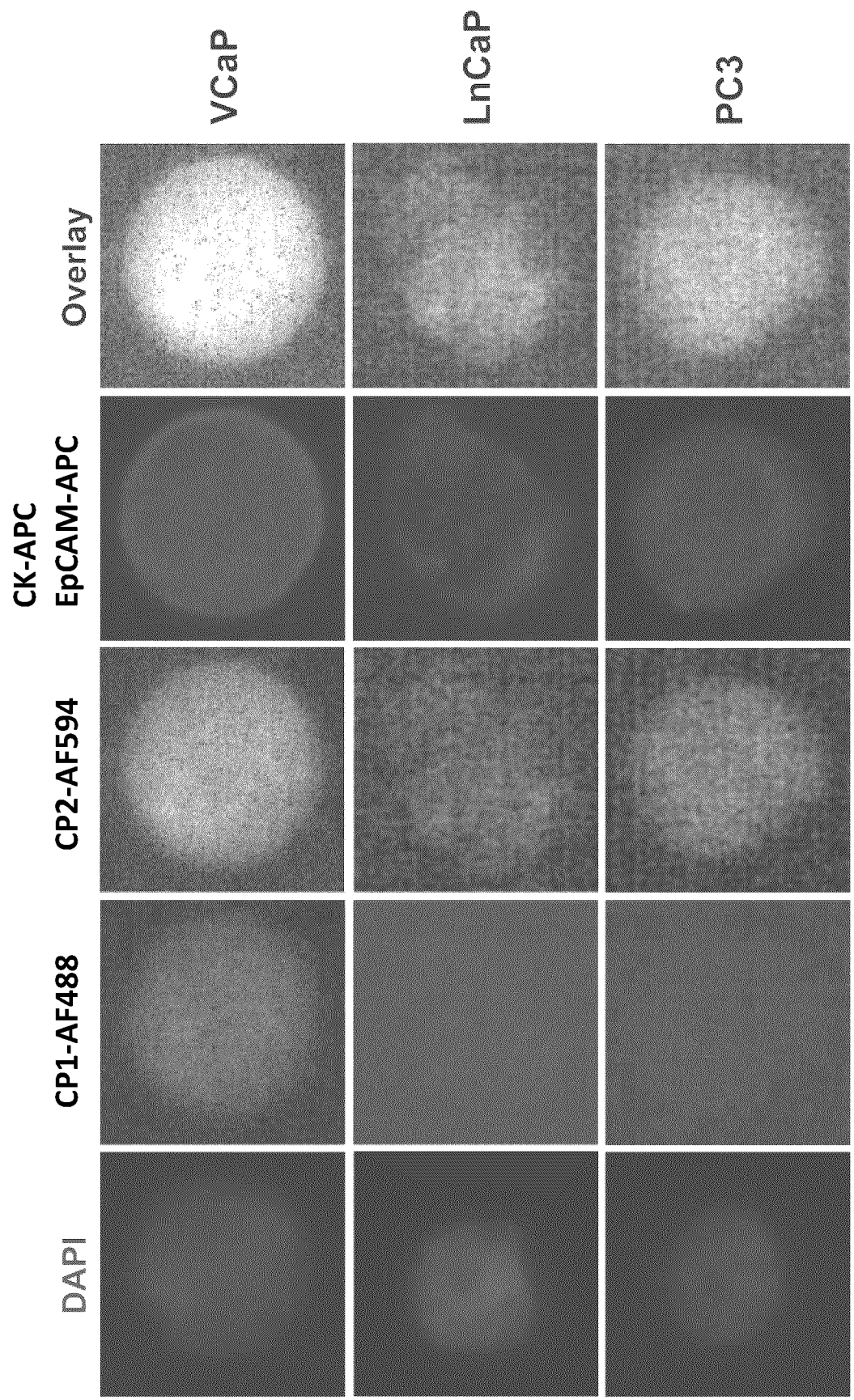
FIG. 29 shows florescence microscopy images of example dual probe internalization into the cells.

Fluorescence microscopy was used to gain better insights into TMPRSS2/ERG specific dual probe internalization within three prostate cancer cell lines, including VCaP, LnCaP, and PC3. Fluorescence microscopy images revealed the internalization of AF488-labeled CP1 in VCaP cells. However, no green fluorescence was observed in both LNCaP and PC3 cells (FIG. 29). In addition, AF594-CP2 was internalized in the three cell lines (yellow channel).

FIG. 29 shows example florescence microscopy images showing proof of the dual probe internalization into the cells. Three prostate cancer cell lines (200 cells) were fixed with 4% PFA and permeabilized with 0.3% TX-100. The cells were incubated with CP1 (complementary to TMPRSS2/ERG mRNA) modified with MNPs at one end and AF488 at the other end, and CP2 (complementary to ERG mRNA) modified with MNPs at one end and AF594 at the other end. The cells were loaded into the microfluidic device 6 at a flow rate of 600 μL h$^{-1}$. The cells were immunostained with APC-labeled anti-CK, APC-labeled anti-EpCAM, and DAPI.

Transmission electron microscopy (TEM) images supported the previous finding and revealed the formation of clusters of magnetic nanoparticles within PC3 cells after targeting the survivin mRNA with a complementary dual probe (CP1+CP2). No cluster formation was observed when single complementary probes were used (CP1 or CP2), as shown in FIG. 30.

Figure 30:
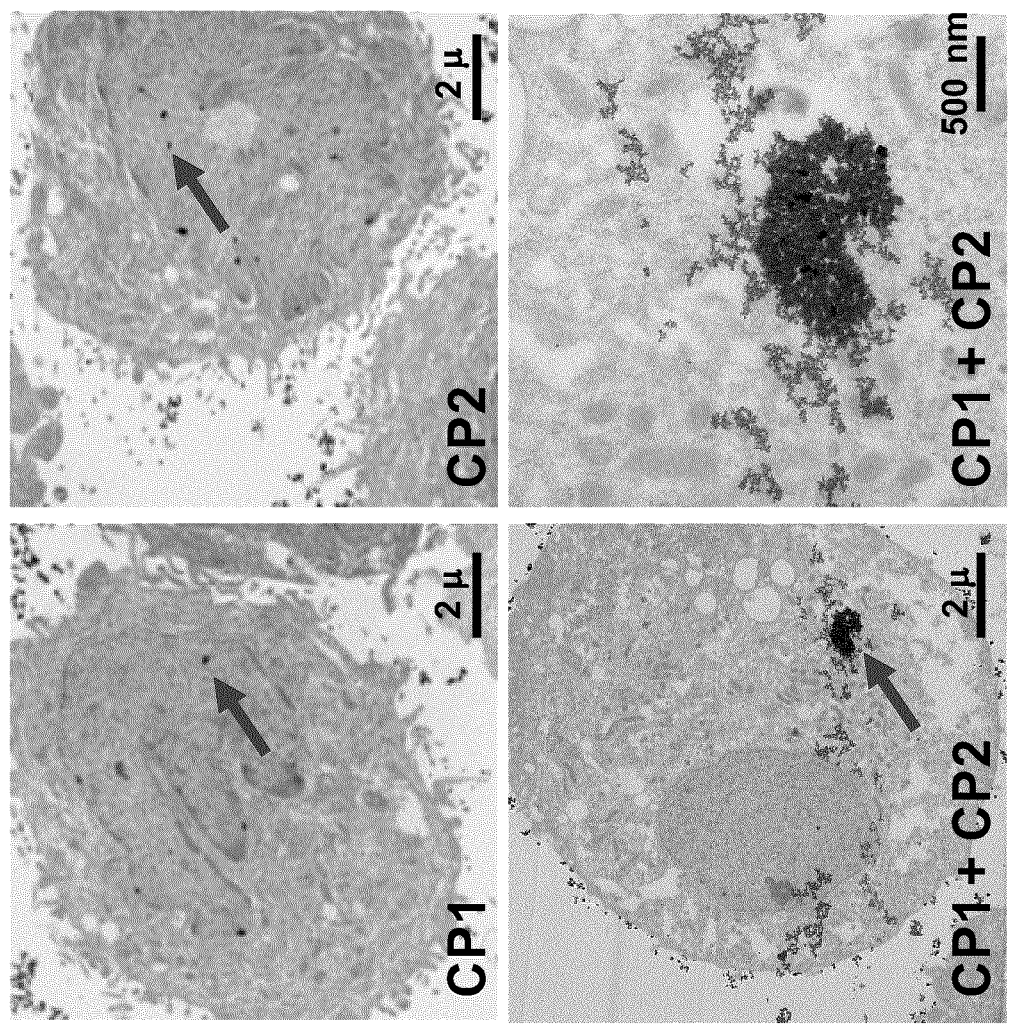
FIG. 30 shows TEM images of example dual probe induced clustering of MNPs within the cells.

FIG. 30 shows example dual probe-induced clustering of MNPs within the cells. Representative TEM images showing the accumulation of magnetic clusters in PC3 cells (bottom), whereas no cluster formation was observed in PC3 cells (top) after incubation with single probes (CP1 or CP2).

Figure 31:
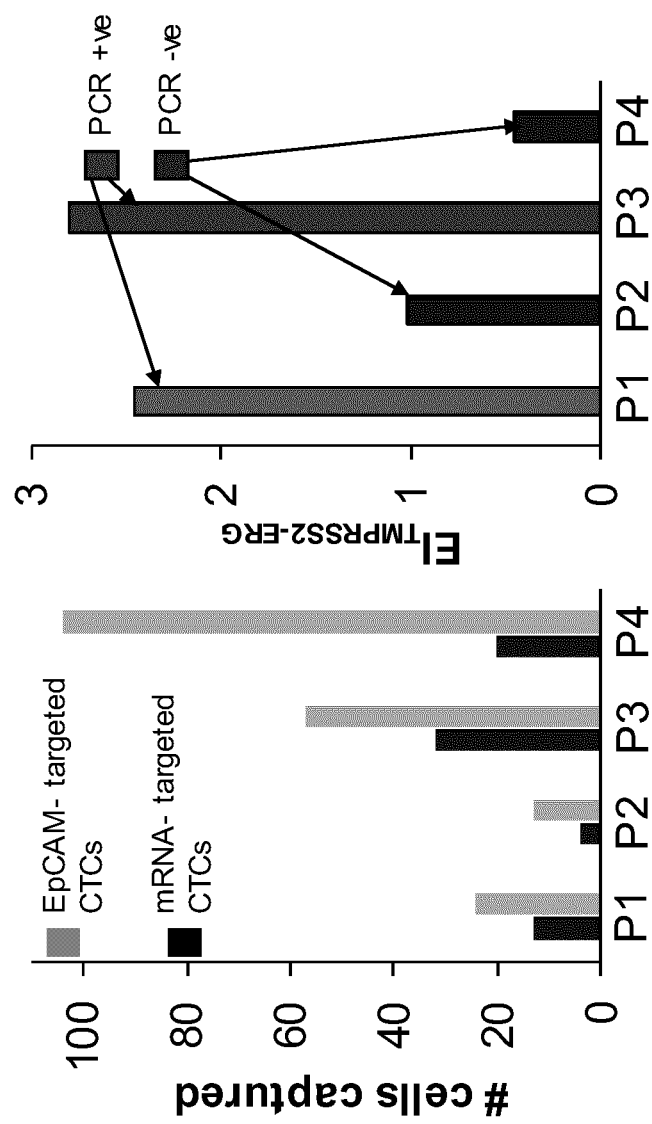
FIG. 31 shows graphs illustrating example cellular determination of TMPRSS2/ERG mRNA in CRPC patient's blood subsequent to RBCs and WBCs depletion using an example of the disclosed microfluidic approach.
Figure 32:
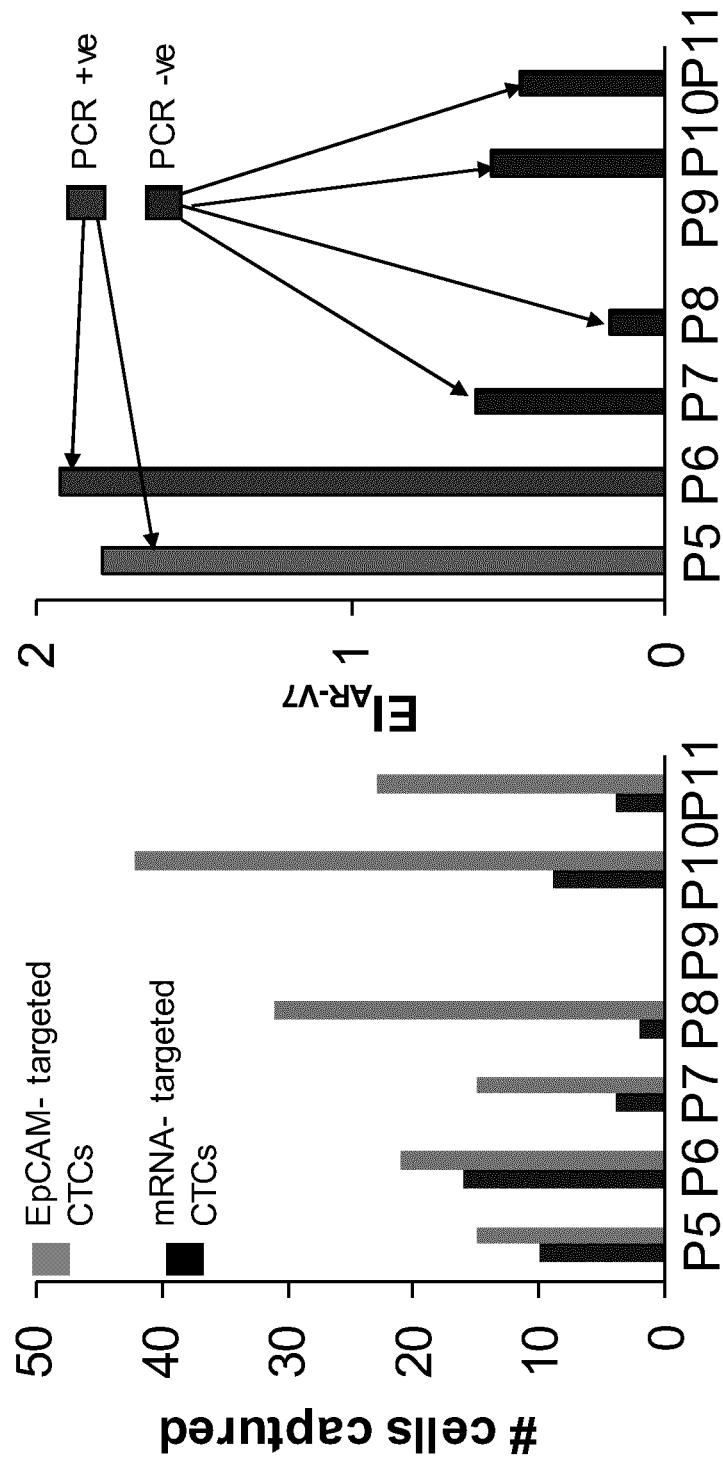
FIG. 32 shows graphs illustrating example cellular determination of AR-V7 mRNA in CRPC patient's blood subsequent to RBCs and WBCs depletion using an example of the disclosed microfluidic approach.

To demonstrate the clinical utility of the disclosed approach for mRNA analysis in CTCs, the low-abundance TMPRSS2/ERG and AR-V7 mRNAs in blood samples collected from a small cohort of patients undergoing treatment for metastatic castration-resistant prostate cancer (n=11) were analyzed, as shown in FIG. 31 and FIG. 32.

FIG. 31 shows the example capture of CTCs from CRPC patient's blood by targeting TMPRSS2/ERG mRNA. Four milliliters of blood were depleted of RBCs and WBCs using the Ficoll method and MNPs-tagged anti-CD15 antibody, respectively. The cells were subsequently incubated with the MNPs-tagged AS-TMP/ERG. A control experiment is carried out in which the cells were incubated with the MNPs-tagged NSP, subsequent to cell fixation and permeabilization. Another control experiment is carried out in which the cells were incubated with MNPs-tagged anti-EpCAM. The cells were loaded into the microfluidic device 6 at a flow rate of 600 μL h$^{-1}$, stained with APC-labeled anti-CK, APC-labeled anti-EpCAM, AF488-labeled anti-CD45, and DAPI. Only CK$^+$/EpCAM$^+$/DAPI$^+$ cells were counted.

An average of 12 mL of blood was analyzed per patient and CTCs were identified using immunofluorescence staining techniques. A patient sample was considered positive for TMPRSS2/ERG when the EITMPRSS2/ERG was at least 1.5. It was observed that the ratio of number of CTCs captured by the dual probe to the total number of CTCs determined using the EpCAM beads was higher in TMPRSS2/ERG positive samples compared to samples lacking the gene fusion (FIG. 31, left graph). In addition, samples that tested positive for the TMPRSS2/ERG gene fusion by the disclosed approach have exhibited significantly higher expression than those that tested negative as measured by PCR (FIG. 31, right graph).

FIG. 32 shows the example capture of CTCs from CRPC patient's blood by targeting AR-V7 mRNA. Four milliliters of blood were depleted of RBCs and WBCs using the Ficoll method and MNPs-tagged anti-CD15 antibody, respectively. The cells were subsequently incubated with the MNPs-tagged AS-AR-V7. A control experiment is carried out in which the cells were incubated with the MNPs-tagged NSP, subsequent to cell fixation and permeabilization. Another control experiment is carried out in which the cells were incubated with MNPs-tagged anti-EpCAM. The cells were loaded into the microfluidic device 6 at a flow rate of 600 μL h$^{-1}$, stained with APC-labeled anti-CK, APC-labeled anti-EpCAM, AF488-labeled anti-CD45, and DAPI. Only CK$^+$/EpCAM$^+$/DAPI$^+$ cells were counted.

An average of 12 mL of blood was analyzed per patient and CTCs were identified using immunofluorescence staining techniques. A patient sample was considered positive for AR-V7 when the EIAR-V7 was at least 1. It was observed that the ratio of number of CTCs captured by the dual probe to the total number of CTCs determined using the EpCAM beads was higher in AR-V7 positive samples compared to samples lacking the gene fusion (FIG. 32, left graph). In addition, samples that tested positive for the AR-V7 gene fusion by the disclosed approach have exhibited significantly higher expression than those that tested negative as measured by PCR (FIG. 32, right graph).

Figure 33:
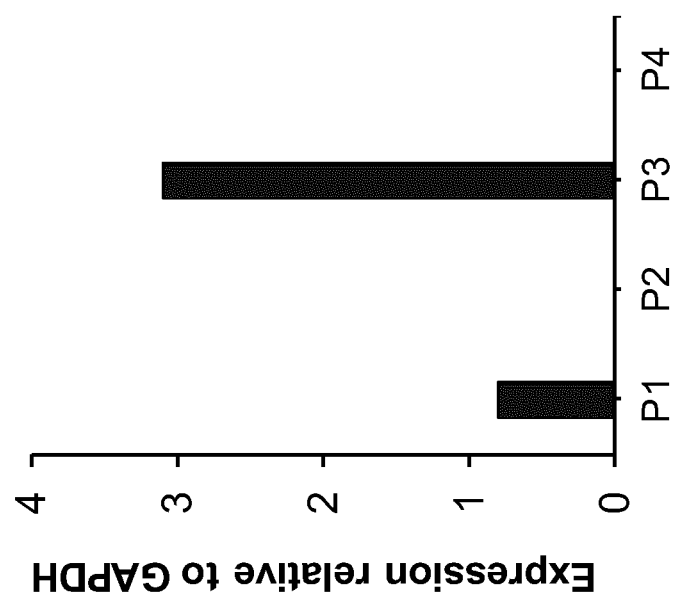
FIG. 33 is a chart of example RT-qPCR analysis of TMPRSS2/ERG mRNA in CRPC patient's blood subsequent to RBCs and WBCs depletion.

A parallel RT-qPCR analysis of TMPRSS2/ERG mRNA corroborated the data (FIG. 33).

Figure 34:
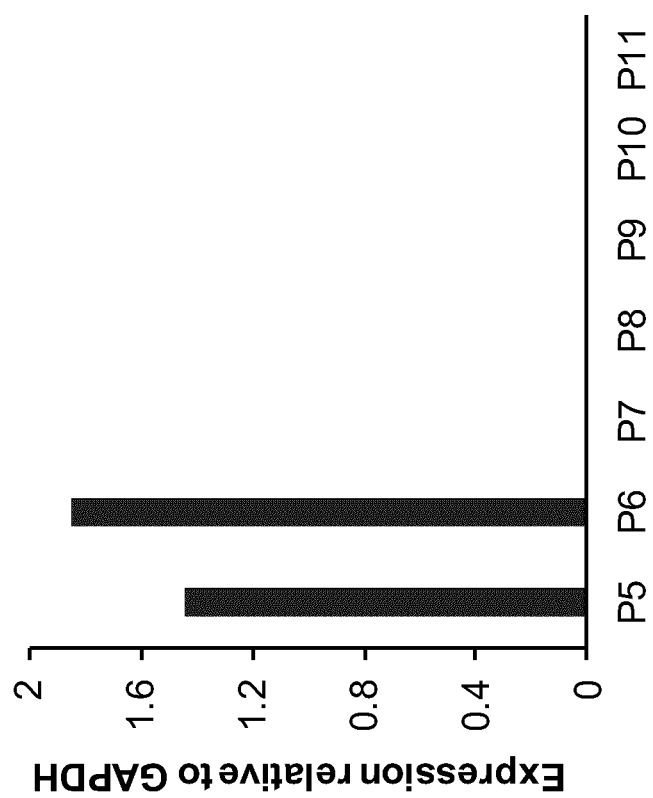
FIG. 34 is a chart of example RT-qPCR analysis of AR-V7 mRNA in CRPC patient's blood subsequent to RBCs and WBCs depletion.

A parallel RT-qPCR analysis of the AR-V7 mRNA corroborated the data (FIG. 34).

Figure 35:
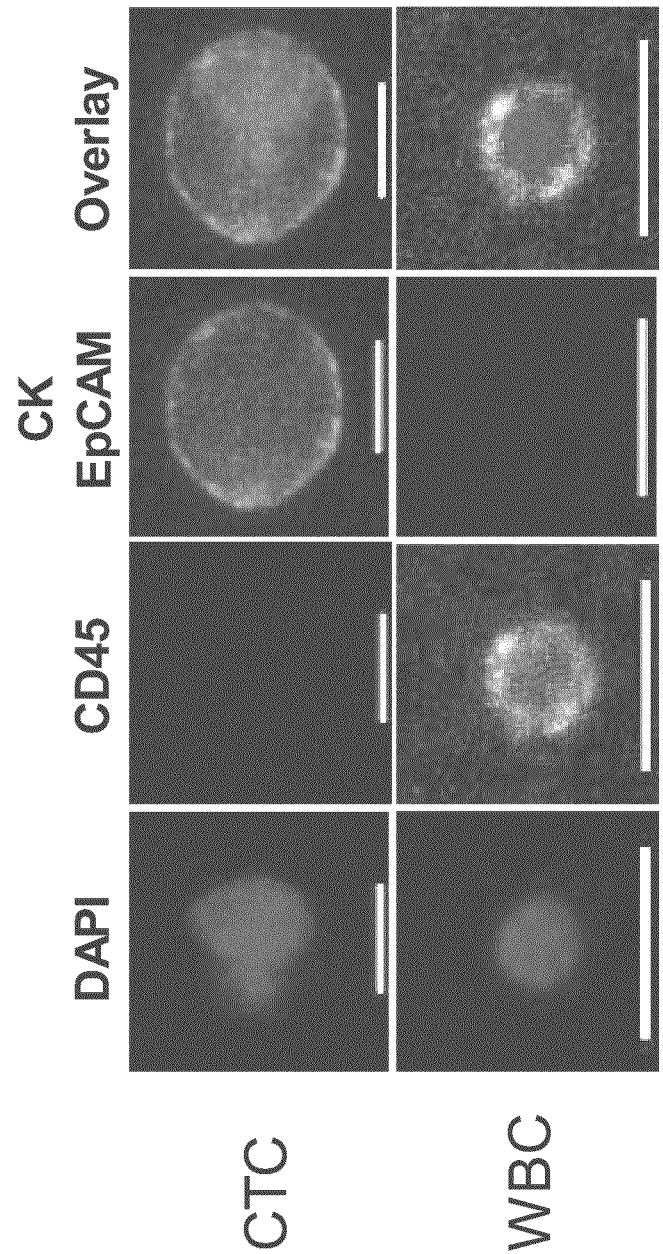
FIG. 35 shows example fluorescence microscopy images of a representative CTC captured from a prostate cancer patient's blood sample versus a white blood cell. The scale bar is 15 µm.

Representative images of CTCs captured from patient samples versus a white blood cell are shown in FIG. 35.

FIG. 35 shows a representative image of a CTC captured from a prostate cancer patient's blood sample versus a white blood cell. The cells were stained with APC-labeled anti-CK, APC-labeled anti-EpCAM, AF488-labeled anti-CD45, and DAPI. Only CK$^+$/EpCAM$^+$/CD45$^-$/DAPI$^+$ cells are counted as CTCs.

In summary, the disclosed example method provides an amplification-free means to characterize gene expression patterns in intact cancer cells and may be broadly applicable to other cell types, including non-cancer cells.

The disclosed example method provides capture probes designed to capture cells containing the mRNA transcripts: survivin, TMPRSS2/ERG, AR, or AR-V7. Other capture probes and mRNA transcripts are contemplated. For example, capture probes against the mRNA transcripts: PDL1, PD1, and PARP are listed in Table 1. The disclosed method may also be broadly applicable to cell capture based on polynucleotides other than mRNA, such as microRNA (miRNA) or DNA.

The disclosed method has the ability to combine cellular mRNA analysis with cellular proteins identification, a critical tool for defining specific cell subsets in heterogeneous populations.

Additionally, this disclosed approach may be useful for the early detection of cancer by paving the way toward elucidating the molecular profiles of CTCs in-line, without interference from residual blood cells. This can be implemented for better understanding of cancer progression in real-time to improve the clinical outcome.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. Elowitz, M. B., Levine, A. J., Siggia, E. D. & Swain, P. S. Stochastic gene expression in a single cell. *Science* 297, 1183-1186 (2002).
2. Bendall, S. C. & Nolan, G. P. From single cells to deep phenotypes in cancer. *Nat. Biotechnol.* 30, 639-647 (2012).
3. Yu, M. et al. Circulating breast tumor cells exhibit dynamic changes in epithelial and mesenchymal composition. *Science* 339, 580-584 (2013).
4. Kalinich, M. et al. An RNA-based signature enables high specificity detection of circulating tumor cells in hepatocellular carcinoma. *Proc. Natl. Acad. Sci. U.S.A* 114, 1123-1128 (2017).
5. Clark, I. C. & Abate, A. R. Finding a helix in a haystack: nucleic acid cytometry with droplet microfluidics. *Lab Chip* 17, 2032-2045 (2017).
6. Briley, W. E., Bondy, M. H., Randeria, P. S., Dupper, T. J. & Mirkin, C. A. Quantification and real-time tracking of RNA in live cells using Sticky-flares. *Proc. Natl. Acad. Sci. U.S.A* 112, 9591-95955 (2015).
7. Geiss, G. K. et al. Direct multiplexed measurement of gene expression with color-coded probe pairs. *Nat. Biotechnol.* 26, 317-325 (2008).
8. Deng, Q., Ramskold, D., Reinius, B. & Sandberg, R. Single-cell RNA-seq reveals dynamic, random monoallelic gene expression in mammalian cells. *Science* 343, 193-196 (2014).
9. Livak, K. J. et al. Methods for qPCR gene expression profiling applied to 1440 lymphoblastoid single cells. *Methods* 59, 71-79 (2013).
10. Lyubimova, A. et al. Single-molecule mRNA detection and counting in mammalian tissue. *Nat. Protoc.* 8, 1743-1758 (2013).
11. Itzkovitz, S. & van Oudenaarden, A. Validating transcripts with probes and imaging technology. *Nat. Methods* 8, S12-19 (2011).
12. Halo, T. L. et al. NanoFlares for the detection, isolation, and culture of live tumor cells from human blood. *Proc. Natl. Acad. Sci. U.S.A.* 111, 17104-17109 (2014).
13. Alix-Panabieres, C. & Pantel, K. Challenges in circulating tumour cell research. *Nat. Rev. Cancer* 14, 623-631 (2014).
14. Carrasco, R. A. et al. Antisense inhibition of survivin expression as a cancer therapeutic. *Mol. Cancer. Ther.* 10, 221-232 (2011).
15. Wang, S. et al. Potential clinical significance of a plasma-based KRAS mutation analysis in patients with advanced non-small cell lung cancer. *Clin. Cancer Res.* 16, 1324-1330 (2010).
16. Altieri, D. C. Validating survivin as a cancer therapeutic target. *Nat. Rev. Cancer* 3, 46-54 (2003).
17. Fulda, S. & Vucic, D. Targeting IAP proteins for therapeutic intervention in cancer. *Nat. Rev. Drug Discov.* 11, 109-124 (2012).
18. Watson, P. A., Arora, V. K. & Sawyers, C. L. Emerging mechanisms of resistance to androgen receptor inhibitors in prostate cancer. *Nat. Rev. Cancer* 15, 701-711 (2015).
19. Robinson, D. et al. Integrative clinical genomics of advanced prostate cancer. *Cell* 161, 1215-1228 (2015).
20. Antonarakis, E. S. et al. AR-V7 and resistance to enzalutamide and abiraterone in prostate cancer. *N. Engl. J. Med.* 371, 1028-1038 (2014).
21. Tomlins, S. A. et al. Recurrent fusion of TMPRSS2 and ETS transcription factor genes in prostate cancer. *Science* 310, 644-648 (2005).
22. Tomlins, S. A. et al. Urine TMPRSS2:ERG fusion transcript stratifies prostate cancer risk in men with elevated serum PSA. *Sci. Transl. Med.* 3, 94ra72 (2011).

The invention claimed is:

1. A method of magnetically capturing cells, the method comprising:

introducing a first capture probe and a second capture probe into the cells, the first capture probe and the second capture probe each configured to be complementary to a respective section of target mRNA within the cells, wherein binding of the first and second capture probes to the respective sections of the target mRNA results in tagging of the cells and causes the first and second capture probes to form clusters with each other;

wherein the first capture probe is complementary to a first section of the target mRNA and the second capture probe is complementary to a second section of the target mRNA, wherein the first section of the target mRNA is different than the second section of the target mRNA;

wherein the first capture probe and the second capture probe are each bound to magnetic nanoparticles (MNPs) that, when trapped within tagged cells, cause the tagged cells to be susceptible to magnetic forces; and introducing a plurality of cells comprising the tagged cells into a device configured to magnetically capture the tagged cells.

2. The method of claim 1, wherein the target mRNA is at least one of survivin, TMPRSS2/ERG, AR, AR-V7, PD1, PDL1, and PARP mRNA.

3. The method of claim 1, wherein the first capture probe has a first sequence and the second capture probe has a second sequence, and wherein:

the first sequence of the first capture probe comprises 5' CAG TTC TTG AAT GTA GAG AT 3' (SEQ ID NO: 7) and the second sequence of the second capture probe comprises 5' GCA GGC GCA GCC CTC CAA GA 3' (SEQ ID NO: 8);

the first sequence of the first capture probe comprises 5' GAT AAG GCT TCC TGC CGC GC 3' (SEQ ID NO: 1) and the second sequence of the second capture probe comprises 5' CAA CGA CTG GTC CTC ACT CA 3' SEQ ID NO: 2);

the first sequence of the first capture probe comprises 5' TGC TTT CAT GCA CAG GAA TT 3' (SEQ ID NO: 9) and the second sequence of the second capture probe comprises 5' CTG GAA TAA TGC TGA AGA GT 3' (SEQ ID NO: 10); or the first sequence of the first capture probe comprises 5' CTG ATG AAG AGA AGC ATG TG 3' (SEQ ID NO: 11) and the second sequence of the second capture probe comprises 5' TGG GAG AAG AAT GAG AGG CT 3' (SEQ ID NO: 12).

4. The method of claim 1, wherein the plurality of cells are cancer cells.

5. The method of claim 4, wherein the cancer cells are prostate cancer cells.

6. The method of claim 1, wherein the device is a microfluidic device.

7. A system for analyzing mRNA in cells comprising:
a first capture probe and a second capture probe, the first capture probe and the second capture probe each configured to be complementary to a respective section of target mRNA within the cells, wherein binding of the first and second capture probes to the respective sections of the target mRNA results in tagging of the cells and causes the first and second capture probes to form clusters with each other;
wherein the first capture probe is complementary to a first section of the target mRNA and the second capture probe is complementary to a second section of the target mRNA, wherein the first section of the target mRNA is different than the second section of the target mRNA;
wherein the first capture probe and the second capture probe are each bound to magnetic nanoparticles (MNPs) that, when trapped within the tagged cells, cause the tagged cells to be susceptible to magnetic forces; and
a device configured to magnetically capture tagged cells.

8. The system of claim 7, wherein the device is a microfluidic device.

9. The system of claim 8, wherein the microfluidic device further comprises a plurality of sorting portions defined in the microfluidic device, each sorting portion including a respective plurality of flow rate-reducing structures, wherein each sorting portion promotes capture of respective different cells exhibiting respective different amounts of susceptibility to magnetic attraction force.

10. The system of claim 9, wherein the microfluidic device comprises at least six sorting portions.

11. The system of claim 7, wherein the target mRNA is at least one of survivin, TMPRSS2/ERG, AR, AR-V7, PD1, PDL1, and PARP mRNA.

12. The system of claim 7, wherein the first capture probe has a first sequence and the second capture probe has a second sequence, and wherein:
the first sequence of the first capture probe comprises 5' CAG TTC TTG AAT GTA GAG AT 3' (SEQ ID NO: 7) and the second sequence of the second capture probe comprises 5' GCA GGC GCA GCC CTC CAA GA 3' (SEQ ID NO: 8);
the first sequence of the first capture probe comprises 5' GAT AAG GCT TCC TGC CGC GC 3' (SEQ ID NO: 1) and the second sequence of the second capture probe comprises 5' CAA CGA CTG GTC CTC ACT CA 3' (SEQ ID NO: 2);
the first sequence of the first capture probe comprises 5' TGC TTT CAT GCA CAG GAA TT 3' (SEQ ID NO: 9) and the second sequence of the second capture probe comprises 5' CTG GAA TAA TGC TGA AGA GT 3' (SEQ ID NO: 10); or
the first sequence of the first capture probe comprises 5' CTG ATG AAG AGA AGC ATG TG 3' (SEQ ID NO: 11) and the second sequence of the second capture probe comprises 5' TGG GAG AAG AAT GAG AGG CT 3' (SEQ ID NO: 12).

13. The system of claim 7, wherein the cells are cancer cells.

14. The system of claim 13, wherein the cancer cells are prostate cancer cells.

* * * * *